US012760218B2

(12) United States Patent
Fujisawa et al.

(10) Patent No.: US 12,760,218 B2
(45) Date of Patent: Oct. 13, 2026

(54) COMPOUND, LIGHT-EMITTING MATERIAL, AND ORGANIC LIGHT-EMITTING DEVICE

(71) Applicant: KYULUX, INC., Fukuoka (JP)

(72) Inventors: Kaori Fujisawa, Fukuoka (JP); Yoshitake Suzuki, Fukuoka (JP); Yong Joo Cho, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 789 days.

(21) Appl. No.: 17/906,416

(22) PCT Filed: Mar. 17, 2021

(86) PCT No.: PCT/JP2021/010738
§ 371 (c)(1),
(2) Date: Sep. 15, 2022

(87) PCT Pub. No.: WO2021/187507
PCT Pub. Date: Sep. 23, 2021

(65) Prior Publication Data
US 2023/0051487 A1 Feb. 16, 2023

(30) Foreign Application Priority Data
Mar. 18, 2020 (JP) ................................ 2020-047708

(51) Int. Cl.
*C09K 11/06* (2006.01)
*C07D 209/86* (2006.01)
(Continued)

(52) U.S. Cl.
CPC ............ *C09K 11/06* (2013.01); *C07D 209/86* (2013.01); *C07F 5/027* (2013.01); *H10K 85/658* (2023.02);
(Continued)

(58) Field of Classification Search
CPC .................................................... H10K 85/322
See application file for complete search history.

(56) References Cited

U.S. PATENT DOCUMENTS

2019/0207112 A1* 7/2019 Hatakeyama ........ H10K 85/636
2020/0144512 A1 5/2020 Lin et al.
2021/0122765 A1 4/2021 Wolohan et al.

FOREIGN PATENT DOCUMENTS

CN 110452226 A 11/2019
CN 110627822 A 12/2019
(Continued)

OTHER PUBLICATIONS

Japanese and English version of International Preliminary Report on Patentability of Chapter I in PCT/JP2021/010738, mailed Sep. 20, 2022.
(Continued)

*Primary Examiner* — Peter F Godenschwager
(74) *Attorney, Agent, or Firm* — Troutman Pepper Locke LLP; James E. Armstrong, IV

(57) ABSTRACT

A compound represented by the following general formula has excellent light-emitting characteristics and emits light at a short wavelength. $Y^1$ is N—$R^A$; $Y^2$ is O, S, C═O or N—$R^A$; $R^A$ is an aryl group, etc.; $R^1$ to $R^{11}$ each are a hydrogen atom or a substituent; at least one of $R^1$ to $R^3$ is a carbazolyl group substituted with an aryl group, etc.

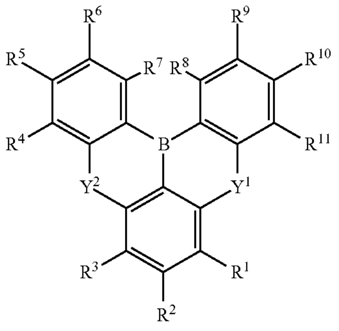

14 Claims, 1 Drawing Sheet

(51) Int. Cl.
*C07F 5/02* (2006.01)
*H10K 50/11* (2023.01)
*H10K 85/60* (2023.01)

(52) U.S. Cl.
CPC ...... *C09K 2211/1018* (2013.01); *H10K 50/11* (2023.02)

(56) References Cited

FOREIGN PATENT DOCUMENTS

| | | | |
|---|---|---|---|
| CN | 112028918 | A | 12/2020 |
| JP | 2020-004947 | A | 1/2020 |
| KR | 10-2016-0119683 | A | 10/2016 |
| KR | 10-2020-0070141 | A | 6/2020 |
| KR | 10-2020-0111620 | A | 9/2020 |
| KR | 10-2021-0006554 | A | 1/2021 |
| WO | 2015102118 | A1 | 7/2015 |
| WO | 2019035268 | A1 | 2/2019 |
| WO | 2020045681 | A1 | 3/2020 |
| WO | 2020/130456 | A1 | 6/2020 |
| WO | 2021/074096 | A1 | 4/2021 |

OTHER PUBLICATIONS

International Search Report and Search Opinion iand English translation n PCT/JP2021/010738, mailed Sep. 23, 2021.
Karthik et al., "Highly Efficient Blue Thermally Activated Delayed Fluorescence Organic Light Emitting Diodes Based on Tercarbazole Donor and Boron Acceptor Dyads", Journal of Materials Chemistry C, 2019, vol. 8, No. 7, pp. 2272-2279.
Takuyi Hatakeyama et al., "Ultrapure Blue Thermally Activated Delayed Fluorescence Molecules: Efficient HOMO-LUMO Separation by the Multiple Resonance Effect", Adv. Mater. 2016, 28, 2777-2781.
Xiao Liang et al., "Peripheral Amplification of Multi-Resonance Induced Thermally Activated Delayed Fluorescence for Highly Efficient OLEDs", Angew. Chem. Int. Ed. 2018, 57, 11316-11320.
Office Action dated Oct. 31, 2024 issued in the corresponding Chinese patent application No. 202180022015.6 with its English Machine Translation.
Office Action dated Apr. 8, 2025 issued in the corresponding Japanese patent application No. 2022-508396 with its English Machine Translation.
Office Action issued in Chinese Patent Application No. CN202180022015.6, mailed Jul. 1, 2025, with English Translation.
Office Action issued in Korean Patent Application No. KR 10-2022-7032809, mailed Sep. 1, 2025, with English translation.

* cited by examiner

COMPOUND, LIGHT-EMITTING MATERIAL, AND ORGANIC LIGHT-EMITTING DEVICE

TECHNICAL FIELD

The present invention relates to a compound having good light-emitting characteristics. Also the present invention relates to a light-emitting material and an organic light-emitting device using the compound.

BACKGROUND ART

Studies fix enhancing the light emission efficiency of organic light-emitting devices such as organic light-emitting diodes (OLED) are being made actively.

For example, NPL 1 describes that, by using a boron compound having a structure of 5,9-diphenyl-5H,9H[1,4]benzazaborino[2,3,4-kl]phenazaborine (DABNA-1), thermally activated delayed fluorescence (TADF) in a reverse intersystem crossing process can be expressed and light emission having a narrow full-width at half-maximum and a high color purity can be realized. Such light emission can attain a high emission efficiency and is useful in applications aspiring to displays.

NPLs 1 and 2 describe that, by modifying DABNA-1, the energy level of a highest occupied molecular orbital (HOMO) and a lowest unoccupied molecular orbital (LUMO) can be controlled, and by promoting a fluorescence emission process and a reverse intersystem crossing process that contribute toward light emission, an electroluminescence quantum yield can be improved. These documents report that an emission quantum yield can be improved by inserting a substituent into DABNA-1 but the emission from the substituted DABNA-1 is on a longer wavelength side than that from the unsubstituted DABNA-1.

CITATION LIST

Non-Patent Literature

NPL 1: Adv. Mater. 2016, 28, 2777-2781
NPL 2: Angew. Chem. Int. Ed. 2018, 57, 11316-11320

SUMMARY OF INVENTION

Technical Problem

As described in NPLs 1 and 2, molecular modification of a compound that expresses a multiple resonance effect like DABNA-1 is useful as a method for improving various physical data that are required for light-emitting materials for organic light-emitting devices. However, such modification expands a conjugated system and therefore makes the emission wavelength move toward a longer wavelength range. Consequently, the method has a problem in that a light-emitting material capable of emitting light in a blue region that is required to be developed could not be provided as intended.

In view of the above problems of the prior art, the present inventors have assiduously promoted intensive studies for the purpose of providing a derivative capable of emitting light in a shorter wavelength range than a compound that expresses a multiple resonance effect, and a derivative having more excellent emission characteristics than a compound that expresses a multiple resonance effect.

Solution to Problem

As a result of having advanced assiduous studies, the present inventors have surprisingly found that, when a specific substituent is introduced into a compound that expresses a multiple resonance effect, at a specific position, a derivative capable of emitting light in a short wavelength range and a derivative having improved emission characteristics can be obtained. The invention has been proposed on the basis of these findings, and has the following constitution.

[1] A compound represented by the following general formula (1),

General Formula (1)

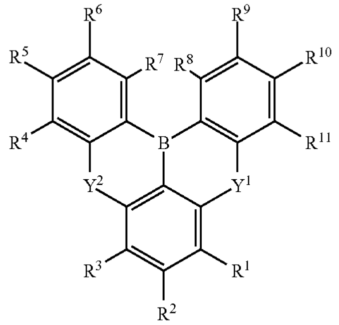

wherein:

$Y^1$ represents N—$R^A$, $Y^2$ represents O, S, C═O or N—$R^A$, $R^A$ each independently represents a substituted or unsubstituted aryl group, or a substituted or unsubstituted heteroaryl group, $R^1$ to $R^{11}$ each independently represent a hydrogen atom or a substituent, $R^1$ and $R^2$, $R^2$ and $R^3$, $R^4$ and $R^5$, $R^5$ and $R^6$, $R^6$ and $R^7$, $R^7$ and $R^8$, $R^8$ and $R^9$, $R^9$ and $R^{10}$, $R^{10}$ and $R^{11}$, $R^A$ and $R^4$, and $R^A$ and $R^{11}$ each can bond to each other to form a cyclic structure, provided that at least one of $R^1$, $R^2$ and $R^3$ is a group represented by the following general formula (2), General Formula (2)

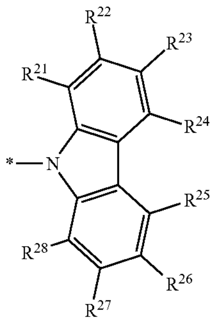

wherein $R^{21}$ to $R^{28}$ each independently represent a hydrogen atom or a substituent, $R^{21}$ and $R^{22}$, $R^{22}$ and $R^{23}$, $R^{23}$ and $R^{24}$, $R^{25}$ and $R^{26}$, $R^{26}$ and $R^{27}$, and $R^{27}$ and $R^{28}$ each can bond to each other to form a cyclic structure, provided that at least one of $R^{21}$ to $R^{28}$ is a substituted or unsubstituted aryl group or a substituted or unsubstituted heteroaryl group, and * indicates a bonding position.

[2] The compound according to [1], wherein $Y^2$ is N—$R^A$.

[3] The compound according to [1] or [2], wherein $R^7$ and $R^8$ are both hydrogen atoms.

[4] The compound according to any one of [1] to [3], wherein $R^A$ is each independently a substituted or unsubstituted aryl group.

[5] The compound according to any one of [1] to [4], wherein $R^1$ to $R^{11}$ each are independently a hydrogen atom, a substituted or unsubstituted alkyl group, or a substituted or unsubstituted aryl group.

[6] The compound according to any one of [1] to [5], wherein $R^5$ and $R^{10}$ each are independently a substituted or unsubstituted aryl group, or a substituted or unsubstituted alkyl group.

[7] The compound according to any one of [1] to [6], wherein $R^6$ and $R^9$ each are independently a substituted or unsubstituted aryl group, or a substituted or unsubstituted alkyl group.

[8] The compound according to any one of [1] to [7], wherein $R^2$ is a group represented by the general formula (2).

[9] The compound according to any one of [1] to [8], wherein $R^{21}$ to $R^{28}$ in the general formula (2) each are independently a hydrogen atom, a substituted or unsubstituted aryl group, or a substituted or unsubstituted heteroaryl group.

[10] The compound according to [9], wherein at least one of $R^{23}$ and $R^{26}$ in the general formula (2) is a substituted or unsubstituted aryl group.

[11] The compound according to [10], wherein $R^{23}$ and $R^{26}$ in the general formula (2) each are independently a substituted or unsubstituted aryl group.

[12] The compound according to [1], having any of the following structures,

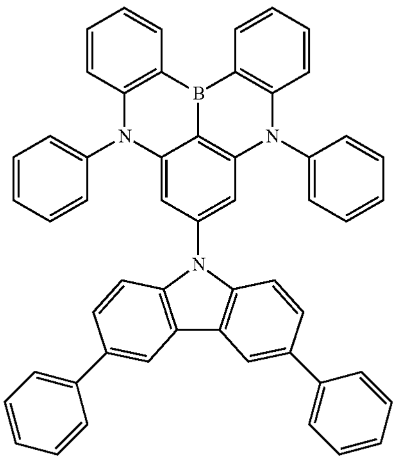

-continued

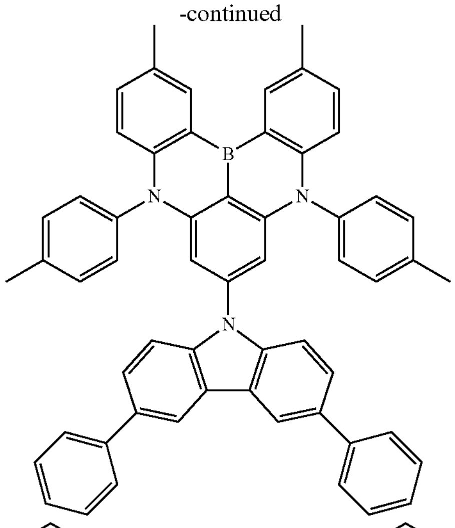

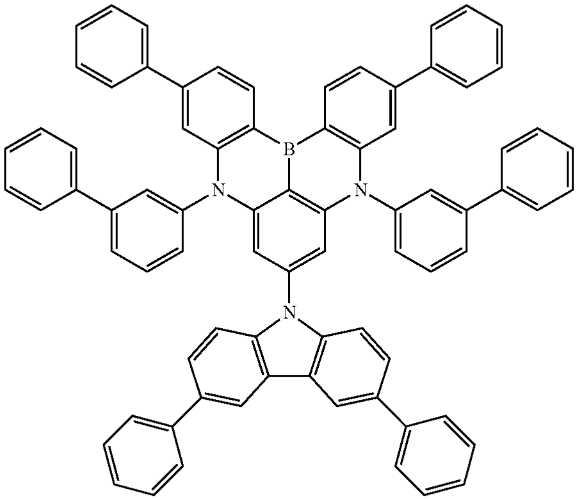

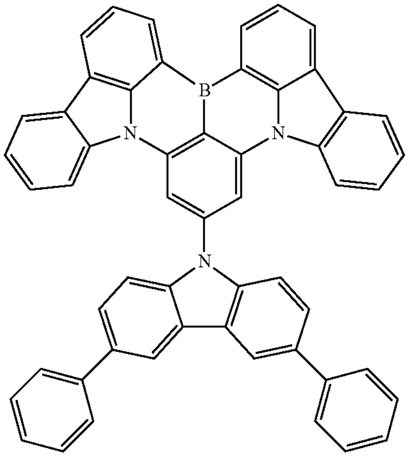

[13] A light-emitting material containing a compound of any one of [1] to [12].

[14] An organic light-emitting device containing a compound of any one of [1] to [12].

[15] The organic light-emitting device according to [14], wherein the device has a layer that contains the above compound, and the layer also contains a host material.

[16] The organic light-emitting device according to [14], wherein the device has a layer that contains the above compound, and the layer also contains a light-emitting material having a structure that differs from that of the above compound.

[17] The organic light-emitting device according to any one of [14] to [16], wherein among the materials contained in the device, the amount of light emission from the compound is the maximum.

[18] The organic light-emitting device according to [16], wherein the amount of light emission from the light-emitting material is larger than the amount of light emission from the above compound.

[19] The organic light-emitting device according to any one of [14] to [18], which is an organic light-emitting diode (OLED).

[20] The organic light-emitting device according to any one of [14] to [19], which emits delayed fluorescence.

[21] A compound represented by the following general formula (A),

General Formula (A)

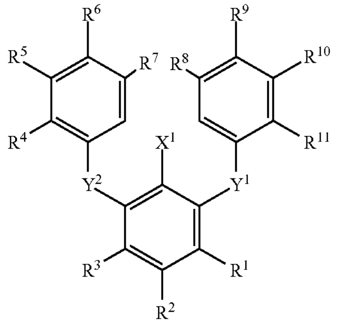

wherein:

$X^1$ represents a halogen atom, $Y^1$ represents N—$R^A$, $Y^2$ represents O, S, C═O or N—$R^A$, $R^A$ each independently represents a substituted or unsubstituted aryl group, or a substituted or unsubstituted heteroaryl group, $R^1$ to $R^{11}$ each independently represent a hydrogen atom or a substituent, $R^1$ and $R^2$, $R^2$ and $R^3$, $R^4$ and $R^5$, $R^5$ and $R^6$, $R^6$ and $R^7$, $R^8$ and $R^9$, $R^9$ and $R^{10}$, $R^{10}$ and $R^{11}$, $R^A$ and $R^4$, and $R^A$ and $R^{11}$ each can bond to each other to form a cyclic structure, provided that at least one of $R^1$, $R^2$ and $R^3$ is a group represented by the following general formula (2), General Formula (2)

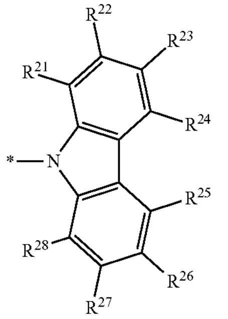

wherein $R^{21}$ to $R^{28}$ each independently represent a hydrogen atom or a substituent, $R^{21}$ and $R^{22}$, $R^{22}$ and $R^{23}$, $R^{23}$ and $R^{24}$, $R^{25}$ and $R^{26}$, $R^{26}$ and $R^{27}$, and $R^{27}$ and $R^{28}$ each can bond to each other to form a cyclic structure, provided that at least one of $R^{21}$ to $R^{28}$ is a substituted or unsubstituted aryl group or a substituted or unsubstituted heteroaryl group, and * indicates a bonding position.

Advantageous Effects of Invention

According to the present invention, there can be provided a compound capable of emitting light in a short wavelength region while expressing a multiple resonance effect, and a compound having good light emission characteristics. Also according to the present invention, there can be provided an organic light-emitting device that exhibits excellent light emission characteristics and can emit light in a short wavelength region.

DESCRIPTION OF EMBODIMENTS

Figure 1:
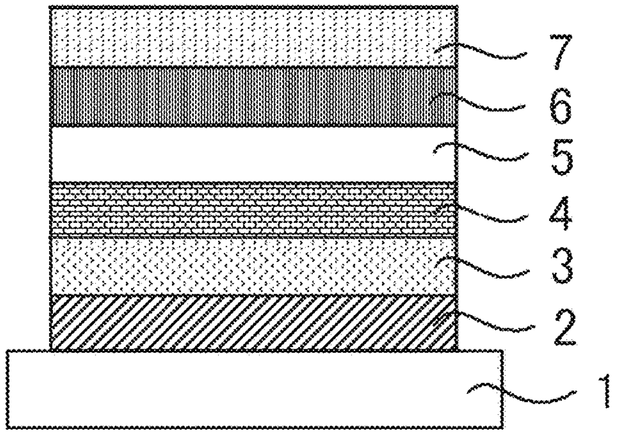
FIG. 1 This is a schematic cross-sectional view showing an example of a layer configuration of an organic electroluminescent device.

The contents of the invention will be described in detail below. The constitutional elements may be described below with reference to representative embodiments and specific examples of the invention, but the invention is not limited to the embodiments and the examples. In the description herein, a numerical range expressed as "to" means a range that includes the numerical values described before and after "to" as the upper limit and the lower limit.

[Compound Represented by General Formula (1)]

The present invention provides a compound represented by the following general formula (1).

General Formula (1)

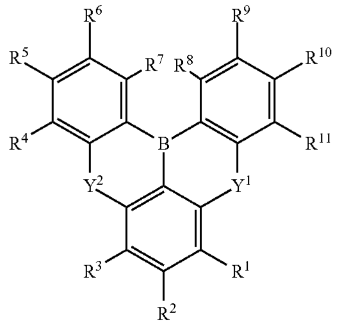

In the general formula (1), $Y^1$ represents N—$R^A$, $Y^2$ represents O, S, C═O or N—$R^A$. When $Y^2$ is N—$R^A$, $Y^1$ and $Y^2$ can be the same or different, but are preferably the same.

$R^7$ and $R^8$ in the general formula (1) can bond to each other to form a cyclic structure. In that case, $R^7$ and $R^8$ bond to each other to form a linking group represented by —$Y^3$—. $Y^3$ is preferably O, S, C═O or N—$R^A$. In one embodiment of the invention, N—$R^A$ can be selected for $Y^3$. In another embodiment of the invention, O or S can be selected for $Y^3$. In still another embodiment of the invention, C═O can be selected for $Y^3$.

In one embodiment of the invention, $Y^1$ and $Y^2$ each are independently N—$R^A$, and $R^7$ and $R^8$ are hydrogen atoms. In that case, preferably, $Y^1$ and $Y^2$ are the same. In another embodiment of the invention, $Y^2$ is O, and $R^7$ and $R^8$ are hydrogen atoms. In another embodiment of the invention, $Y^2$ is S, and $R^7$ and $R^8$ are hydrogen atoms. In another embodiment of the invention, $Y^2$ is C═O, and $R^7$ and $R^8$ are hydrogen atoms.

In another embodiment of the invention, $R^7$ and $R^8$ bond to each other to form a linking group represented by —$Y^3$—, and $Y^1$ to $Y^3$ each are independently N—$R^A$. In one embodiment of that case, any two of $Y^1$ to $Y^3$ are the same and the other one is different. In another embodiment, $Y^1$ to $Y^3$ are all the same. In still another embodiment of the invention, $Y^1$ and $Y^2$ each are independently N—$R^A$, and $Y^3$ is O. In that case, preferably, $Y^1$ and $Y^2$ are the same. In another embodiment of the invention, $Y^1$ and $Y^2$ each are independently N—$R^A$, and $Y^3$ is S. In that case, preferably, $Y^1$ and $Y^2$ are the same. In another embodiment of the invention, $Y^1$ and $Y^2$ each are independently N—$R^A$, and $Y^3$ is C═O. In that case, preferably, $Y^1$ and $Y^2$ are the same. In another embodiment of the invention, $Y^1$ and $Y^3$ each are independently N—$R^A$, and $Y^2$ is O. In that case, preferably, $Y^1$ and $Y^3$ are the same. In another embodiment of the invention, $Y^1$ and $Y^3$ each are independently N—$R^A$, and $Y^2$ is S. In that case, preferably, $Y^1$ and $Y^3$ are the same. In another embodiment of the invention, $Y^1$ and $Y^3$ each are independently N—$R^A$, and $Y^2$ is C═O. In that case, preferably, $Y^1$ and $Y^3$ are the same.

$R^A$ in N—$R^A$ each independently represents a substituted or unsubstituted aryl group, or a substituted or unsubstituted heteroaryl group. Preferably, $R^A$ is each independently a substituted or unsubstituted aryl group. Examples of the substituent of the aryl group and the heteroaryl group as referred to herein include a substituted or unsubstituted alkyl group, a substituted or unsubstituted aryl group, a substituted or unsubstituted heteroaryl group, a substituted or unsubstituted alkoxy group, a substituted or unsubstituted aryloxy group, and a substituted or unsubstituted heteroaryloxy group. Preferably, the substituent is a substituted or unsubstituted alkyl group, a substituted or unsubstituted aryl group, or a substituted or unsubstituted heteroaryl group, more preferably a substituted or unsubstituted alkyl group, or a substituted or unsubstituted aryl group. For example, a substituted or unsubstituted alkyl group can be preferably selected. The substituent of the alkyl group, the aryl group, the heteroaryl group, an alkoxy group, the aryloxy group and the heteroaryloxy group includes an alkyl group, an aryl group, a heteroaryl group, an alkoxy group, an aryloxy group and a heteroaryloxy group. In the case where two or more substituents exist each in the aryl group and the heteroaryl group that $R^A$ represents, the substituents may bond to each other to form a cyclic structure. In that case, the cyclic structure can be an aromatic ring or a non-aromatic ring. It can also be a hydrocarbon ring, or a hetero ring. For example, a benzene ring can be exemplified. In the case where two or more substituent exist each in the aryl group and the heteroaryl group that $R^A$ represents, the substituents may not bond to each other. In one embodiment of the invention, the substituent existing in the aryl group and the heteroaryl group that $R^A$ represents does not bond to at least one of $R^1$ to $R^{11}$ in the general formula (1) to form a cyclic structure. In another embodiment of the invention, the substituent existing in the aryl group and the heteroaryl group that $R^A$ represents bonds to at least one of $R^4$ and $R^{11}$ in the general formula (1) to form a cyclic structure. In still another embodiment of the invention, $Y^1$ is N—$R^A$, and the substituent existing in the aryl group and the heteroaryl group that $R^A$ represents bonds to $R^{11}$ in the general formula (1) to form a cyclic structure (preferably, $R^{11}$ is a single bond and bonds to the aryl ring or the heteroaryl ring of $R^A$), or $Y^2$ is N—$R^A$, and the substituent existing in the aryl group and the heteroaryl group that $R^A$ represents bonds to $R^4$ in the general formula (1) to form a cyclic structure (preferably, $R^{11}$ is a single bond and bonds to the aryl ring or the heteroaryl ring of $R^A$).

Hereinunder specific examples of N—$R^A$ are shown, but N—$R^A$ employable in the present invention should not be limitatively interpreted by these specific examples. * indicates a bonding position.

B1

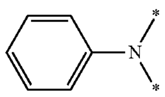

B2

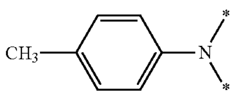

B3

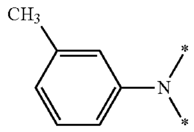

B4

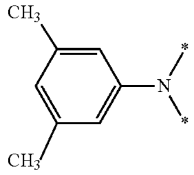

B5

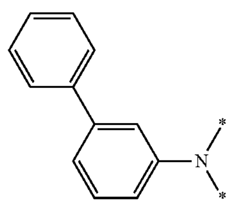

B6

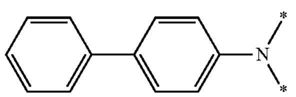

In the general formula (1), $R^1$ to $R^{11}$ each independently represent a hydrogen atom or a substituent.

Among these, at least one of $R^1$, $R^2$ and $R^3$ is a group represented by the following general formula (2). The compound represented by the general formula (1) includes a compound to which a group represented by the general formula (2) bonds, and the compound emits light having a short wavelength. By substituting the hydrogen atom in the compound of the general formula (1) with a group represented by the general formula (2), the emission wavelength from the compound preferably shortens by 5 nm or more, more preferably by 10 nm or more, even more preferably by 15 nm or more (regarding the measurement condition, reference can be made to Example 1 and Comparative Example 1 given hereinunder). Also preferably, the emission maximum wavelength of the compound of the general formula (1) is 460 nm or less, more preferably 455 nm or less, even more preferably 450 nm or less.

The compound represented by the general formula (1) includes a compound having an improved emission efficiency owing to the group of the general formula (2) bonding to the compound. For example, the photoluminescence quantum yield (PLQY) of a thin film of PYD2Cz doped with a compound of the general formula (1) in a concentration of 1% by weight, as measured by irradiating the thin film with 300-nm excitation light, is preferably increased by 2% or more by bonding of the group of the general formula (2) to the compound, more preferably by 3% or more, even more preferably 3.5% or more. Regarding the measurement condition for the emission efficiency, for example, reference can be made to the measurement condition in Example 1 and Comparative Example 1 given hereinunder.

The compound represented by the general formula (1) includes a compound having a narrowed full-width at half-maximum owing to the group of the general formula (2) bonding to the compound. For example, the full-width at half-maximum of the visible region emission peak in the emission spectrum of a thin film of PYD2Cz doped with a compound of the general formula (1) in a concentration of 1% by weight, as measured by irradiating the thin film with 300-nm excitation light, is preferably narrowed by 3 nm or more by bonding of the group of the general formula (2) to the compound, more preferably by 5 nm or more, even more preferably 7 nm or more.

Regarding the measurement condition for the full-width at half-maximum, for example, reference can be made to the measurement condition in Example 1 and Comparative Example 1 given hereinunder.

In the compound represented by the general formula (1), only one of $R^1$, $R^2$ and $R^3$ can be a group represented by the general formula (2), and in that case, preferably, $R^2$ is a group represented by the general formula (2). Also, $R^1$ can be a group represented by the general formula (2), or $R^3$ can be a group represented by the general formula (2). In the case where two or three of $R^1$, $R^2$ and $R^3$ each are a group represented by the general formula (2), plural groups of the general formula (2) can be the same as or different from each other. Preferably, they are the same. In the case, the two can be $R^1$ and $R^2$, or can be $R^2$ and $R^3$, or can be $R^1$ and $R^3$. $R^1$ to $R^3$ that are not a group represented by the general formula (2) each are preferably a hydrogen atom, a substituted or unsubstituted alkyl group, a substituted or unsubstituted aryl group, or a substituted or unsubstituted heteroaryl group, more preferably a hydrogen atom, or a substituted or unsubstituted alkyl group. Also preferably, all $R^1$ to $R^3$ that are not a group represented by the general formula (2) are hydrogen atoms. Regarding the description and the preferred range of the substituted or unsubstituted alkyl group, the substituted or unsubstituted aryl group and the substituted or unsubstituted heteroaryl group, reference can be made to the corresponding description relating to $R^A$.

General Formula (2)

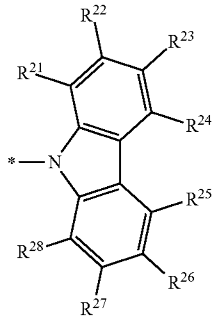

In the general formula (2), * indicates a bonding position. $R^{21}$ to $R^{25}$ each independently represent a hydrogen atom or a substituent, at least one of $R^{21}$ to $R^{28}$ is a substituted or unsubstituted aryl group or a substituted or unsubstituted heteroaryl group, and is preferably a substituted or unsubstituted aryl group. Regarding the description and the preferred range of the substituted or unsubstituted aryl group and the substituted or unsubstituted heteroaryl group, reference can be made to the corresponding description relating to $R^A$.

Among $R^{21}$ to $R^{28}$, the number of a substituted or unsubstituted aryl group or a substituted or unsubstituted heteroaryl group is any of 1 to 8, preferably any of 1 to 6, more preferably 1 to 4. For example, one is the group. Preferably, two are the groups. In the case where two are the groups, they may be the same as or different from each other, but are preferably the same. Among $R^{21}$ to $R^{28}$, preferably, at least one of $R^{22}$, $R^{23}$, $R^{24}$, $R^{25}$, $R^{26}$ and $R^{27}$ is a substituted or unsubstituted aryl group, or a substituted or unsubstituted heteroaryl group, more preferably, at least one of $R^{22}$, $R^{23}$, $R^{26}$ and $R^{27}$ is a substituted or unsubstituted aryl group, or a substituted or unsubstituted heteroaryl group, even more preferably, at least one of $R^{23}$ and $R^{26}$ is a substituted or unsubstituted aryl group, or a substituted or unsubstituted heteroaryl group. Both $R^{23}$ and $R^{26}$ can be any of a substituted or unsubstituted aryl group, or a substituted or unsubstituted heteroaryl group.

Among $R^{21}$ to $R^{28}$, those that are neither a substituted or unsubstituted aryl group nor a substituted or unsubstituted heteroaryl group are preferably any of a hydrogen atom or a substituted or unsubstituted alkyl group. For example, among $R^{21}$ to $R^{28}$, those that are neither a substituted or unsubstituted aryl group nor a substituted or unsubstituted heteroaryl group can be all hydrogen atoms. One to four of those can be a substituted or unsubstituted alkyl group, or one or two can be a substituted or unsubstituted alkyl group. Examples of the substituent for the alkyl group include an aryl group. Also the alkyl group is preferably an unsubstituted one.

In the general formula (1), $R^4$ to $R^6$ and $R^9$ to $R^{11}$ each are preferably a hydrogen atom, a substituted or unsubstituted alkyl group, a substituted or unsubstituted aryl group or a substituted or unsubstituted heteroaryl group, more preferably a hydrogen atom, a substituted or unsubstituted alkyl group or a substituted or unsubstituted aryl group. $R^4$ to $R^6$ and $R^9$ to $R^{11}$ can be all hydrogen atoms. Three to five of $R^4$ to $R^6$ and $R^9$ to $R^{11}$ can be hydrogen atoms. Zero to two of $R^4$ to $R^6$ and $R^9$ to $R^{11}$ can be hydrogen atoms. In one embodiment of the invention, at least one of $R^5$ and $R^{10}$ is a substituent, and more preferably the two are substituents. In one embodiment of the invention, at least one of $R^6$ and $R^9$ is a substituent, more preferably the two are substituents. In one example, $R^5$ and $R^{10}$ each are independently a substituted or unsubstituted alkyl group or a substituted or unsubstituted aryl group, and $R^4$, $R^6$, $R^9$ and $R^{11}$ are hydrogen atoms, and in another example, $R^{11}$ and $R^9$ each are independently a substituted or unsubstituted alkyl group or a substituted or unsubstituted aryl group, and $R^4$, $R^5$, $R^{10}$ and $R^{11}$ are hydrogen atoms.

In the general formula (1), R1 and R2, R2 and R3, R4 and R5, R5 and R6, R6 and R7, R7 and R8, R8 and R9, R9 and R10, R10 and R11, RA and R4, and RA and R11 each can bond to each other to form a cyclic structure. In the general formula (2), R21 and R22, R22 and R23, R23 and R24, R25 and R26, R26 and R27, and R27 and R28 each can bond to each other to form a cyclic structure. Preferably, none of these combinations bind to each other to form a cyclic structure. In the case where a cyclic structure is formed, the cyclic structure to be formed can be an aromatic ring or a non-aromatic ring. The structure can also be a hydrocarbon ring, or a hetero ring. For example, a benzene ring can be one example.

Specific examples of the substituent for $R^1$ to $R^{11}$ are shown below. * indicates a bonding position. Among these, G2 to G5 are specific examples of $R^{21}$ to $R^{28}$ each being a substituted or unsubstituted aryl group. $R^1$ to $R^{11}$ and $R^{21}$ to $R^{28}$ employable in the present invention should not be limitatively interpreted by these specific examples.

G1

$CH_3$—*

G2

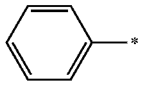

G3

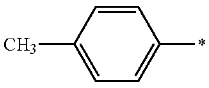

G4

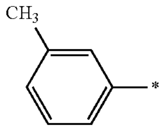

G5

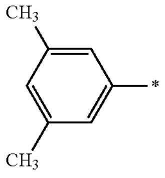

In a preferred group 1 of the invention, $R^A$ in the general formula (1) is each independently a substituted or unsubstituted aryl group, or a substituted or unsubstituted heteroaryl group, $R^1$ to $R^{11}$ each are independently a hydrogen atom, a substituted or unsubstituted alkyl group, a substituted or unsubstituted aryl group, or a substituted or unsubstituted heteroaryl group, at least one of $R^{21}$ to $R^{28}$ in the general formula (2) is a substituted or unsubstituted aryl group, or a substituted or unsubstituted heteroaryl group.

In a preferred group 2 of the invention, $R^A$ in the general formula (1) is each independently a substituted or unsubstituted group, $R^1$ to $R^{11}$ each are independently a hydrogen atom, a substituted or unsubstituted alkyl group, a substituted or unsubstituted aryl group, or a substituted or unsubstituted heteroaryl group, at least one of $R^{21}$ to $R^{28}$ in the general formula (2) is a substituted or unsubstituted aryl group.

In a preferred group 3 of the invention, $R^A$ in the general formula (1) is each independently a substituted or unsubstituted aryl group, $R^1$ to $R^{11}$ each are independently a hydrogen atom, a substituted or unsubstituted alkyl group, or a substituted or unsubstituted aryl group, at least one of $R^{21}$ to $R^{28}$ in the general formula (2) is a substituted or unsubstituted aryl group.

In the preferred groups 1 to 3, a group where $Y^2$ is N—$R^A$ is referred to as preferred groups 4 to 6, respectively.

In the preferred groups 1 to 3, a group where $Y^2$ is O is referred to as preferred groups 7 to 9, respectively.

In the preferred groups 1 to 3, a group where $Y^2$ is S is referred to as preferred groups 10 to 12, respectively.

In the preferred groups 1 to 3, a group where $Y^2$ is C═O is referred to as preferred groups 3 to 15, respectively.

In the preferred groups 1 to 15, a group where $R^7$ and $R^8$ are hydrogen atoms is referred to as preferred groups 16 to 30, respectively.

In the preferred groups 1 to 15, a group where $Y^3$ is N—$R^A$ is referred to as preferred groups 31 to 45, respectively.

In the preferred groups 1 to 15, a group where $Y^3$ is O is referred to as preferred groups 46 to 60, respectively.

In the preferred groups 1 to 15, a group where $Y^3$ is S is referred to as preferred groups 61 to 75, respectively.

In the preferred groups 1 to 15, a group where $Y^3$ is C═O is referred to as preferred groups 76 to 90, respectively.

In the preferred groups 1 to 90, a group where $R^A$ is an unsubstituted aryl group is referred to as preferred groups 91 to 180, respectively.

In the preferred groups 1 to 90, a group where $R^A$ is an aryl group substituted with a substituted or unsubstituted alkyl group is referred to as preferred groups 181 to 270, respectively.

In the preferred groups 1 to 90, a group where $R^A$ is an aryl group substituted with a substituted or unsubstituted aryl group is referred to as preferred groups 271 to 360, respectively.

In the preferred groups 1 to 360, a group where $R^1$ is a group represented by the general formula (2) is referred to as preferred groups 361 to 720, respectively.

In the preferred groups 1 to 360, a group where $R^2$ is a group represented by the general formula (2) is referred to as preferred groups 721 to 1080, respectively.

In the preferred groups 1 to 360, a group where $R^3$ is a group represented by the general formula (2) is referred to as preferred groups 1081 to 1440, respectively.

In the preferred groups 1 to 1440, a group where $R^{21}$ to $R^{28}$ each are independently a hydrogen atom, a substituted or unsubstituted alkyl group, a substituted or unsubstituted aryl group, or a substituted or unsubstituted heteroaryl group is referred to as preferred groups 1441 to 2880, respectively.

In the preferred groups 1 to 1440, a group where $R^{21}$ to $R^{28}$ each are independently a hydrogen atom, or a substituted or unsubstituted aryl group is referred to as preferred groups 2881 to 4320, respectively.

In the preferred groups 1 to 4320, a group where $R^4$ to $R^{11}$ each are independently a hydrogen atom, or a substituted or unsubstituted alkyl group is referred to as preferred groups 4321 to 8640, respectively.

In the preferred groups 1 to 4320, a group where $R^4$ to $R^{11}$ each are independently a hydrogen atom, or a substituted or unsubstituted aryl group is referred to as preferred groups 8641 to 12960, respectively.

In the preferred groups 1 to 12960, a group where $R^1$ and $R^2$, $R^2$ and $R^3$, $R^4$ and $R^5$, $R^5$ and $R^6$, $R^6$ and $R^7$, $R^7$ and $R^8$, $R^8$ and $R^9$, $R^9$ and $R^{10}$, $R^{10}$ and $R^{11}$, $R^{21}$ and $R^{22}$, $R^{22}$ and $R^{23}$, $R^{23}$ and $R^{24}$, $R^{25}$ and $R^{26}$, $R^{26}$ and $R^{27}$, and $R^{27}$ and $R^{28}$ each do not bond to each other is referred to as preferred groups 12961 to 25920, respectively.

Among the compounds represented by the general formula (1), for example, compounds represented by the following general formula (3) are preferably employed.

General Formula (3)

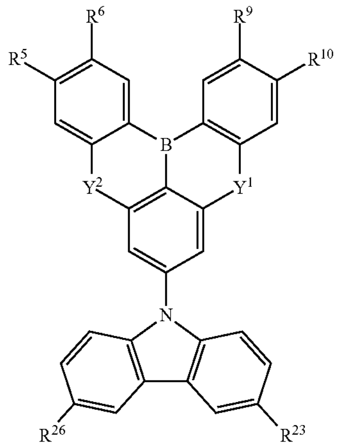

In the general formula (3), $Y^1$ represents N—$R^A$. $Y^2$ represents O, S, C═O or N—$R^A$. $R^A$ each independently represents a substituted or unsubstituted aryl group, or a substituted or unsubstituted heteroaryl group. $R^5$, $R^6$, $R^9$ and $R^{10}$ each independently represent a hydrogen atom or a substituent, and $R^5$ and $R^6$, and $R^9$ and $R^{10}$ each may bond to each other to form a cyclic structure. $R^{23}$ and $R^{26}$ each independently represent a substituted or unsubstituted aryl group, or a substituted or unsubstituted heteroaryl group.

For the description and the preferred range of $Y^1$, $Y^2$, $R^5$, $R^6$, $R^9$, $R^{10}$, $R^{23}$ and $R^{26}$ in the general formula (3), reference can be made to the corresponding description relating to the general formula (1).

In one embodiment of the invention, $R^5$ and $R^6$, and $R^9$ and $R^{10}$ each do not bond to each other. In one embodiment of the invention, $R^{23}$ and $R^{26}$ each are independently a substituted or unsubstituted aryl group, and preferably $R^{23}$ and $R^{26}$ are the same. In the present invention, preferably, $R^5$, $R^6$, $R^9$ and $R^{10}$ each are independently a hydrogen atom, a substituted or unsubstituted alkyl group or a substituted or an unsubstituted aryl group. In one embodiment of the invention, $R^5$, $R^6$, $R^9$ and $R^{10}$ are hydrogen atoms. In another embodiment of the invention, $R^5$ and $R^{10}$ each are a substituted or unsubstituted alkyl group, or a substituted or unsubstituted aryl group. In another embodiment of the invention, $R^6$ and $R^9$ each are a substituted or unsubstituted alkyl group, or a substituted or unsubstituted aryl group.

Regarding the molecular weight of the compound represented by the general formula (1), for example, in the case where the compound is intended to be used in an organic layer containing it and where the organic layer is formed according to a evaporation method, the molecular weight of the compound is preferably 1500 or less, more preferably 1200 or less, even more preferably 1000 or less, further more preferably 900 or less. The lower limit of the molecular weight is the molecular weight of the smallest compound represented by the general formula (1).

The compound represented by the general formula (1) can be used as a film formed according to a coating method irrespective of the molecular weight thereof. According to a coating method, even a compound having a relatively large molecular weight can be formed into a film.

By applying the present invention, a compound containing plural structures represented by the general formula (1) can be prepared. Such a compound is considered to be used as, for example, a charge transporting material.

For example, a polymerizable group is previously incorporated into the structure represented by the general formula (1), and the polymerizable group is polymerized to give a polymer. Specifically, a monomer having a polymerizable functional group in any of $R^1$ to $R^{11}$ and $R^{21}$ to $R^{28}$ in the general formula (1) is prepared, and this is homopolymerized, or is copolymerized with any other monomer to give a polymer having a repeating unit. Also, compounds each having a structure represented by the general formula (1) can be coupled to give a dimer or a trimer. In the present invention compounds not containing a repeating unit are also preferably employed.

In some embodiments, the compound represented by the general formula (1) does not contain a metal atom. In some embodiments, the compound represented by the general formula (1) is composed of atoms alone of a hydrogen atom, a carbon atom, a boron atom and a nitrogen atom. In some embodiments, the compound represented by the general formula (1) is composed of atoms alone selected from the group consisting of a hydrogen atom, a carbon atom, a boron atom, a nitrogen atom and an oxygen atom. In some embodiments, the compound represented by the general formula (1) is composed of atoms alone selected from the group consisting of a hydrogen atom, a carbon atom, a boron atom, a nitrogen atom and a sulfur atom. In some embodiments, the compound represented by the general formula (1) is composed of atoms alone selected from the group consisting of a hydrogen atom, a carbon atom, a boron atom, a nitrogen atom and, an oxygen atom, a sulfur atom and a silicon atom. In some embodiments, the compound represented by the general formula (1) does not contain a cyano group. In some embodiments, the compound represented by the general formula (1) does not contain a diarylamino group (provided that the two amino groups constituting the diarylamino group do not bond to each other via a single bond or a linking group to form a cyclic structure).

Specific examples of the compound represented by the general formula (3) are listed in the following table. Of the compounds 1 to 3 in the table, the structures are shown below. The scope of the compound of the present invention should not be limitatively interpreted by these specific examples.

Compound 1

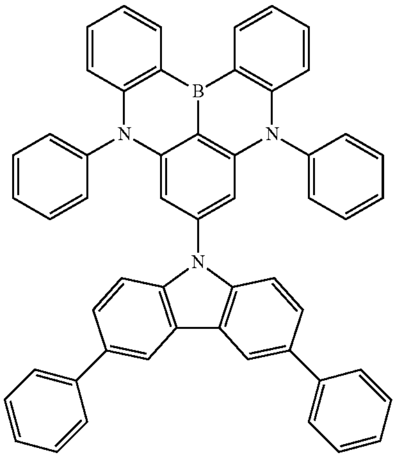

Compound 2

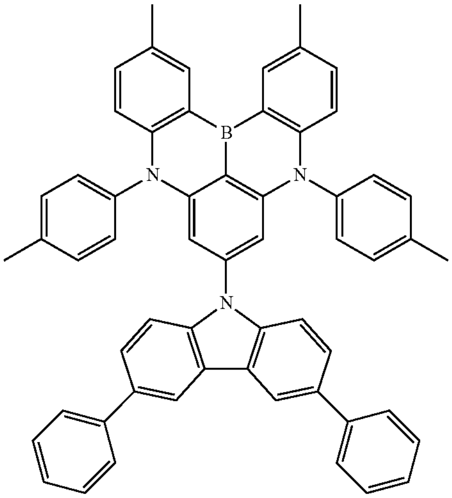

Compound 3

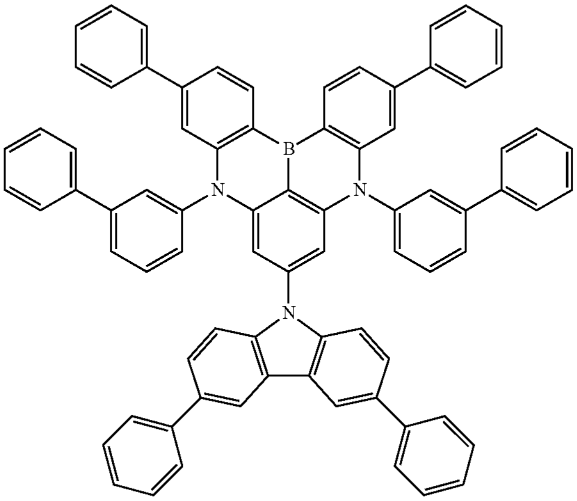

TABLE 1

| No. | $Y^1$ | $Y^2$ | $R^5$ | $R^6$ | $R^9$ | $R^{10}$ | $R^{23}$ | $R^{26}$ |
|---|---|---|---|---|---|---|---|---|
| 1 | B1 | B1 | H | H | H | H | G2 | G2 |
| 2 | B2 | B2 | H | G1 | G1 | H | G2 | G2 |
| 3 | B5 | B5 | G2 | H | H | G2 | G2 | G2 |
| 4 | B1 | B1 | H | G1 | G1 | H | G2 | G2 |
| 5 | B1 | B1 | H | G2 | G2 | H | G2 | G2 |
| 6 | B1 | B1 | H | G3 | G3 | H | G2 | G2 |
| 7 | B1 | B1 | H | G4 | G4 | H | G2 | G2 |
| 8 | B1 | B1 | H | G5 | G5 | H | G2 | G2 |
| 9 | B1 | B1 | G1 | H | H | G1 | G2 | G2 |
| 10 | B1 | B1 | G2 | H | H | G2 | G2 | G2 |
| 11 | B1 | B1 | G3 | H | H | G3 | G2 | G2 |
| 12 | B1 | B1 | G4 | H | H | G4 | G2 | G2 |
| 13 | B1 | B1 | G5 | H | H | G5 | G2 | G2 |
| 14 | B1 | B1 | G1 | G1 | G1 | G1 | G2 | G2 |
| 15 | B1 | B1 | H | G1 | G1 | H | G3 | G3 |
| 16 | B1 | B1 | H | G2 | G2 | H | G3 | G3 |
| 17 | B1 | B1 | H | G3 | G3 | H | G3 | G3 |
| 18 | B1 | B1 | H | G4 | G4 | H | G3 | G3 |
| 19 | B1 | B1 | H | G5 | G5 | H | G3 | G3 |
| 20 | B1 | B1 | G1 | H | H | G1 | G3 | G3 |
| 21 | B1 | B1 | G2 | H | H | G2 | G3 | G3 |
| 22 | B1 | B1 | G3 | H | H | G3 | G3 | G3 |
| 23 | B1 | B1 | G4 | H | H | G4 | G3 | G3 |
| 24 | B1 | B1 | G5 | H | H | G5 | G3 | G3 |
| 25 | B1 | B1 | G1 | G1 | G1 | G1 | G3 | G3 |
| 26 | B1 | B1 | H | G1 | G1 | H | G4 | G4 |
| 27 | B1 | B1 | H | G2 | G2 | H | G4 | G4 |
| 28 | B1 | B1 | H | G3 | G3 | H | G4 | G4 |
| 29 | B1 | B1 | H | G4 | G4 | H | G4 | G4 |
| 30 | B1 | B1 | H | G5 | G5 | H | G4 | G4 |
| 31 | B1 | B1 | G1 | H | H | G1 | G4 | G4 |
| 32 | B1 | B1 | G2 | H | H | G2 | G4 | G4 |
| 33 | B1 | B1 | G3 | H | H | G3 | G4 | G4 |
| 34 | B1 | B1 | G4 | H | H | G4 | G4 | G4 |
| 35 | B1 | B1 | G5 | H | H | G5 | G4 | G4 |
| 36 | B1 | B1 | G1 | G1 | G1 | G1 | G4 | G4 |
| 37 | B1 | B1 | H | G1 | G1 | H | G5 | G5 |
| 38 | B1 | B1 | H | G2 | G2 | H | G5 | G5 |
| 39 | B1 | B1 | H | G3 | G3 | H | G5 | G5 |
| 40 | B1 | B1 | H | G4 | G4 | H | G5 | G5 |
| 41 | B1 | B1 | H | G5 | G5 | H | G5 | G5 |
| 42 | B1 | B1 | G1 | H | H | G1 | G5 | G5 |
| 43 | B1 | B1 | G2 | H | H | G2 | G5 | G5 |
| 44 | B1 | B1 | G3 | H | H | G3 | G5 | G5 |
| 45 | B1 | B1 | G4 | H | H | G4 | G5 | G5 |
| 46 | B1 | B1 | G5 | H | H | G5 | G5 | G5 |
| 47 | B1 | B1 | G1 | G1 | G1 | G1 | G5 | G5 |
| 48 | B2 | B2 | H | H | H | H | G2 | G2 |
| 49 | B2 | B2 | H | G2 | G2 | H | G2 | G2 |
| 50 | B2 | B2 | H | G3 | G3 | H | G2 | G2 |
| 51 | B2 | B2 | H | G4 | G4 | H | G2 | G2 |
| 52 | B2 | B2 | H | G5 | G5 | H | G2 | G2 |
| 53 | B2 | B2 | G1 | H | H | G1 | G2 | G2 |
| 54 | B2 | B2 | G2 | H | H | G2 | G2 | G2 |
| 55 | B2 | B2 | G3 | H | H | G3 | G2 | G2 |
| 56 | B2 | B2 | G4 | H | H | G4 | G2 | G2 |
| 57 | B2 | B2 | G5 | H | H | G5 | G2 | G2 |
| 58 | B2 | B2 | G1 | G1 | G1 | G1 | G2 | G2 |
| 59 | B2 | B2 | H | G1 | G1 | H | G3 | G3 |
| 60 | B2 | B2 | H | G2 | G2 | H | G3 | G3 |
| 61 | B2 | B2 | H | G3 | G3 | H | G3 | G3 |
| 62 | B2 | B2 | H | G4 | G4 | H | G3 | G3 |
| 63 | B2 | B2 | H | G5 | G5 | H | G3 | G3 |
| 64 | B2 | B2 | G1 | H | H | G1 | G3 | G3 |
| 65 | B2 | B2 | G2 | H | H | G2 | G3 | G3 |
| 66 | B2 | B2 | G3 | H | H | G3 | G3 | G3 |
| 67 | B2 | B2 | G4 | H | H | G4 | G3 | G3 |
| 68 | B2 | B2 | G5 | H | H | G5 | G3 | G3 |
| 69 | B2 | B2 | G1 | G1 | G1 | G1 | G3 | G3 |
| 70 | B2 | B2 | H | G1 | G1 | H | G4 | G4 |
| 71 | B2 | B2 | H | G2 | G2 | H | G4 | G4 |
| 72 | B2 | B2 | H | G3 | G3 | H | G4 | G4 |
| 73 | B2 | B2 | H | G4 | G4 | H | G4 | G4 |
| 74 | B2 | B2 | H | G5 | G5 | H | G4 | G4 |
| 75 | B2 | B2 | G1 | H | H | G1 | G4 | G4 |
| 76 | B2 | B2 | G2 | H | H | G2 | G4 | G4 |
| 77 | B2 | B2 | G3 | H | H | G3 | G4 | G4 |
| 78 | B2 | B2 | G4 | H | H | G4 | G4 | G4 |

TABLE 1-continued

| No. | $Y^1$ | $Y^2$ | $R^5$ | $R^6$ | $R^9$ | $R^{10}$ | $R^{23}$ | $R^{26}$ |
|---|---|---|---|---|---|---|---|---|
| 79 | B2 | B2 | G5 | H | H | G5 | G4 | G4 |
| 80 | B2 | B2 | G1 | G1 | G1 | G1 | G4 | G4 |
| 81 | B2 | B2 | H | G1 | G1 | H | G5 | G5 |
| 82 | B2 | B2 | H | G2 | G2 | H | G5 | G5 |
| 83 | B2 | B2 | H | G3 | G3 | H | G5 | G5 |
| 84 | B2 | B2 | H | G4 | G4 | H | G5 | G5 |
| 85 | B2 | B2 | H | G5 | G5 | H | G5 | G5 |
| 86 | B2 | B2 | G1 | H | H | G1 | G5 | G5 |
| 87 | B2 | B2 | G2 | H | H | G2 | G5 | G5 |
| 88 | B2 | B2 | G3 | H | H | G3 | G5 | G5 |
| 89 | B2 | B2 | G4 | H | H | G4 | G5 | G5 |
| 90 | B2 | B2 | G5 | H | H | G5 | G5 | G5 |
| 91 | B2 | B2 | G1 | G1 | G1 | G1 | G5 | G5 |
| 92 | B3 | B3 | H | H | H | H | G2 | G2 |
| 93 | B3 | B3 | H | G1 | G1 | H | G2 | G2 |
| 94 | B3 | B3 | H | G2 | G2 | H | G2 | G2 |
| 95 | B3 | B3 | H | G3 | G3 | H | G2 | G2 |
| 96 | B3 | B3 | H | G4 | G4 | H | G2 | G2 |
| 97 | B3 | B3 | H | G5 | G5 | H | G2 | G2 |
| 98 | B3 | B3 | G1 | H | H | G1 | G2 | G2 |
| 99 | B3 | B3 | G2 | H | H | G2 | G2 | G2 |
| 100 | B3 | B3 | G3 | H | H | G3 | G2 | G2 |
| 101 | B3 | B3 | G4 | H | H | G4 | G2 | G2 |
| 102 | B3 | B3 | G5 | H | H | G5 | G2 | G2 |
| 103 | B3 | B3 | G1 | G1 | G1 | G1 | G2 | G2 |
| 104 | B3 | B3 | H | G1 | G1 | H | G3 | G3 |
| 105 | B3 | B3 | H | G2 | G2 | H | G3 | G3 |
| 106 | B3 | B3 | H | G3 | G3 | H | G3 | G3 |
| 107 | B3 | B3 | H | G4 | G4 | H | G3 | G3 |
| 108 | B3 | B3 | H | G5 | G5 | H | G3 | G3 |
| 109 | B3 | B3 | G1 | H | H | G1 | G3 | G3 |
| 110 | B3 | B3 | G2 | H | H | G2 | G3 | G3 |
| 111 | B3 | B3 | G3 | H | H | G3 | G3 | G3 |
| 112 | B3 | B3 | G4 | H | H | G4 | G3 | G3 |
| 113 | B3 | B3 | G5 | H | H | G5 | G3 | G3 |
| 114 | B3 | B3 | G1 | G1 | G1 | G1 | G3 | G3 |
| 115 | B3 | B3 | H | G1 | G1 | H | G4 | G4 |
| 116 | B3 | B3 | H | G2 | G2 | H | G4 | G4 |
| 117 | B3 | B3 | H | G3 | G3 | H | G4 | G4 |
| 118 | B3 | B3 | H | G4 | G4 | H | G4 | G4 |
| 119 | B3 | B3 | H | G5 | G5 | H | G4 | G4 |
| 120 | B3 | B3 | G1 | H | H | G1 | G4 | G4 |
| 121 | B3 | B3 | G2 | H | H | G2 | G4 | G4 |
| 122 | B3 | B3 | G3 | H | H | G3 | G4 | G4 |
| 123 | B3 | B3 | G4 | H | H | G4 | G4 | G4 |
| 124 | B3 | B3 | G5 | H | H | G5 | G4 | G4 |
| 125 | B3 | B3 | G1 | G1 | G1 | G1 | G4 | G4 |
| 126 | B3 | B3 | H | G1 | G1 | H | G5 | G5 |
| 127 | B3 | B3 | H | G2 | G2 | H | G5 | G5 |
| 128 | B3 | B3 | H | G3 | G3 | H | G5 | G5 |
| 129 | B3 | B3 | H | G4 | G4 | H | G5 | G5 |
| 130 | B3 | B3 | H | G5 | G5 | H | G5 | G5 |
| 131 | B3 | B3 | G1 | H | H | G1 | G5 | G5 |
| 132 | B3 | B3 | G2 | H | H | G2 | G5 | G5 |
| 133 | B3 | B3 | G3 | H | H | G3 | G5 | G5 |
| 134 | B3 | B3 | G4 | H | H | G4 | G5 | G5 |
| 135 | B3 | B3 | G5 | H | H | G5 | G5 | G5 |
| 136 | B3 | B3 | G1 | G1 | G1 | G1 | G5 | G5 |
| 137 | B4 | B4 | H | H | H | H | G2 | G2 |
| 138 | B4 | B4 | H | G1 | G1 | H | G2 | G2 |
| 139 | B4 | B4 | H | G2 | G2 | H | G2 | G2 |
| 140 | B4 | B4 | H | G3 | G3 | H | G2 | G2 |
| 141 | B4 | B4 | H | G4 | G4 | H | G2 | G2 |
| 142 | B4 | B4 | H | G5 | G5 | H | G2 | G2 |
| 143 | B4 | B4 | G1 | H | H | G1 | G2 | G2 |
| 144 | B4 | B4 | G2 | H | H | G2 | G2 | G2 |
| 145 | B4 | B4 | G3 | H | H | G3 | G2 | G2 |
| 146 | B4 | B4 | G4 | H | H | G4 | G2 | G2 |
| 147 | B4 | B4 | G5 | H | H | G5 | G2 | G2 |
| 148 | B4 | B4 | G1 | G1 | G1 | G1 | G2 | G2 |
| 149 | B4 | B4 | H | G1 | G1 | H | G3 | G3 |
| 150 | B4 | B4 | H | G2 | G2 | H | G3 | G3 |
| 151 | B4 | B4 | H | G3 | G3 | H | G3 | G3 |
| 152 | B4 | B4 | H | G4 | G4 | H | G3 | G3 |
| 153 | B4 | B4 | H | G5 | G5 | H | G3 | G3 |
| 154 | B4 | B4 | G1 | H | H | G1 | G3 | G3 |
| 155 | B4 | B4 | G2 | H | H | G2 | G3 | G3 |
| 156 | B4 | B4 | G3 | H | H | G3 | G3 | G3 |

TABLE 1-continued

| No. | $Y^1$ | $Y^2$ | $R^5$ | $R^6$ | $R^9$ | $R^{10}$ | $R^{23}$ | $R^{26}$ |
|---|---|---|---|---|---|---|---|---|
| 157 | B4 | B4 | G4 | H | H | G4 | G3 | G3 |
| 158 | B4 | B4 | G5 | H | H | G5 | G3 | G3 |
| 159 | B4 | B4 | G1 | G1 | G1 | G1 | G3 | G3 |
| 160 | B4 | B4 | H | G1 | G1 | H | G4 | G4 |
| 161 | B4 | B4 | H | G2 | G2 | H | G4 | G4 |
| 162 | B4 | B4 | H | G3 | G3 | H | G4 | G4 |
| 163 | B4 | B4 | H | G4 | G4 | H | G4 | G4 |
| 164 | B4 | B4 | H | G5 | G5 | H | G4 | G4 |
| 165 | B4 | B4 | G1 | H | H | G1 | G4 | G4 |
| 166 | B4 | B4 | G2 | H | H | G2 | G4 | G4 |
| 167 | B4 | B4 | G3 | H | H | G3 | G4 | G4 |
| 168 | B4 | B4 | G4 | H | H | G4 | G4 | G4 |
| 169 | B4 | B4 | G5 | H | H | G5 | G4 | G4 |
| 170 | B4 | B4 | G1 | G1 | G1 | G1 | G4 | G4 |
| 171 | B4 | B4 | H | G1 | G1 | H | G5 | G5 |
| 172 | B4 | B4 | H | G2 | G2 | H | G5 | G5 |
| 173 | B4 | B4 | H | G3 | G3 | H | G5 | G5 |
| 174 | B4 | B4 | H | G4 | G4 | H | G5 | G5 |
| 175 | B4 | B4 | H | G5 | G5 | H | G5 | G5 |
| 176 | B4 | B4 | G1 | H | H | G1 | G5 | G5 |
| 177 | B4 | B4 | G2 | H | H | G2 | G5 | G5 |
| 178 | B4 | B4 | G3 | H | H | G3 | G5 | G5 |
| 179 | B4 | B4 | G4 | H | H | G4 | G5 | G5 |
| 180 | B4 | B4 | G5 | H | H | G5 | G5 | G5 |
| 181 | B4 | B4 | G1 | G1 | G1 | G1 | G5 | G5 |
| 182 | B5 | B5 | H | H | H | H | G2 | G2 |
| 183 | B5 | B5 | H | G1 | G1 | H | G2 | G2 |
| 184 | B5 | B5 | H | G2 | G2 | H | G2 | G2 |
| 185 | B5 | B5 | H | G3 | G3 | H | G2 | G2 |
| 186 | B5 | B5 | H | G4 | G4 | H | G2 | G2 |
| 187 | B5 | B5 | H | G5 | G5 | H | G2 | G2 |
| 188 | B5 | B5 | G1 | H | H | G1 | G2 | G2 |
| 189 | B5 | B5 | G3 | H | H | G3 | G2 | G2 |
| 190 | B5 | B5 | G4 | H | H | G4 | G2 | G2 |
| 191 | B5 | B5 | G5 | H | H | G5 | G2 | G2 |
| 192 | B5 | B5 | G1 | G1 | G1 | G1 | G2 | G2 |
| 193 | B5 | B5 | H | G1 | G1 | H | G3 | G3 |
| 194 | B5 | B5 | H | G2 | G2 | H | G3 | G3 |
| 195 | B5 | B5 | H | G3 | G3 | H | G3 | G3 |
| 196 | B5 | B5 | H | G4 | G4 | H | G3 | G3 |
| 197 | B5 | B5 | H | G5 | G5 | H | G3 | G3 |
| 198 | B5 | B5 | G1 | H | H | G1 | G3 | G3 |
| 199 | B5 | B5 | G2 | H | H | G2 | G3 | G3 |
| 200 | B5 | B5 | G3 | H | H | G3 | G3 | G3 |
| 201 | B5 | B5 | G4 | H | H | G4 | G3 | G3 |
| 202 | B5 | B5 | G5 | H | H | G5 | G3 | G3 |
| 203 | B5 | B5 | G1 | G1 | G1 | G1 | G3 | G3 |
| 204 | B5 | B5 | H | G1 | G1 | H | G4 | G4 |
| 205 | B5 | B5 | H | G2 | G2 | H | G4 | G4 |
| 206 | B5 | B5 | H | G3 | G3 | H | G4 | G4 |
| 207 | B5 | B5 | H | G4 | G4 | H | G4 | G4 |
| 208 | B5 | B5 | H | G5 | G5 | H | G4 | G4 |
| 209 | B5 | B5 | G1 | H | H | G1 | G4 | G4 |
| 210 | B5 | B5 | G2 | H | H | G2 | G4 | G4 |
| 211 | B5 | B5 | G3 | H | H | G3 | G4 | G4 |
| 212 | B5 | B5 | G4 | H | H | G4 | G4 | G4 |
| 213 | B5 | B5 | G5 | H | H | G5 | G4 | G4 |
| 214 | B5 | B5 | G1 | G1 | G1 | G1 | G4 | G4 |
| 215 | B5 | B5 | H | G1 | G1 | H | G5 | G5 |
| 216 | B5 | B5 | H | G2 | G2 | H | G5 | G5 |
| 217 | B5 | B5 | H | G3 | G3 | H | G5 | G5 |
| 218 | B5 | B5 | H | G4 | G4 | H | G5 | G5 |
| 219 | B5 | B5 | H | G5 | G5 | H | G5 | G5 |
| 220 | B5 | B5 | G1 | H | H | G1 | G5 | G5 |
| 221 | B5 | B5 | G2 | H | H | G2 | G5 | G5 |
| 222 | B5 | B5 | G3 | H | H | G3 | G5 | G5 |
| 223 | B5 | B5 | G4 | H | H | G4 | G5 | G5 |
| 224 | B5 | B5 | G5 | H | H | G5 | G5 | G5 |
| 225 | B5 | B5 | G1 | G1 | G1 | G1 | G5 | G5 |
| 226 | B6 | B6 | H | H | H | H | G2 | G2 |
| 227 | B6 | B6 | H | G1 | G1 | H | G2 | G2 |
| 228 | B6 | B6 | H | G2 | G2 | H | G2 | G2 |
| 229 | B6 | B6 | H | G3 | G3 | H | G2 | G2 |
| 230 | B6 | B6 | H | G4 | G4 | H | G2 | G2 |
| 231 | B6 | B6 | H | G5 | G5 | H | G2 | G2 |
| 232 | B6 | B6 | G1 | H | H | G1 | G2 | G2 |
| 233 | B6 | B6 | G2 | H | H | G2 | G2 | G2 |
| 234 | B6 | B6 | G3 | H | H | G3 | G2 | G2 |

TABLE 1-continued

| No. | $Y^1$ | $Y^2$ | $R^5$ | $R^6$ | $R^9$ | $R^{10}$ | $R^{23}$ | $R^{26}$ |
|---|---|---|---|---|---|---|---|---|
| 235 | B6 | B6 | G4 | H | H | G4 | G2 | G2 |
| 236 | B6 | B6 | G5 | H | H | G5 | G2 | G2 |
| 237 | B6 | B6 | G1 | G1 | G1 | G1 | G2 | G2 |
| 238 | B6 | B6 | H | G1 | G1 | H | G3 | G3 |
| 239 | B6 | B6 | H | G2 | G2 | H | G3 | G3 |
| 240 | B6 | B6 | H | G3 | G3 | H | G3 | G3 |
| 241 | B6 | B6 | H | G4 | G4 | H | G3 | G3 |
| 242 | B6 | B6 | H | G5 | G5 | H | G3 | G3 |
| 243 | B6 | B6 | G1 | H | H | G1 | G3 | G3 |
| 244 | B6 | B6 | G2 | H | H | G2 | G3 | G3 |
| 245 | B6 | B6 | G3 | H | H | G3 | G3 | G3 |
| 246 | B6 | B6 | G4 | H | H | G4 | G3 | G3 |
| 247 | B6 | B6 | G5 | H | H | G5 | G3 | G3 |
| 248 | B6 | B6 | G1 | G1 | G1 | G1 | G3 | G3 |
| 249 | B6 | B6 | H | G1 | G1 | H | G4 | G4 |
| 250 | B6 | B6 | H | G2 | G2 | H | G4 | G4 |
| 251 | B6 | B6 | H | G3 | G3 | H | G4 | G4 |
| 252 | B6 | B6 | H | G4 | G4 | H | G4 | G4 |
| 253 | B6 | B6 | H | G5 | G5 | H | G4 | G4 |
| 254 | B6 | B6 | G1 | H | H | G1 | G4 | G4 |
| 255 | B6 | B6 | G2 | H | H | G2 | G4 | G4 |
| 256 | B6 | B6 | G3 | H | H | G3 | G4 | G4 |
| 257 | B6 | B6 | G4 | H | H | G4 | G4 | G4 |
| 258 | B6 | B6 | G5 | H | H | G5 | G4 | G4 |
| 259 | B6 | B6 | G1 | G1 | G1 | G1 | G4 | G4 |
| 260 | B6 | B6 | H | G1 | G1 | H | G5 | G5 |
| 261 | B6 | B6 | H | G2 | G2 | H | G5 | G5 |
| 262 | B6 | B6 | H | G3 | G3 | H | G5 | G5 |
| 263 | B6 | B6 | H | G4 | G4 | H | G5 | G5 |
| 264 | B6 | B6 | H | G5 | G5 | H | G5 | G5 |
| 265 | B6 | B6 | G1 | H | H | G1 | G5 | G5 |
| 266 | B6 | B6 | G2 | H | H | G2 | G5 | G5 |
| 267 | B6 | B6 | G3 | H | H | G3 | G5 | G5 |
| 268 | B6 | B6 | G4 | H | H | G4 | G5 | G5 |
| 269 | B6 | B6 | G5 | H | H | G5 | G5 | G5 |
| 270 | B6 | B6 | G1 | G1 | G1 | G1 | G5 | G5 |

A specific example of the other compound represented by the general formula (1) is shown below.

Compound 271

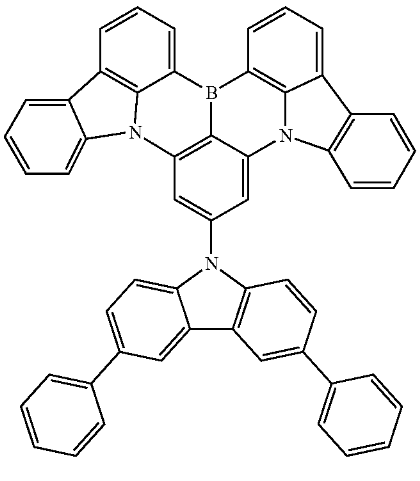

[Synthesis Method for Compound of General Formula (1)]

The compound represented by the general formula (1) can be synthesized by combining known reactions. For example, the compound can be synthesized via an intermediate (A) according to the following reaction scheme.

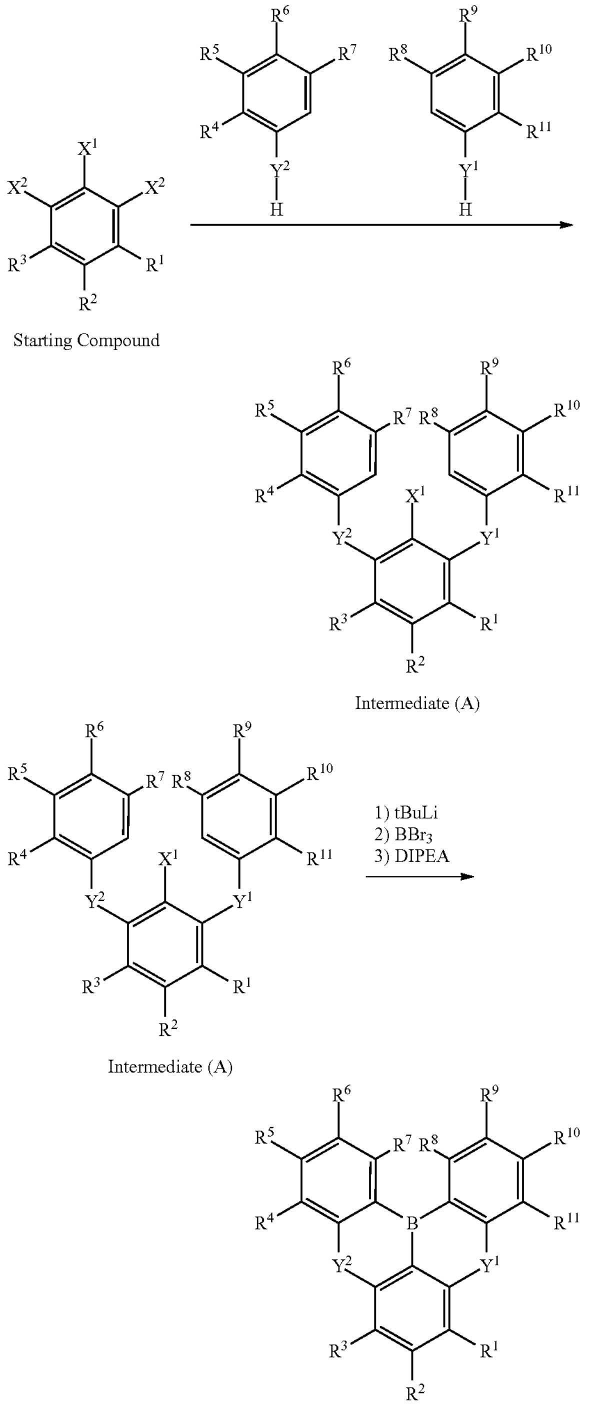

In this reaction scheme, the definition of $Y^1$, $Y^2$, and $R^1$ to $R^{11}$ is the same as the definition of $Y^1$, $Y^2$, and $R^1$ to $R^{11}$ in the above-mentioned general formula (1). $X^1$ and $X^2$ each independently represent a halogen atom. As the halogen atom, preferably exemplified are a fluorine atom, a chlorine atom, a bromine atom and an iodine atom. Preferably, $X^1$ and $X^2$ are different halogen atoms. For example, a chlorine atom can be selected for $X^1$, and a bromine atom for $X^2$.

In the above reaction scheme, a trihalide of a benzene substituted with $R^1$, $R^2$ and $R^3$ is used as a starting compound. The starting compound is reacted with a substituted or unsubstituted benzene having a group H—$Y^2$ and a substituted or unsubstituted benzene having a group H—$Y^1$ to give an intermediate (A). Further t-BuLi is added to the intermediate (A) and cooled, then tribromoboron is added, and further diisopropylamine is added and stirred to give the intended compound represented by the general formula (1). For details of the reaction, reference can be made to Synthesis Examples given hereinunder.

The compound represented by the general formula (1) can also be synthesized by combining any other known synthesis reactions.

[Synthetic Intermediate]

The compound represented by the following general formula (A), which is a synthetic intermediate for the compound represented by the general formula (1), includes a novel compound.

General Formula (A)

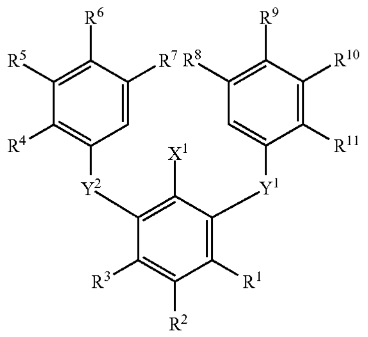

$X^1$ represents a halogen atom.

$Y^1$ represents N—$R^A$.

$Y^2$ represents O, S, C═O or N—$R^A$.

$R^A$ each independently represents a substituted or unsubstituted aryl group, or a substituted or unsubstituted heteroaryl group.

$R^1$ to $R^{11}$ each independently represent a hydrogen atom or a substituent, $R^1$ and $R^2$, $R^2$ and $R^3$, $R^4$ and $R^5$, $R^5$ and $R^6$, $R^6$ and $R^7$, $R^8$ and $R^9$, $R^9$ and $R^{10}$, $R^{10}$ and $R^{11}$, $R^A$ and $R^4$, and $R^A$ and $R^{11}$ each may bond to each other to form a cyclic structure, provided that at least one of $R^1$, $R^2$ and $R^3$ is a group represented by the following general formula (2).

General Formula (2)

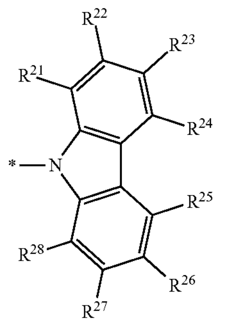

$R^{21}$ to $R^{28}$ each independently represent a hydrogen atom or a substituent, $R^{21}$ and $R^{22}$, $R^{22}$ and $R^{23}$, $R^{23}$ and $R^{24}$, $R^{25}$ and $R^{26}$, $R^{26}$ and $R^{27}$, and $R^{27}$ and $R^{28}$ each can bond to each other to form a cyclic structure, provided that at least one of $R^{21}$ to $R^{28}$ is a substituted or unsubstituted aryl group or a substituted or unsubstituted heteroaryl group, * indicates a bonding position.

For the description and the preferred range $Y^1$, $Y^2$, and $R^1$ to $R^{11}$ in the general formula (A), reference can be made to the description and the preferred range of $Y^1$, $Y^2$, and $R^1$ to $R^{11}$ in the general formula (1) mentioned above. The halogen atom for $X^1$ includes a fluorine atom, a chlorine atom, a bromine atom and an iodine atom. A fluorine atom, a chlorine atom and a bromine atom are preferred, and a chlorine atom is more preferred.

As specific examples of the compound represented by the general formula (A), there are mentioned compounds A1 to A270 each having the same $Y^1$, $Y^2$, and $R^1$ to $R^{11}$ as those in the above-mentioned compounds 1 to 270 and having a chlorine atom for $X^1$. As typical examples, structures of the compounds A1 to A3 are shown below. The scope of the compound represented by the general formula (A) should not be limitatively interpreted by these specific examples.

Compound A1

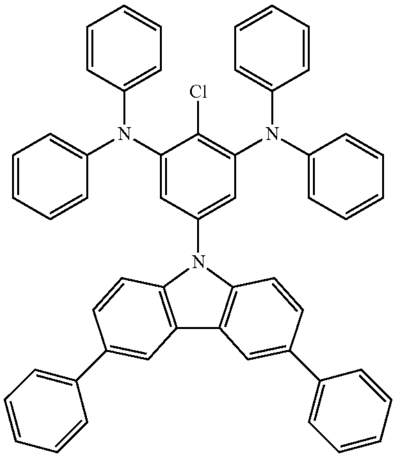

Compound A2

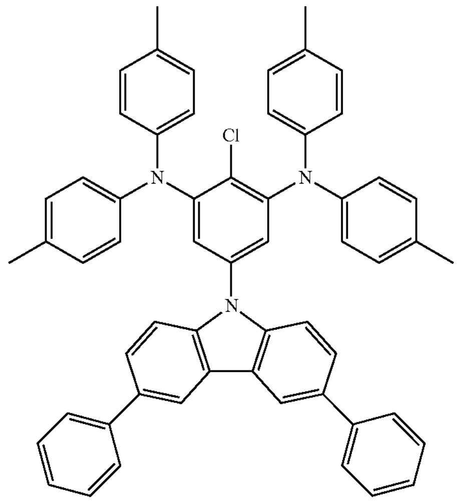

-continued

Compound A3

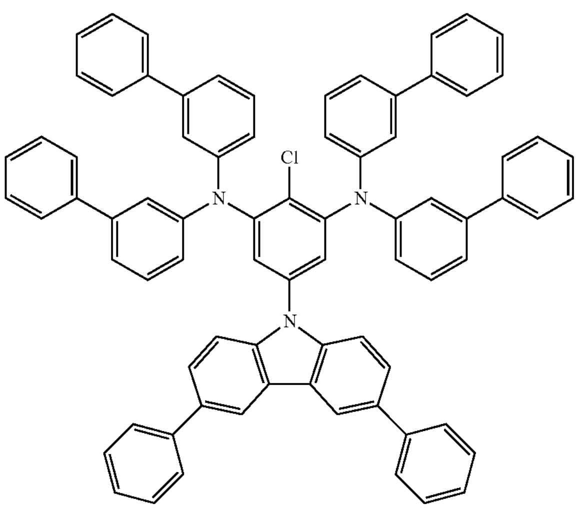

Definitions

Unless otherwise defined herein, scientific and technical terms used in this application shall have the meanings that are commonly understood by those of ordinary skill in the art. Generally, nomenclature used in connection with, and techniques of, chemistry described herein, are those well-known and commonly used in the art.

The term "alkoxy" refers to an alkyl group, having an oxygen attached thereto. In some embodiments, an alkoxy has 1-20 carbon atoms. Representative alkoxy groups include methoxy, trifluoromethoxy, ethoxy, propoxy, and tert-butoxy.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 12 carbon atoms unless otherwise defined. In some embodiments, the alkyl group has from 1 to 8 carbon atoms, from 1 to 6 carbon atoms, from 1 to 4 carbon atoms, or from 1 to 3 carbon atoms. Examples of straight chained and branched alkyl groups include methyl, ethyl, n-propyl, iso-propyl, n-butyl, sec-butyl, tert-butyl, pentyl, hexyl, heptyl and octyl.

Moreover, the term "alkyl" as used throughout the specification, examples, and claims is intended to include both "unsubstituted alkyls" and "substituted alkyls", the latter of which refers to alkyl moieties having substituents replacing a hydrogen on one or more substitutable carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amino, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amino, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $-CF_3$, —CN. Exemplary substituted alkyls are described below. Cycloalkyls can be further substituted with alkyls, alkenyls, alkoxys, alkylthios, aminoalkyls, carbonyl-substituted alkyls, $-CF_3$, —CN.

The term "$C_{x-y}$" when used in conjunction with a chemical moiety, such as, acyl, acyloxy, alkyl, alkenyl, alkynyl, or alkoxy is meant to include groups that contain from x to y carbon atoms in the chain. For example, the term "$C_{x-y}$ alkyl group" refers to substituted or unsubstituted saturated hydrocarbon groups, including straight-chain alkyl group and branched-chain alkyl group that contain from x to y carbon atoms in the chain, including haloalkyl groups. Preferred haloalkyl groups include trifluoromethyl, difluoromethyl, 2,2,2-trifluoroethyl, and pentafluoroethyl. $C_0$ alkyl group indicates a hydrogen atom where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The terms "amine" and "amino" are art-recognized and refer to both unsubstituted and substituted amines and salts thereof, e.g., a moiety that can be represented by

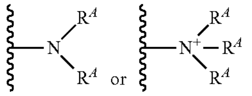

wherein each $R^A$ independently represents a hydrogen or a hydrocarbyl group, or two $R^A$ are taken together with the N atom to which they are attached complete a heterocycle having from 4 to 8 atoms in the ring structure.

The term "aryl" as used herein include substituted or unsubstituted single-ring aromatic groups in which each atom of the ring is carbon atom. Preferably the ring is a 6- or 20-membered ring, more preferably a 6-membered ring. Preferably aryl having 6-10 carbon atoms, more preferably having 6-25 carbon atoms.

The term "aryl" also includes polycyclic ring systems having two or more cyclic rings in which two or more carbon atoms are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline.

The terms "carbocycle", and "carbocyclic", as used herein, refers to a saturated or unsaturated ring in which each atom of the ring is carbon atom. Preferably, a carbocylic group has from 3 to 20 carbon atoms. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl (Ph) group, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The terms "halo" and "halogen" as used herein means halogen atom and includes chloro, fluoro, bromo, and iodo.

The terms "heteroaryl" and "hetaryl" include substituted or unsubstituted aromatic single ring structures, preferably 5- to 20-membered rings, more preferably 5- to 6-membered rings, whose ring structures include at least one heteroatom, preferably one to four heteroatoms, more preferably one or two heteroatoms. Preferably heteroaryl has 2-40 carbon atoms, more preferably has 2-25 carbon atoms. The terms "heteroaryl" and "hetaryl" also include polycyclic ring systems having two or more cyclic rings in which two or more carbon atoms are common to two adjoining rings wherein at least one of the rings is heterocycle, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, pyrimidine, and carbazole.

The terms "heterocyclyl," "heterocycle," and "heterocyclic" refer to substituted or unsubstituted non-aromatic ring structures, preferably 3- to 20-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbon atoms are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams.

The term "substituted" refers to moieties having substituents replacing a hydrogen on one or more carbon atoms of the main chain. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Moieties that may be substituted can include any appropriate substituents described herein, for example, acyl, acylamino, acyloxy, alkoxy, alkoxyalkyl, alkenyl, alkyl, alkylamino, alkylthio, arylthio, alkynyl, amide, amino, aminoalkyl, aralkyl, carbamate, carbocyclyl, cycloalkyl, carbocyclylalkyl, carbonate, ester, ether, heteroaralkyl, heterocyclyl, heterocyclylalkyl, hydrocarbyl, silyl, sulfone, or thioether. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a. cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

"Hole transport layer (HTL)" and like terms mean a layer made from a material which transports holes. High hole mobility is recommended. The HTL is used to help block passage of electrons transported by the emitting layer. Low electron affinity is typically required to block electrons. The HTL should desirably have larger triplets to block exciton migrations from an adjacent emissive layer (EML).

"Emitting layer" and like terms mean a layer which emits light. In some embodiments, the emitting layer comprises a host material and guest material. The guest material can also be referred to as a dopant material, but the disclosure is not limited thereto. The host material could be bipolar or unipolar and may be used alone or by combination of two or more host materials. The opto-electrical properties of the host material may differ to which type of guest material (TADF, Phosphorescent or Fluorescent) is used. For Fluorescent guest materials, the host materials should have good spectral overlap between absorption of the guest material and emission of the host material to induce good Foerster transfer to guest materials. For Phosphorescent guest materials, the host materials should have high triplet energy to confine triplets of the guest material. For TADF guest materials, the host materials should have both spectral overlap and higher triplet energy.

"Dopant" and like terms, refer to additive materials for carrier transporting layers, emitting layers or other layers. In carrier transporting layers, dopant and like terms perform as an electron acceptor or a donator that increases the conductivity of an organic layer of an organic electronic device, when added to the organic layer as an additive. Organic semiconductors may likewise be influenced, with regard to their electrical conductivity, by doping. Such organic semiconducting matrix materials may be made up either of compounds with electron-donor properties or of compounds with electron-acceptor properties. In emitting layers, dopant and like terms also mean the light emitting material which is dispersed in a matrix, for example, a host. When a triplet harvesting material is doped into an emitting layer or contained in an adjacent layer so as to improve exciton generation efficiency, it is named as assistant dopant. An assistant dopant may preferably shorten a lifetime of the exciton. The content of the assistant dopant in the light emitting layer or the adjacent layer is not particularly limited so long as the triplet harvesting material improves the exciton generation efficiency. The content of the assistant dopant in the light emitting layer is preferably higher than, more preferably at least twice than the light emitting material. In the light emitting layer, the content of the host material is preferably 50% by weight or more, the content of the assistant dopant is preferably from 5% by weight to less than 50% by weight, and the content of the light emitting material is preferably more than 0% by weight to less than 30% by weight, more preferably from 0% by weight to less than 10% by weight. The content of the assistant dopant in the adjacent layer may be more than 50% by weight and may be 100% by weight. In the case where a device comprising a triplet harvesting material in a light emitting layer or an adjacent layer has a higher light emission efficiency than a device without the triplet harvesting material, such triplet harvesting material functions as an assistant dopant. A light emitting layer comprising a host material, an assistant dopant and a light emitting material satisfies the following (A) and preferably satisfies the following (B):

$$ES1(A) > ES1(B) > ES1(C) \quad (A)$$

$$ET1(A) > ET1(B) \quad (B)$$

wherein ES1(A) represents a lowest excited singlet energy level of the host material; ES1(B) represents a lowest excited singlet energy level of the assistant dopant; ES1(C) represents a lowest excited singlet energy level of the light emitting material; ET1(A) represents a lowest excited triplet energy level at 77 K of the host material; and ET1(B) represents a lowest excited triplet energy level at 77 K of the assistant dopant. The assistant dopant has an energy difference $\Delta E_{ST}$ between a lowest singlet excited state and a lowest triplet excited state at 77 K of preferably 0.3 eV or less, more preferably 0.2 eV or less, still more preferably 0.1 eV or less.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also, unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In various embodiments, compounds of this invention have an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species that differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

"Substituted with deuterium" refers to the replacement of one or more hydrogen atoms with a corresponding number of deuterium atoms. "D" and "d" both refer to deuterium.

In some embodiments, the compound represented by the general formula (1) is a light-emitting material.

In some embodiments of the present disclosure, the compound represented by the general formula (1) is a compound capable of emitting delayed fluorescence.

In some embodiments, the compound represented by the general formula (1) is, when excited thermally or by an electronic means, able to emit light in a UV region, emit light of blue, green, yellow or orange in a visible region, or emit light in a red region (e.g., about 420 nm to about 500 nm, about 500 nm to about 600 nm, or about 600 nm to about 700 nm) or in a near IR region.

In some embodiments of the present disclosure, the compound represented by the general formula (1) is, when excited thermally or by an electronic means, able to emit light of red or orange in a visible region (e.g., about 620 nm to about 780 nm, about 650 nm).

In some embodiments of the present disclosure, the compound represented by the general formula (1) is, when excited thermally or by an electronic means, able to emit light of orange or yellow in a visible region (e.g., about 570 nm to about 620 nm, about 590 nm, about 570 nm).

In some embodiments of the present disclosure, the compound represented by the general formula (1) is, when excited thermally or by an electronic means, able to emit light of green in a visible region (e.g., about 490 nm to about 575 nm, about 510 nm).

In some embodiments of the present disclosure, the compound represented by the general formula (1) is, when excited thermally or by an electronic means, able to emit light of blue in a visible region (e.g., about 400 nm to about 490 nm, about 475 nm).

In some embodiments of the present disclosure, the compound represented by the general formula (1) is, when excited thermally or by an electronic means, able to emit light in a UV region (e.g., about 280 to 400 nm).

In some embodiments of the present disclosure, the compound represented by the general formula (1) is, when excited thermally or by an electronic means, able to emit light in an IR region about 780 nm to 2 μm).

Electronic characteristics of small-molecule chemical substance libraries can be calculated by known ab initio quantum chemistry calculation. For example, according to time-dependent density functional theory calculation using 6-31G* as a basis, and a functional group known as Becke's three parameters. Lee-Yang-Parr hybrid functionals, the Hartree-Fock equation (TD-DFT/B3LYP/6-31G*) is analyzed and molecular fractions (parts) having HOMO not lower than a specific threshold value and LUMO not higher than a specific threshold value can be screened, and the calculated triplet state of the parts is more than 2.75 eV.

With that, for example, in the presence of a HOMO energy (for example, ionizing potential) of −6.5 eV or more, a donor part ("D") can be selected. On the other hand, for example, in the presence of a LUMO energy (for example, electron affinity) of −0.5 eV or less, an acceptor part ("A") can be selected. A bridge part ("B") is a strong conjugated system, for example, capable of strictly limiting the acceptor part and the donor part in a specific three-dimensional configuration, and therefore prevents the donor part and the acceptor part from overlapping in the pai-conjugated system.

In some embodiments, a compound library is screened using at least one of the following characteristics.

1. Light emission around a specific wavelength.
2. A triplet state over a calculated specific energy level.
3. $\Delta E_{ST}$ value lower than a specific value.
4. Quantum yield more than a specific value.
5. HOMO level.
6. LUMO level.

In some embodiments, the difference ($\Delta E_{ST}$) between the lowest singlet excited state and the lowest triplet excited state at 77 K is less than about 0.5 eV, less than about 0.4 eV, less than about 0.3 eV, less than about 0.2 eV, or less than about 0.1 eV. In some embodiments, $\Delta E_{ST}$ value is less than about 0.09 eV, less than about 0.08 eV, less than about 0.07 eV, less than about 0.06 eV, less than about 0.05 eV, less than about 0.04 eV, less than about 0.03 eV, less than about 0.02 eV, or less than about 0.01 eV.

In some embodiments, the compound represented by the general formula (1) shows a quantum yield of more than 25%, for example, about 30%, about 35%, about 40%, about 45%, about 50%, about 55%, about 60%, about 65%, about 70%, about 75%, about 80%, about 85%, about 90%, about 95% or more.

[Structure Using the Compound of the Disclosure]

In some embodiments, the compound represented by the general formula (1) is used along with one or more materials (e.g., small molecules, polymers, metals, metal complexes), by combining them, or by dispersing the compound, or by covalent-bonding with the compound, or by coating with the compound, or by carrying the compound, or by associating with the compound, and solid films or layers are formed. For example, by combining the compound represented by the general formula (1) with an electroactive material, a film can be formed. In some cases, the compound represented by the general formula (1) can be combined with a hole transporting polymer. In some cases, the compound represented by the general formula (1) can be combined with an electron transporting polymer. In some cases, the compound represented by the general formula (1) can be combined with a hole transporting polymer and an electron transporting polymer. In some cases, the compound represented by the general formula (1) can be combined with a copolymer having both a hole transporting moiety and an electron transporting moiety. In the embodiments mentioned above, the electrons and/or the holes formed in a solid film or layer can be interacted with the compound represented by the general formula (1).

[Film Formation]

In some embodiments, a film containing the compound represented by the general formula (1) can be formed in a wet process. In a wet process, a solution prepared by dissolving a composition containing the compound of the present invention is applied onto a surface, and then the solvent is removed to form a film. The wet process includes a spin coating method, a slit coating method, an ink jet method (a spraying method), a gravure printing method, an offset printing method and flexographic printing method, which, however are not limitative. In the wet process, an appropriate organic solvent capable of dissolving a composition containing the compound of the present invention is selected and used. In some embodiments, a substituent (e.g., an alkyl group) capable of increasing the solubility in an organic solvent can be introduced into the compound contained in the composition.

In some embodiments, a film containing the compound of the present invention can be formed in a dry process. In some embodiments, a vacuum evaporation method is employable as a dry process, which, however, is not limitative. In the case where a vacuum evaporation method is employed, compounds to constitute a film can be co-evaporated from individual evaporation sources, or can be co-evaporated from a single evaporation source formed by mixing the compounds. In the case where a single evaporation source is used, a mixed powder prepared by mixing compound powders can be used, or a compression molded body prepared by compression-molding the mixed powder can be used, or a mixture prepared by heating and melting the constituent compounds and cooling the resulting melt can be used. In some embodiments, by co-evaporation under the condition where the evaporation rate (weight reduction rate) of the plural compounds contained in a single evaporation source is the same or is nearly the same, a film having a compositional ratio corresponding to the compositional ratio of the plural compounds contained in the evaporation source can be formed. When plural compounds are mixed in the same compositional ratio as the compositional ratio of the film to be formed to prepare an evaporation source, a film having a desired compositional ratio can be formed in a simplified manner. In some embodiments, the temperature at which the compounds to be co-evaporated has the same weight reduction ratio is specifically defined, and the temperature can be employed as the temperature of co-evaporation.

[Use Examples of Compound of the Present Disclosure]

Organic Light Emitting Diode:

One embodiment of the present invention relates to use of the compound represented by the general formula (1) of the present invention as a light emitting material for organic light emitting devices. In some embodiments, the compound represented by the general formula (1) of the present invention can be effectively used as a light emitting material in a light emitting layer in an organic light emitting device. In some embodiments, the compound represented by the general formula (1) of the present invention includes delayed fluorescence (delayed fluorescent material) that emits delayed fluorescence. In some embodiments, the present invention provides a delayed fluorescent material having a structure represented by the general formula (1) of the present invention. In some embodiments, the present invention relates to use of the compound represented by the general formula (1) of the present invention as a delayed fluorescent material. In some embodiments, the compound represented by the general formula (1) of the present invention can be used as a host material, and can be used along with one or more light-emitting materials, and the light emitting material can be a fluorescent material, a phosphorescent material or a TADF. In some embodiments, the compound represented by the general formula (1) can be used as a hole transporting material. In some embodiments, the compound represented by the general formula (1) can be used as an electron transporting material. In some embodiments, the present invention relates to a method of generating delayed fluorescence from the compound represented by the general formula (1). In some embodiments, the organic light emitting device containing the compound as a light emitting material emits delayed fluorescence and shows a high light emission efficiency.

In some embodiments, the light emitting layer contains the compound represented by the general formula (1), and the compound represented by the general formula (1) is aligned in parallel to the substrate. In some embodiments, the substrate is a film-forming surface. In some embodiment, the alignment of the compound represented by the general formula (1) relative to the film-forming surface can have some influence on the propagation direction of light emitted by the aligned compounds, or can determine the direction. In some embodiments, by aligning the propagation direction of light emitted by the compound represented by the general formula (1), the light extraction efficiency from the light emitting layer can be improved.

One embodiment of the present invention relates to an organic light emitting device. In some embodiments, the organic light emitting device includes a light emitting layer. In some embodiments, the light emitting layer contains, as a light emitting material therein, the compound represented by the general formula (1). In some embodiments, the organic light emitting device is an organic photoluminescent device (organic PL device). In some embodiments, the organic light emitting device is an organic electroluminescent device (organic EL device). In some embodiments, the compound represented by the general formula (1) assists light irradiation from the other light emitting materials contained in the light emitting layer (as a so-called assist dopant). In some embodiments, the compound represented by the general formula (1) contained in the light emitting layer is in a lowest excited energy level, and is contained between the lowest excited single energy level of the host material contained in the light emitting layer and the lowest excited singlet energy level of the other light emitting materials contained in the light emitting layer.

In some embodiments, the organic photoluminescent device comprises at least one light-emitting layer. In some embodiments, the organic electroluminescent device comprises at least an anode, a cathode, and an organic layer between the anode and the cathode. In some embodiments, the organic layer comprises at least a light-emitting layer. In some embodiments, the organic layer comprises only a light-emitting layer. In some embodiments, the organic layer comprises one or more organic layers in addition to the light-emitting layer. Examples of the organic layer include a hole transporting layer, a hole injection layer, an electron barrier layer, a hole barrier layer, an electron injection layer, an electron transporting layer and an exciton barrier layer. In some embodiments, the hole transporting layer may be a hole injection and transporting layer having a hole injection function, and the electron transporting layer may be an electron injection and transporting layer having an electron injection function. An example of an organic electroluminescent device is shown in FIG. 1.

(Light Emitting Layer)

In some embodiments, the light emitting layer is a layer where holes and electrons injected from the anode and the cathode, respectively, are recombined to form excitons. In some embodiments, the layer emits light.

In some embodiments, only a light emitting material is used as the light emitting layer. In some embodiments, the light emitting layer contains a light emitting material and a host material. In some embodiments, the light emitting material is one or more compounds of the general formula (1). In some embodiments, for improving luminous radiation efficiency of an organic electroluminescent device and an organic photoluminescence device, the singlet exciton and the triplet exciton generated in a light emitting material is confined inside the light emitting material. In some embodiments, a host material is used in the light emitting layer in addition to a light emitting material therein. In some embodiments, the host material is an organic compound. In some embodiments, the organic compound has an excited singlet energy and an excited triplet energy, and at least one of them is higher than those in the light emitting material of the present invention. In some embodiments, the singlet exciton and the triplet exciton generated in the light emitting material of the present invention are confined in the molecules of the light emitting material of the present invention. In some embodiments, the singlet and triplet excitons are fully confined for improving luminous radiation efficiency. In some embodiments, although high luminous radiation efficiency is still attained, singlet excitons and triplet excitons are not fully confined, that is, a host material capable of attaining high luminous radiation efficiency can be used in the present invention with no specific limitation. In some embodiments, in the light emitting material in the light emitting layer of the device of the present invention, luminous radiation occurs. In some embodiments, radiated light includes both fluorescence and delayed fluorescence. In some embodiments, radiated light includes radiated light from a host material. In some embodiments, radiated light is composed of radiated light from a host material. In some embodiments, radiated light includes radiated light from the compound represented by the general formula (1) and radiated light from a host material. In some embodiment, a TADF molecule and a host material are used. In some embodiments, TADF is an assist dopant.

In some embodiments where a host material is used, the amount of the compound of the present invention as the light emitting material contained in the light emitting layer is 0.1% by weight or more. In some embodiments where a host material is used, the amount of the compound of the present invention contained in the light emitting layer is 1% by weight or more. In some embodiments where a host material is used, the amount of the compound of the present invention as the light emitting material contained in the light emitting layer is 50% by weight or less. In some embodiments where a host material is used, the amount of the compound of the present invention as the light emitting material contained in the light emitting layer is 20% by weight or less. In some embodiments where a host material is used, the amount of the compound of the present invention as the light emitting material contained in the light emitting layer is 10% by weight or less.

In some embodiments, the host material in the light emitting layer is an organic compound having a hole transporting function and an electron transporting function. In some embodiments, the host material in the light emitting layer is an organic compound that prevents increase in the wavelength of radiated light. In some embodiments, the host material in the light emitting layer is an organic compound having a high glass transition temperature.

In some embodiments, the host material is selected from the following group:

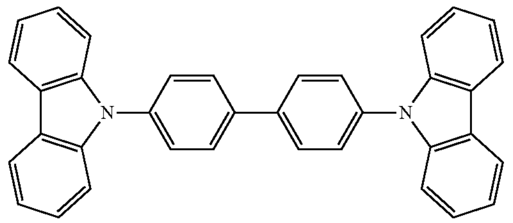

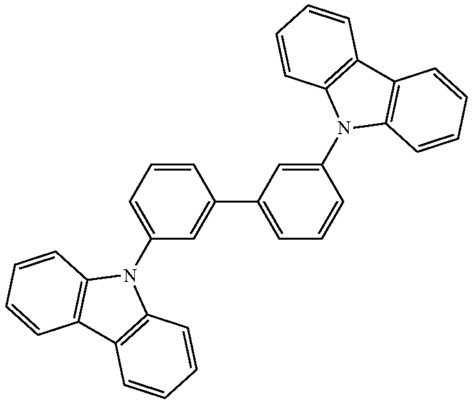

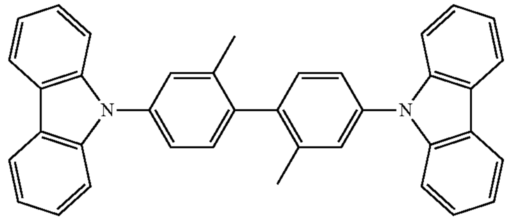

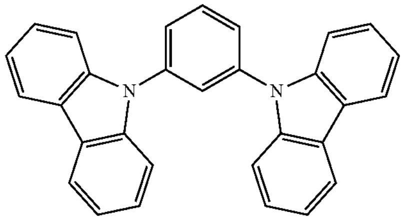

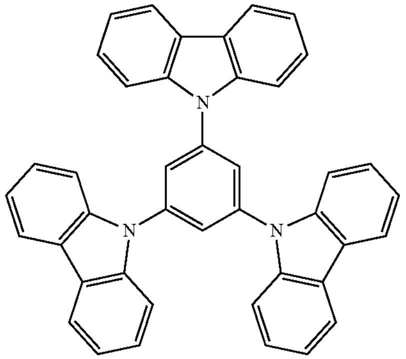

-continued

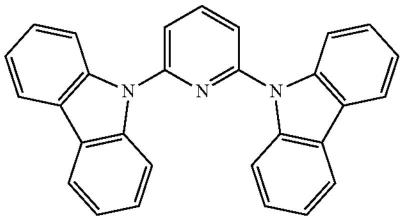

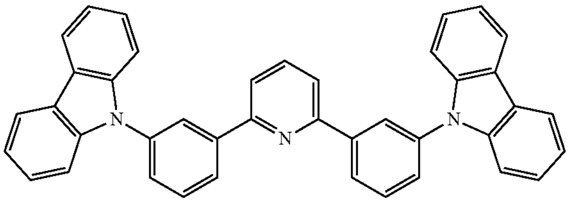

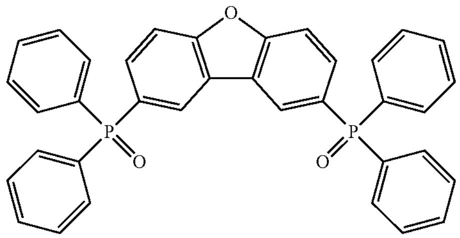

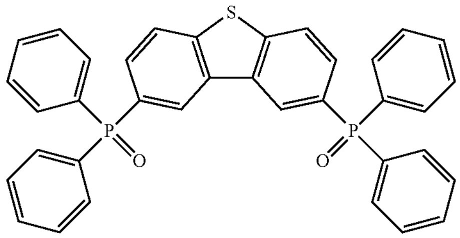

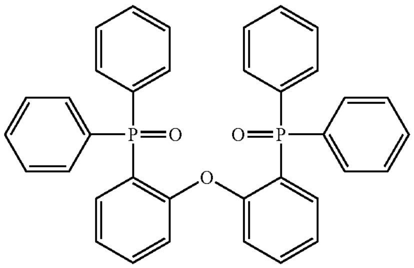

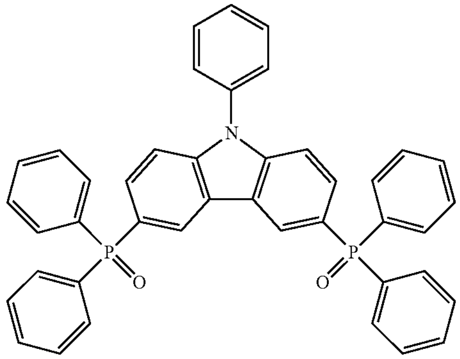

-continued
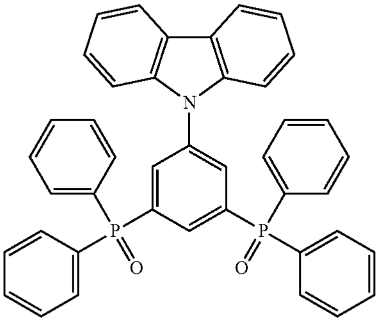
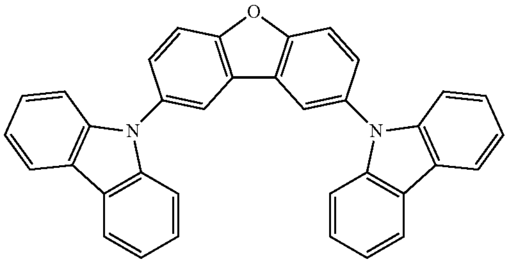
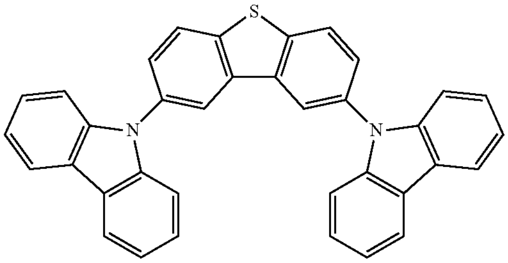
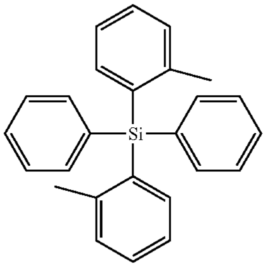
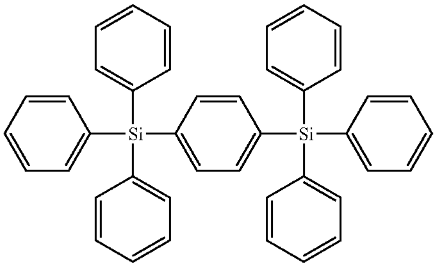
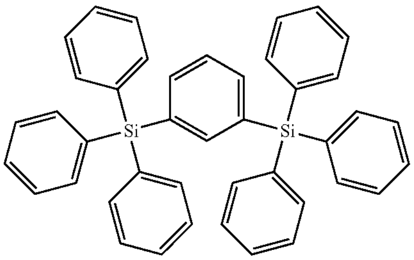
-continued
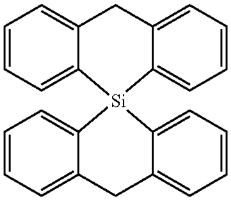
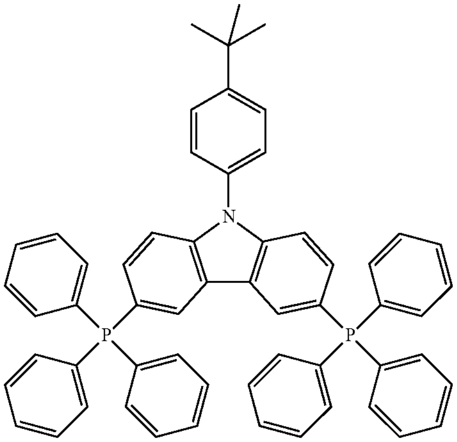
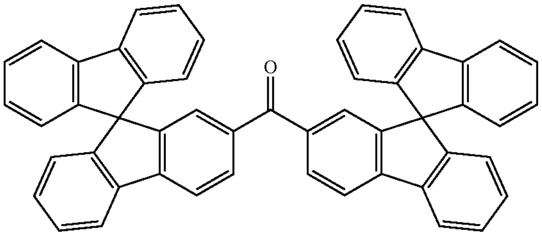
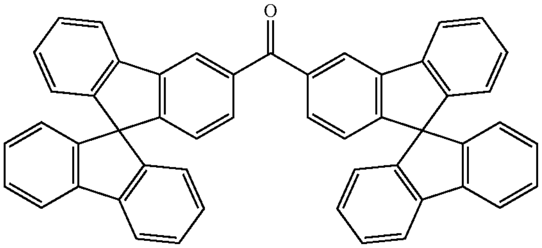
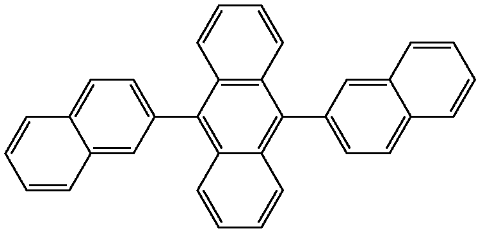
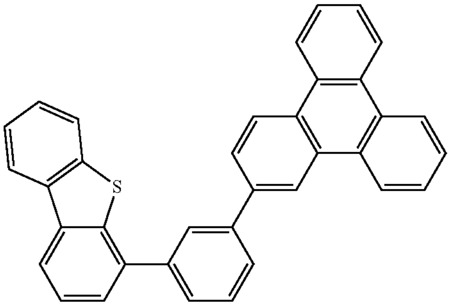

-continued

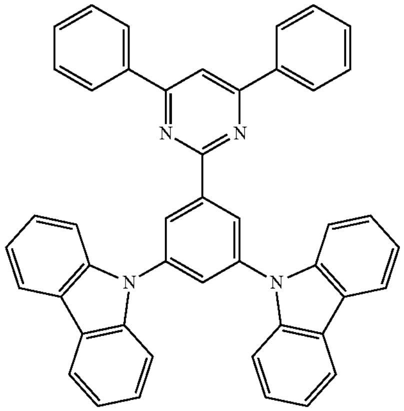

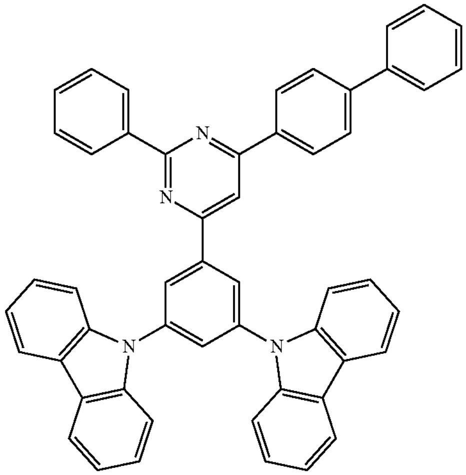

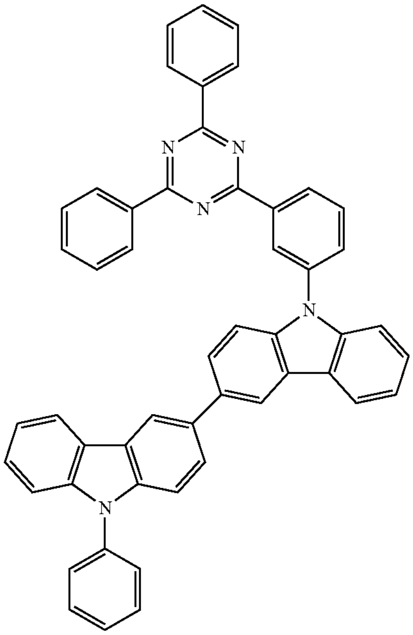

-continued

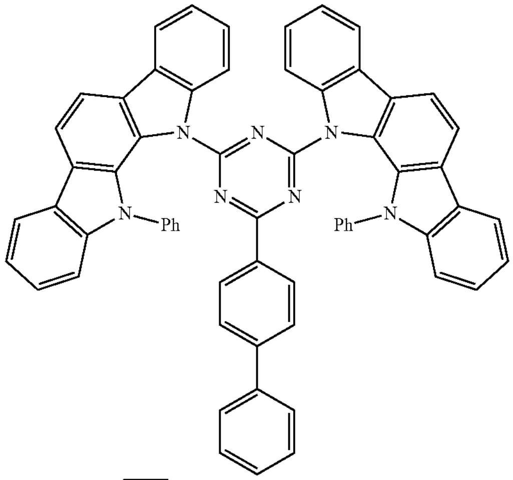

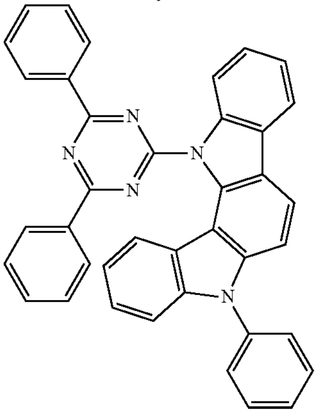

In some embodiments, the light emitting layer contains at least two TADF molecules differing in the structure. For example, the light emitting layer can contain three kinds of materials, a host material, a first TADF molecule and a second TADF molecule whose excited singlet energy level is higher in that order. At that time, the first TADF molecule and the second TADF molecule are preferably such that the difference $\Delta E_{ST}$ between the lowest excited singlet energy level and the lowest excited triplet energy level at 77 K thereof is 0.3 eV or less, more preferably 0.25 eV or less, even more preferably 0.2 eV or less, further more preferably 0.15 eV or less, further more preferably 0.1 eV or less, further more preferably 0.07 eV or less, further more preferably 0.05 eV or less, further more preferably 0.03 eV or less, especially more preferably 0.01 eV or less. The content of the first TADF molecule in the light emitting layer is preferably larger than the content of the second TADF molecule therein. The content of the host material in the light emitting layer is preferably larger than the content of the second TADF molecule therein. The content of the first TADF molecule in the light emitting layer can be larger than the content of the host material therein, or can be smaller than or the same as the latter. In some embodiments, the composition in the light emitting layer can be 10 to 70% by weight of the host material, 10 to 80% by weight of the first TADF molecule, and 0.1 to 30% by weight of the second TADF molecule. In some embodiments, the composition in the light emitting layer can be 20 to 45% by weight of the host material, 50 to 75% by weight of the first TADF molecule, and 5 to 20% by weight of the second TADF molecule. In some embodiments, the photoluminescence quantum yield φPL1(A) by photoexcitation of the co-deposited film of the first TADF molecule and the host material (the content of the first TADF molecule in the co-deposited film=A % by weight) and the photoluminescence quantum yield φPL2(A) by photoexcitation of the co-deposited film of the second TADF molecule and the host material (the content of the second TADF molecule in the co-deposited film=A % by weight) satisfy a relational formula φPL1(A)>φPL2(A). In some embodiments, the photoluminescence quantum yield φPL2(B) by photoexcitation of the co-deposited film of the second TADF molecule and the host material (the content of the second TADF molecule in the co-deposited film=B % by weight) and the photoluminescence quantum yield φPL2(100) by photoexcitation of the single film of the second TADF molecule satisfy a relational formula φPL2(B)>φPL2(100). In some embodiments, the light emitting layer can contain three TADF molecules differing in the structure. The compound in the present invention can be any of plural TADF compounds contained in the light emitting layer.

In some embodiments, the light emitting layer can be composed of a material selected from the group including a host material, an assist dopant and a light emitting material. In some embodiments, the light emitting layer does not contain a metal element. In some embodiments, the light emitting layer can be composed of a material composed of atoms alone selected from the group consisting of a carbon atom, a hydrogen atom, a nitrogen atom, an oxygen atom and a sulfur atom. Or the light emitting layer can be composed of a material composed of atoms alone selected from the group consisting of a carbon atom, a hydrogen atom and a nitrogen atom.

When the light emitting layer contains any other TADF material than the compound of the present invention, the TADF material can be a known delayed fluorescent material. Preferred delayed fluorescent materials are compounds included in the general formulae described in WO2013/154064, paragraphs 0008 to 0048 and 0095 to 0133; WO2013/011954, paragraphs 0007 to 0047 and 0073 to 0085; WO2013/011955, paragraphs 0007 to 0033 and 0059 to 0066; WO2013/081088, paragraphs 0008 to 0071 and 0118 to 0133; JP 2013-256490 A, paragraphs 0009 to 0046 and 0093 to 0134; JP 2013-116975 A, paragraphs 0008 to 0020 and 0038 to 0040; WO2013/133359, paragraphs 0007 to 0032 and 0079 to 0084; WO2013/161437, paragraphs 0008 to 0054 and 0101 to 0121; JP 2014-9352 A, paragraphs 0007 to 0041 and 0060 to 0069; JP 2014-9224 A, paragraphs 0008 to 0048 and 0067 to 0076; JP 2017-119663 A, paragraphs 0013 to 0025; JP 2017-119664 A, paragraphs 0013 to 0026; JP 2017-222623 A, paragraphs 0012 to 0025; JP 2017-226838 A, paragraphs 0010 to 0050; JP 2018-100411 A, paragraphs 0012 to 0043; WO2018/047853, paragraphs 0016 to 0044; and exemplary compounds therein capable of emitting delayed fluorescence are especially preferred. In addition, light-emitting materials capable of emitting delayed fluorescence, as described in JP 2013-253121 A, WO2013/133359, WO2014/034535, WO2014/115743, WO2014/122895, WO2014/126200, WO2014/136758, WO2014/133121, WO2014/136860, WO2014/196585, WO2014/189122, WO2014/168101, WO2015/008580, WO2014/203840, WO2015/002213, WO2015/016200, WO2015/019725, WO2015/072470, WO2015/108049, WO2015/080182, WO2015/072537, WO2015/080183, JP 2015-129240 A, WO2015/129714, WO2015/129715, WO2015/133501, WO2015/136880, WO2015/137244, WO2015/137202, WO2015/137136, WO2015/146541 and WO2015/159541, are also preferably employed. These patent publications described in this paragraph are hereby incorporated as a part of this description by reference.

Substrate:

In some embodiments, the organic electroluminescent device of the invention is supported by a substrate, wherein the substrate is not particularly limited and may be any of those that have been commonly used in an organic electroluminescent device, for example those formed of glass, transparent plastics, quartz and silicon.

Anode

In some embodiments, the anode of the organic electroluminescent device is made of a metal, an alloy, an electroconductive compound, or a combination thereof. In some embodiments, the metal, alloy, or electroconductive compound has a large work function (4 eV or more). In some embodiments, the metal is Au. In some embodiments, the electroconductive transparent material is selected from CuI, indium tin oxide (ITO), SnO2, and ZnO. In some embodiments, an amorphous material capable of forming a transparent electroconductive film, such as IDIXO ($In_2O_3$—ZnO), is be used. In some embodiments, the anode is a thin film. In some embodiments the thin film is made by vapor deposition or sputtering. In some embodiments, the film is patterned by a photolithography method. In some embodiments, where the pattern may not require high accuracy (for example, approximately 100 μm or more), the pattern may be formed with a mask having a desired shape on vapor deposition or sputtering of the electrode material. In some embodiments, when a material can be applied as a coating, such as an organic electroconductive compound, a wet film forming method, such as a printing method and a coating method is used. In some embodiments, when the emitted light goes through the anode, the anode has a transmittance of more than 10%, and the anode has a sheet resistance of several hundred. Ohm per square or less. In some embodiments, the thickness of the anode is from 10 to 1,000 nm. In some embodiments, the thickness of the anode is from 10 to 200 nm. In some embodiments, the thickness of the anode varies depending on the material used.

Cathode

In some embodiments, the cathode is made of an electrode material a metal having a small work function (4 eV or less) (referred to as an electron injection metal), an alloy, an electroconductive compound, or a combination thereof. In some embodiments, the electrode material is selected from sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. In some embodiments, a mixture of an electron injection metal and a second metal that is a stable metal having a larger work function than the electron injection metal is used. In some embodiments, the mixture is selected from a magnesium-silver mixture, a magnesium-aluminum mixture, a magnesium-indium mixture, an aluminum-aluminum oxide ($Al_2O_3$) mixture, a lithium-aluminum mixture, and aluminum. In some embodiments, the mixture increases the electron injection property and the durability against oxidation. In some embodiments, the cathode is produced by forming the electrode material into a thin film by vapor deposition or sputtering. In some embodiments, the cathode has a sheet resistance of several hundred Ohm per square or less. In some embodiments, the thickness of the cathode ranges from 10 nm to 5 μm. In some embodiments, the thickness of the cathode ranges from 50 to 200 nm. In some embodiments, for transmitting the emitted light, any one of the anode and the cathode of the organic electroluminescent device is transparent or translucent. In some embodiments, the transparent or translucent electroluminescent devices enhances the light emission luminance.

In some embodiments, the cathode is formed with an electroconductive transparent material, as described for the anode, to form a transparent or translucent cathode. In some embodiments, a device comprises an anode and a cathode, both being transparent or translucent.

Injection Layer

An injection layer is a layer between the electrode and the organic layer. In some embodiments, the injection layer decreases the driving voltage and enhances the light emission luminance. In some embodiments the injection layer includes a hole injection layer and an electron injection layer. The injection layer can be positioned between the anode and the light-emitting layer or the hole transporting layer, and between the cathode and the light-emitting layer or the electron transporting layer. In some embodiments, an injection layer is present. In some embodiments, no injection layer is present.

Preferred compound examples for use as a hole injection material are shown below.

$MoO_3$,

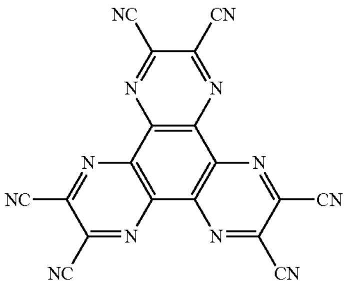

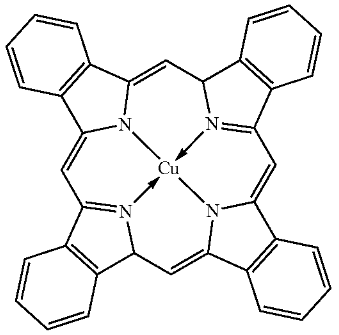

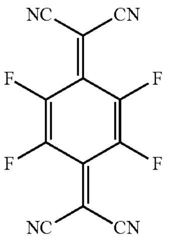

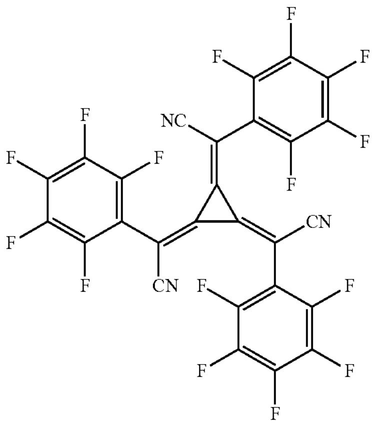

-continued

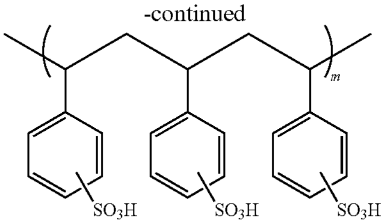

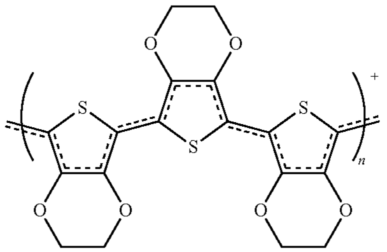

Next, preferred compound examples for use as an electron injection material are shown below.

LiF, CsF,

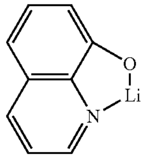

Barrier Layer

A barrier layer is a layer capable of inhibiting charges (electrons or holes) and/or excitons present in the light-emitting layer from being diffused outside the light-emitting layer. In some embodiments, the electron barrier layer is between the light-emitting layer and the hole transporting layer, and inhibits electrons from passing through the light-emitting layer toward the hole transporting layer. In some embodiments, the hole barrier layer is between the light-emitting layer and the electron transporting layer, and inhibits holes front passing through the light-emitting layer toward the electron transporting layer. In some embodiments, the barrier layer inhibits excitons from being diffused outside the light-emitting layer. In some embodiments, the electron barrier layer and the hole barrier layer are exciton barrier layers. As used herein, the term "electron barrier layer" or "exciton barrier layer" includes a layer that has the functions of both electron barrier layer and of an exciton barrier layer.

Hole Barrier Layer

A hole barrier layer acts as an electron transporting layer. In some embodiments, the hole barrier layer inhibits holes from reaching the electron transporting layer while transporting electrons. In some embodiments, the hole barrier layer enhances the recombination probability of electrons and holes in the light-emitting layer. The material for the hole barrier layer may be the same materials as the ones described for the electron transporting layer.

Preferred compound examples for use for the hole barrier layer are shown below.

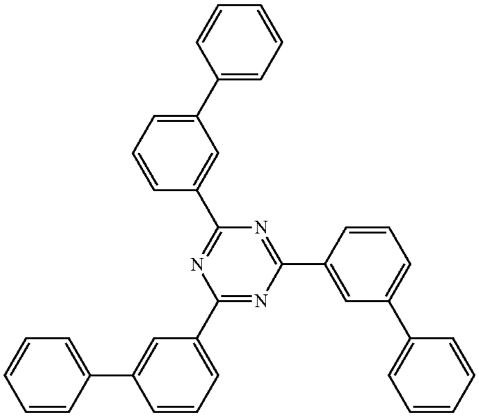

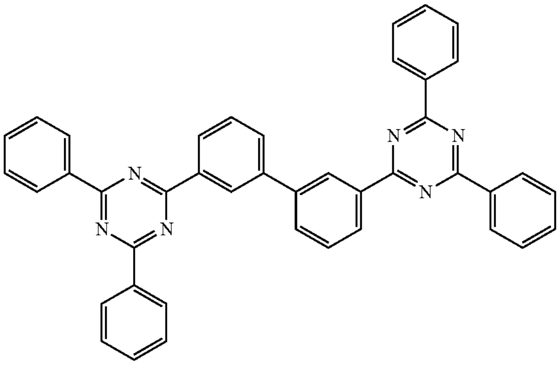

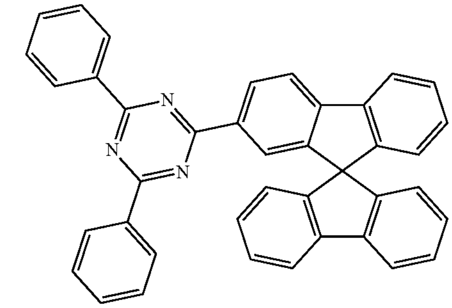

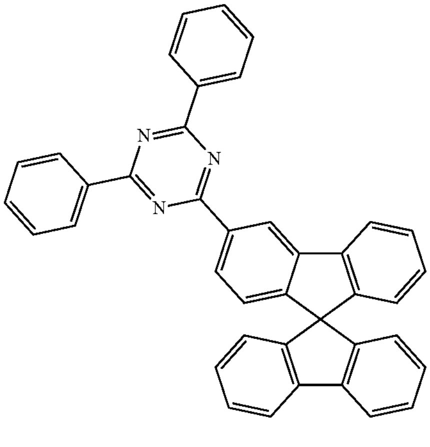

-continued

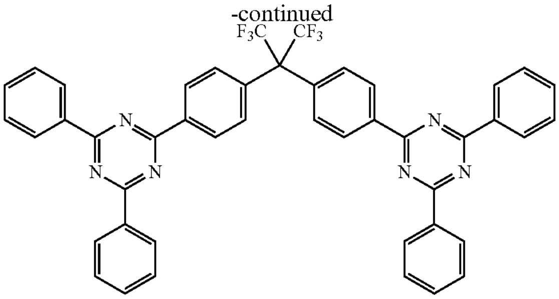

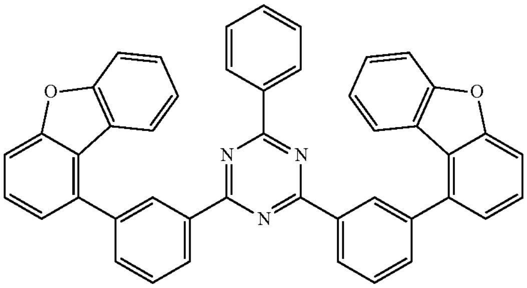

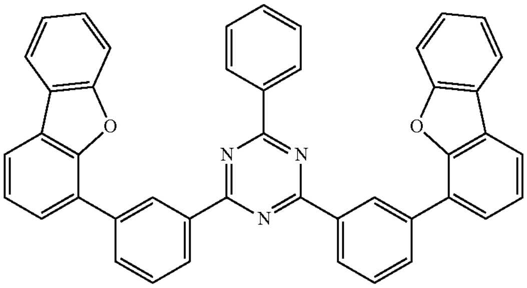

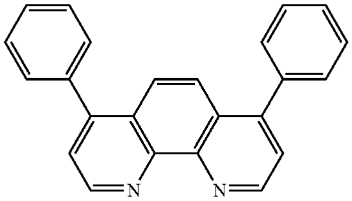

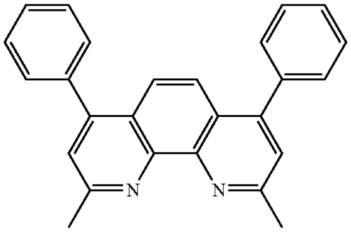

Electron Barrier Layer

As electron barrier layer transports holes. In some embodiments, the electron barrier layer inhibits electrons from reaching the hole transporting layer while transporting holes. In some embodiments, the electron barrier layer enhances the recombination probability of electrons and holes in the light-emitting layer. The material for use for the electron barrier layer can be the same as that mentioned hereinabove for the hole transporting layer.

Preferred compound examples for use as the electron barrier material are shown below.
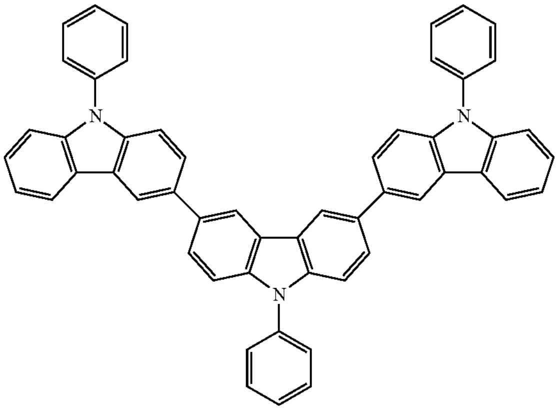
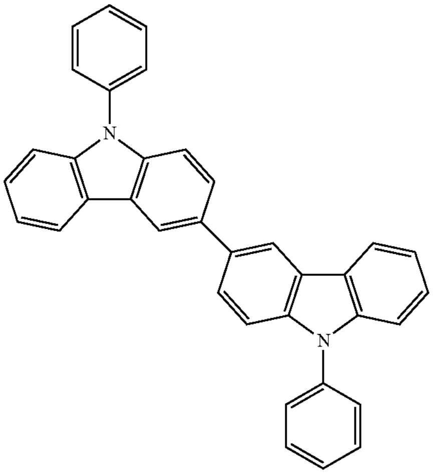
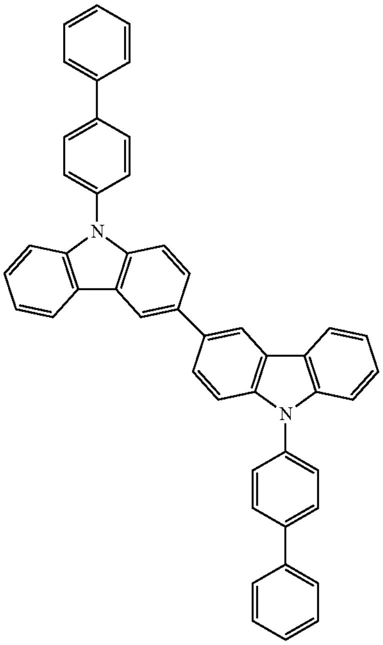
-continued
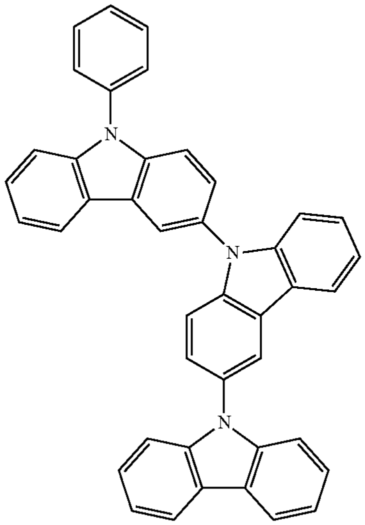
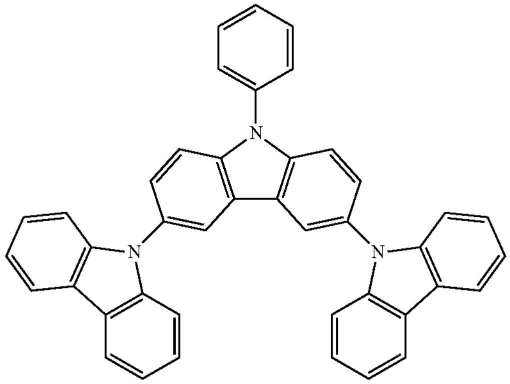
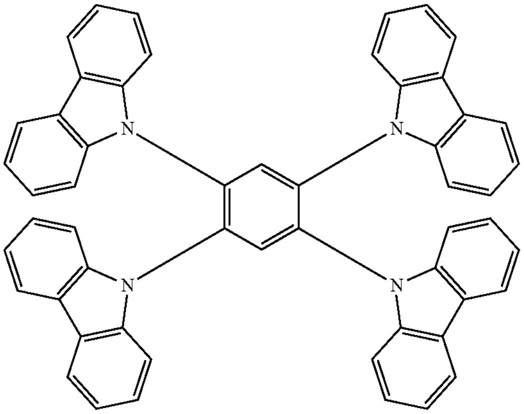

-continued

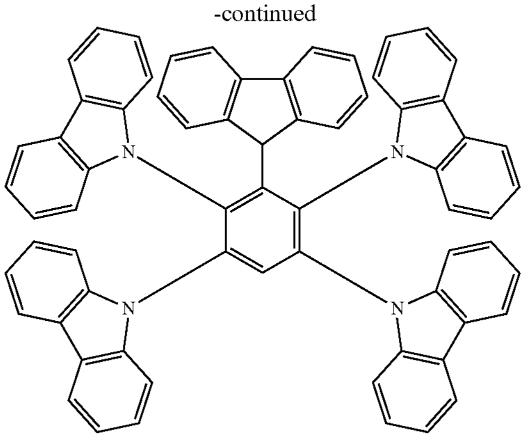

Exciton Barrier Layer

An exciton barrier layer inhibits excitons generated through recombination of holes and electrons in the light-emitting layer from being diffused to the charge transporting layer. In some embodiments, the exciton barrier layer enables effective confinement of excitons in the light-emitting layer. In some embodiments, the light emission efficiency of the device is enhanced. In some embodiments, the exciton barrier layer is adjacent to the light-emitting layer on any of the side of the anode and the side of the cathode, and on both the sides. In some embodiments, where the exciton barrier layer is on the side of the anode, the layer can be between the hole transporting layer and the light-emitting layer and adjacent to the light-emitting layer. In some embodiments, where the exciton barrier layer is on the side of the cathode, the layer can be between the light-emitting layer and the cathode and adjacent to the light-emitting layer. In some embodiments, a hole injection layer, an electron barrier layer, or a similar layer is between the anode and the exciton barrier layer that is adjacent to the light-emitting layer on the side of the anode. In some embodiments, a hole injection layer, an electron barrier layer, a hole barrier layer, or a similar layer is between the cathode and the exciton barrier layer that is adjacent to the light-emitting layer on the side of the cathode. In some embodiments, the exciton barrier layer comprises excited singlet energy and excited triplet energy, at least one of which is higher than the excited singlet energy and the excited triplet energy of the light-emitting material, respectively.

Hole Transporting Layer

The hole transporting layer comprises a hole transporting material. In some embodiments, the hole transporting layer is a single layer. In some embodiments, the hole transporting layer comprises a plurality layers.

In some embodiments, the hole transporting material has one of injection or transporting property of holes and barrier property of electrons. In some embodiments, the hole transporting material is an organic material. In some embodiments, the hole transporting material is an inorganic material. Examples of known hole transporting materials that may be used herein include but are not limited to a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer, or a combination thereof. In some embodiments, the hole transporting material is selected from a porphyrin compound, an aromatic tertiary amine compound, and a styrylamine compound. In some embodiments, the hole transporting material is an aromatic tertiary amine compound. Preferred compound examples for use as the hole transporting material are shown below.

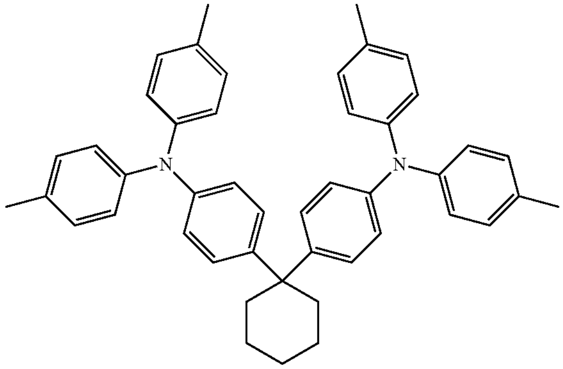

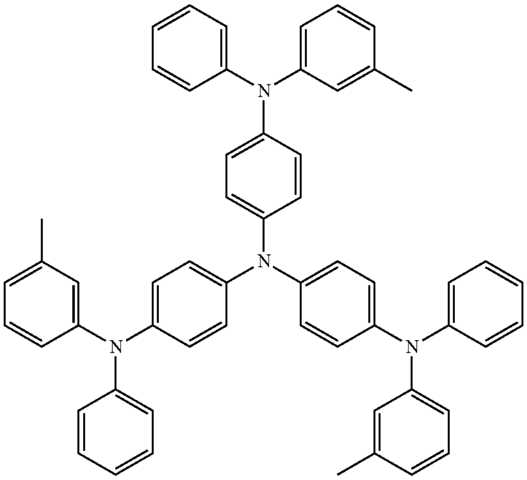

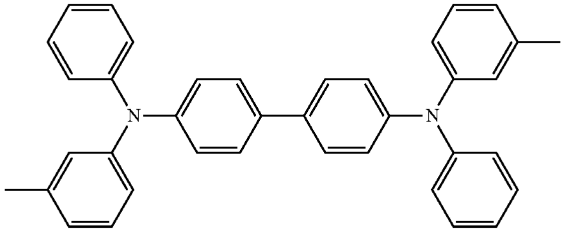

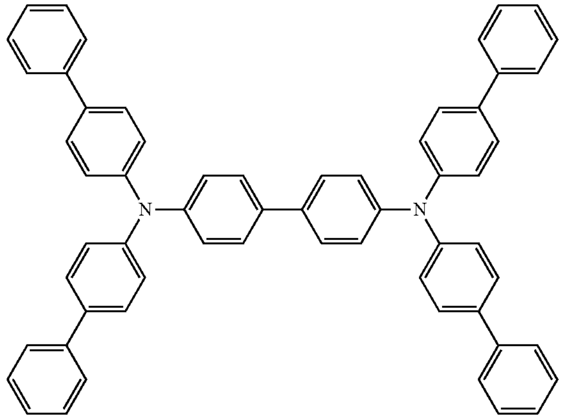

-continued
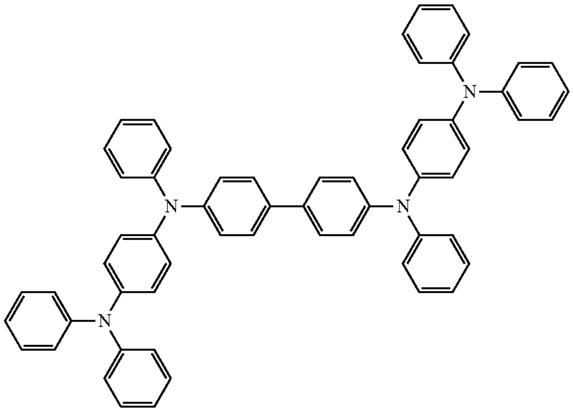
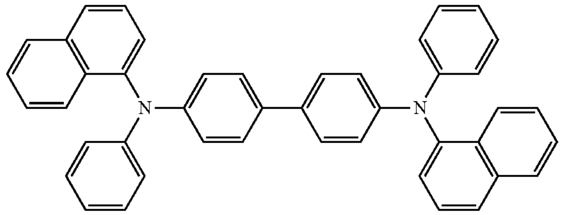
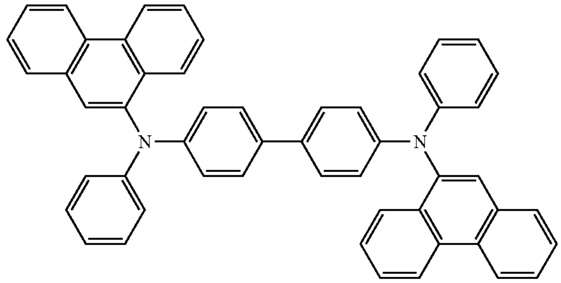
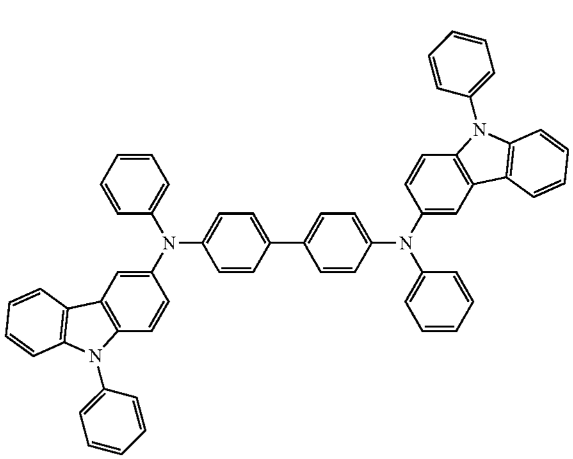
-continued
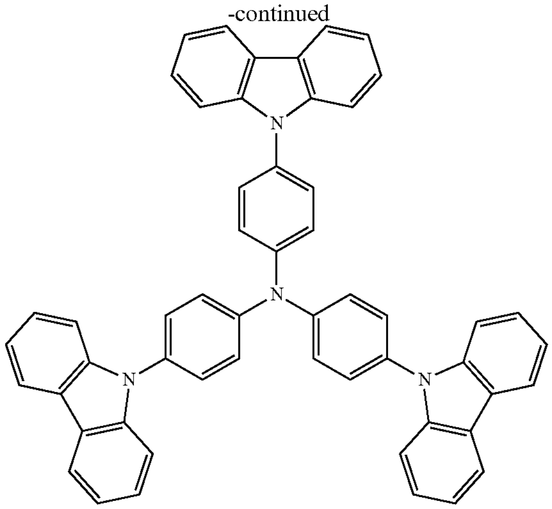
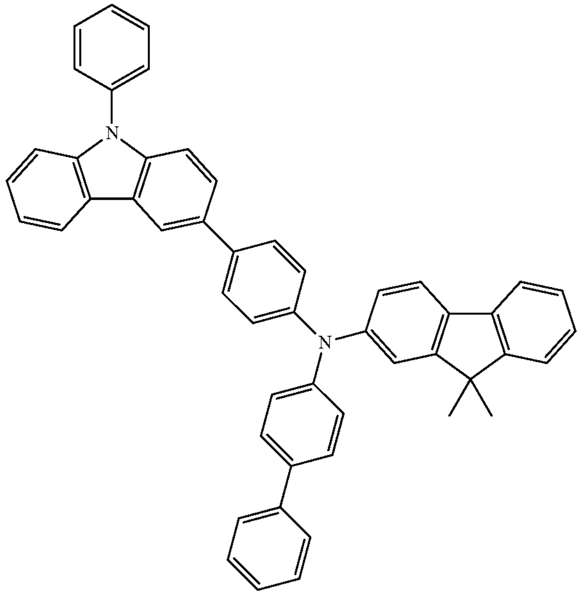
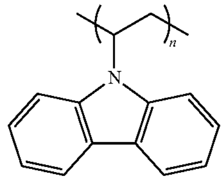
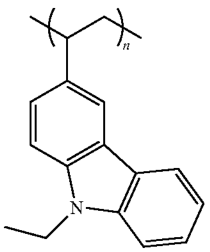
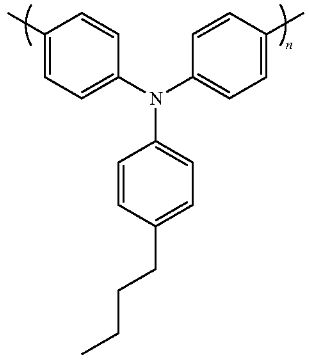

Electron Transporting Layer

The electron transporting layer comprises an electron transporting material. In some embodiments, the electron transporting layer is a single layer. In some embodiments, the electron transporting layer comprises a plurality of layer.

In some embodiments, the electron transporting material needs only to have a function of transporting electrons, which are injected from the cathode, to the light-emitting layer. In some embodiments, the electron transporting material also functions as a hole barrier material. Examples of the electron transporting layer that may be used herein include but are not limited to a nitro-substituted fluorene derivative, a diphenylquinone derivative, a thiopyran dioxide derivative, carbodiimide, a fluorenylidene methane derivative, anthraquinodimethane, an anthrone derivatives, an oxadiazole derivative, an azole derivative, an azine derivative, or a combination thereof, or a polymer thereof. In some embodiments, the electron transporting material is a thiadiazole derivative, or a quinoxaline derivative. In some embodiments, the electron transporting material is a polymer material. Preferred compound examples for use as the electron transporting material are shown below.

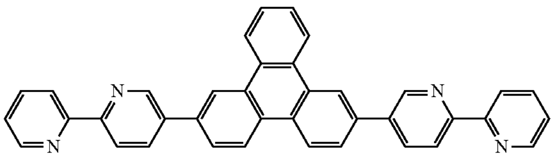

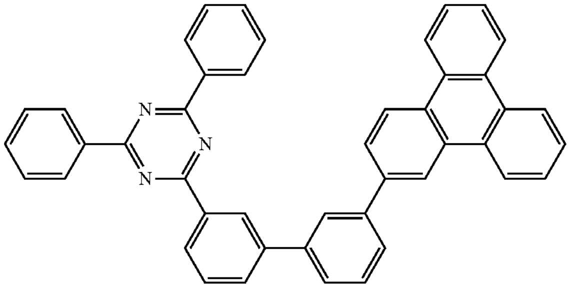

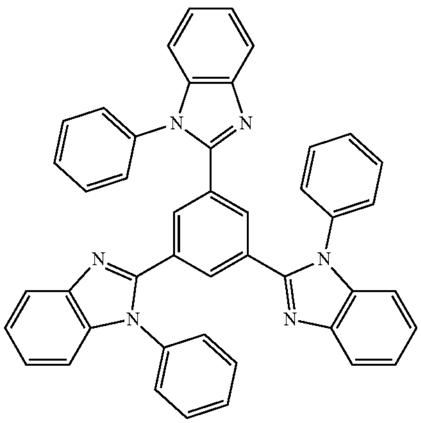

-continued

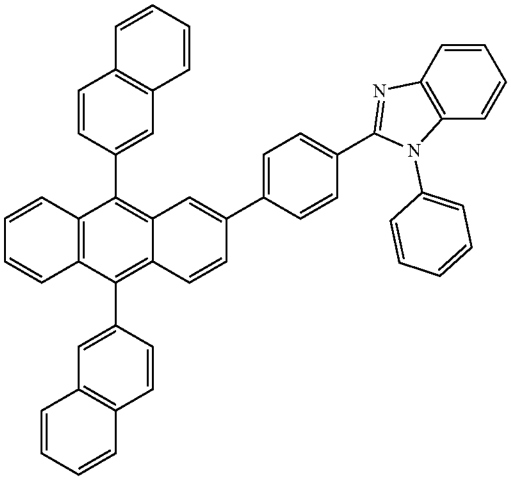

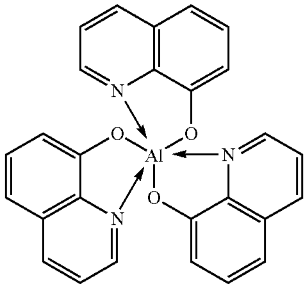

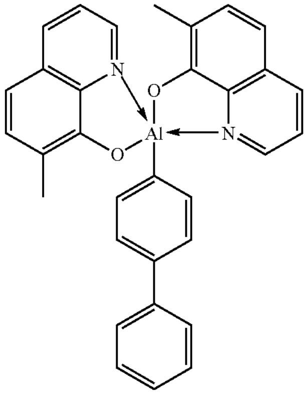

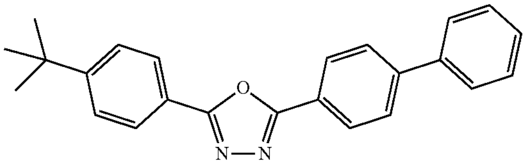

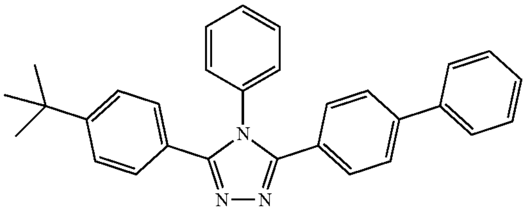

Hereinunder compound examples preferred as a material that can be added to the organic layers are shown. For example, these can be added as a stabilization material.

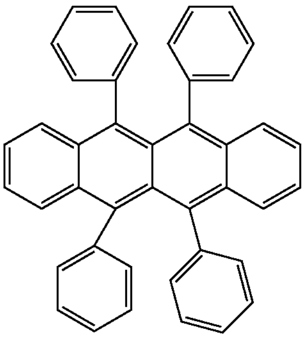

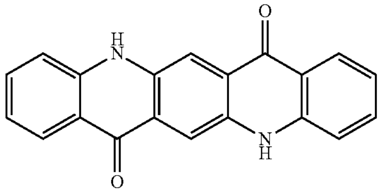

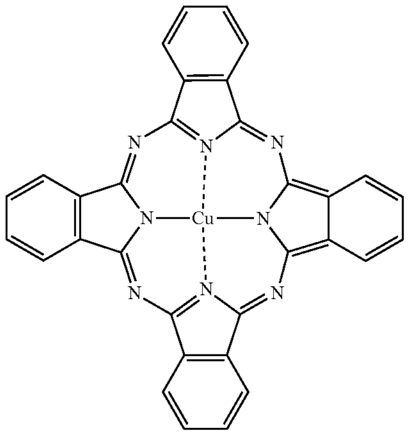

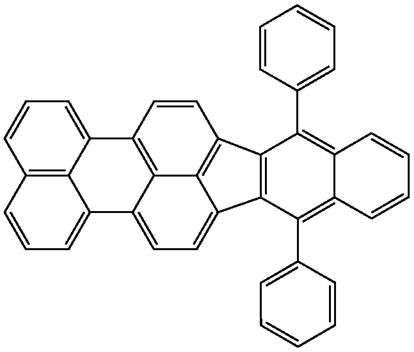

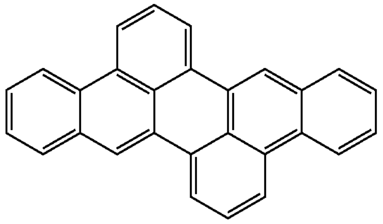

Preferred materials for use in the organic electroluminescent device are specifically shown. However, the materials usable in the invention should not be limitatively interpreted by the following exemplary compounds. Compounds that are exemplified as materials having a specific function can also be used as materials having any other function.

[Devices]

In some embodiments, the compound of this disclosure is incorporated into a device. For example, the device includes, but is not limited to an OLED bulb, an OLED lamp, a television screen, a computer monitor, a mobile phone, and a tablet.

In some embodiments, an electronic device contains an OLED that contains an anode, a cathode, and at least one organic layer containing a light emitting layer between the anode and the cathode, and the light emitting layer contains a host material and the compound represented by the general formula (1).

In some embodiments, in the light emitting layer of OLED, the compound represented by the general formula (1) is a fluorescent material and therefore the layer further contains a fluorescent material that converts a triplet to a singlet.

In some embodiments, compositions described herein may be incorporated into various light-sensitive or light-activated devices, such as OLEDs or photovoltaic devices. In some embodiments, the composition may be useful in facilitating charge transfer or energy transfer within a device and/or as a hole-transporting material. The device may be, for example, an organic light-emitting diode (OLED); an organic integrated circuit (OIC), an organic field-effect transistor (O-FET), an organic thin-film transistor (O-TFT); an organic light-emitting transistor (O-LET), an organic solar cell (O-SC), an organic optical detector, an organic photoreceptor, an organic field-quench device (O-FQD), a light-emitting electrochemical cell (LEC) or an organic laser diode (O-laser).

[Bulbs or Lamps]

In some embodiments, an electronic device comprises an OLED comprising an anode, a cathode, at least one organic layer comprising a light emitting layer between the anode and the cathode, and OLED driver circuit, and the light emitting layer contains a host material and the compound represented by the general formula (1) as a light emitting material.

In some embodiments, a device comprises OLEDs that differ in color. In some embodiments, a device comprises an array comprising a combination of OLEDs. In some embodiments, the combination of OLEDs is a combination of three colors (e.g., RGB). In some embodiments, the combination of OLEDs is a combination of colors that are not red, green, or blue (for example, orange and yellow green). In some embodiments, the combination of OLEDs is a combination of two, four, or more colors.

In some embodiments, a device is an OLED light comprising (1) a circuit board having a first side with a mounting surface and an opposing second side, and defining at least one aperture; (2) at least one OLED on the mounting surface, the at least one OLED configured to emanate light, comprising an anode, a cathode, and at least one organic layer comprising a light emitting layer between the anode and the cathode, in which the light emitting layer contains a host material and the compound represented by the general formula (1) as a light emitting material; (3) a housing for the circuit board; and (4) at least one connector arranged at an end of the housing, the housing and the connector defining a package adapted for installation in a light fixture.

In some embodiments, the OLED light comprises a plurality of OLEDs mounted on a circuit board such that light emanates in a plurality of directions. In some embodiments, a portion of the light emanated in a first direction is deflected to emanate in a second direction. In some embodiments, a reflector is used to deflect the light emanated in a first direction.

[Principle of OLED]

OLEDs are typically composed of a layer of organic materials or compounds between two electrodes, an anode and a cathode. The organic molecules are electrically conductive as a result of delocalization of π electronics caused by conjugation over part or all of the molecule. When voltage is applied, electrons from the highest occupied molecular orbital (HOMO) present at the anode flow into the lowest unoccupied molecular orbital (LUMO) of the organic molecules present at the cathode. Removal of electrons from the HOMO is also referred to as inserting electron holes into the HOMO. Electrostatic forces bring the electrons and the holes towards each other until they recombine and form an exciton (which is the bound state of the electron and the hole). As the excited state decays and the energy levels of the electrons relax, radiation having a frequency in the visible spectrum is emitted. The frequency of this radiation depends on the band gap of the material, which is the difference in energy between the HOMO and the LUMO.

As electrons and holes are fermions with half integer spin, an exciton may either be in a singlet state or a triplet state depending on how the spins of the electron and hole have been combined. Statistically, three triplet excitons will be formed for each singlet exciton. Decay from triplet states is spin forbidden, which results in increases in the timescale of the transition and limits the internal efficiency of fluorescent devices. Phosphorescent organic light-emitting diodes make use of spin-orbit interactions to facilitate intersystem crossing between singlet and triplet states, thus obtaining emission from both singlet and triplet states and improving the internal efficiency.

One prototypical phosphorescent material is iridium tris (2-phenylpyridine) ($Ir(ppy)_3$) in which the excited state is a charge transfer from the Ir atom to the organic ligand. Such approaches have reduced the triplet lifetime to about several us, several orders of magnitude slower than the radiative lifetimes of fully-allowed transitions such as fluorescence. Ir-based phosphors have proven to be acceptable for many display applications, but losses due to large triplet densities still prevent the application of OLEDs to solid-state lighting at higher brightness.

Thermally activated delayed fluorescence (TADF) seeks to minimize energetic splitting between singlet and triplet states ($\Delta E_{ST}$). The reduction in exchange splitting from typical values of 0.4-0.7 eV to a gap of the order of the thermal energy (proportional to kBT, where kB represents the Boltzmann constant, and T represents temperature) means that thermal agitation can transfer population between singlet levels and triplet levels in a relevant timescale even if the coupling between states is small.

TADF molecules consist of donor and acceptor moieties connected directly by a covalent bond or via a conjugated linker (or “bridge”). A “donor” moiety is likely to transfer electrons from its HOMO upon excitation to the “acceptor” moiety. An “acceptor” moiety is likely to accept the electrons from the “donor” moiety into its LUMO. The donor-acceptor nature of TADF molecules results in low-lying excited states with charge-transfer character that exhibit very low $\Delta E_{ST}$. Since thermal molecular motions can randomly vary the optical properties of donor-acceptor systems, a rigid three-dimensional arrangement of donor and acceptor moieties can be used to limit the non-radiative decay of the charge-transfer state by internal conversion during the lifetime of the excitation.

It is beneficial, therefore, to decrease $\Delta E_{ST}$, and to create a system with increased reversed intersystem crossing (RISC) capable of exploiting triplet excitons. Such a system, it is believed, will result in increased quantum efficiency and decreased emission lifetimes. Systems with these features will be capable of emitting light without being subject to the rapid degradation prevalent in OLEDs known today.

[Displays or Screens]

In some embodiments, the compound represented by the general formula (1) can be used in a screen or a display. In some embodiments, the compound represented by the general formula (1) is deposited onto a substrate using a process including, but not limited to, vacuum evaporation, deposition, vapor deposition, or chemical vapor deposition (CVD). In some embodiments, the substrate is a photoplate structure useful in a two-sided etch that provides a unique aspect ratio pixel. The screen (which may also be referred to as a mask) is used in a process in the manufacturing of OLED displays. The corresponding artwork pattern design facilitates a very steep and narrow tie-bar between the pixels in the vertical direction and a large, sweeping bevel opening in the horizontal direction. This allows the close patterning of pixels needed for high definition displays while optimizing the chemical deposition onto a TFT backplane.

The internal patterning of the pixel allows the construction of a 3-dimensional pixel opening with varying aspect ratios in the horizontal and vertical directions. Additionally, the use of imaged “stripes” or halftone circles within the pixel area inhibits etching in specific areas until these specific patterns are undercut and fall off the substrate. At that point the entire pixel area is subjected to a similar etch rate but the depths are varying depending on the halftone pattern. Varying the size and spacing of the halftone pattern allows etching to be inhibited at different rates within the pixel allowing for a localized deeper etch needed to create steep vertical bevels.

A preferred material for the deposition mask is invar. Invar is a metal alloy that is cold rolled into long thin sheet in a steel mill. Invar cannot be electrodeposited onto a rotating mandrel as the nickel mask. A preferred and more cost feasible method for forming the open areas in the mask used for deposition is through a wet chemical etching.

In some embodiments, a screen or display pattern is a pixel matrix on a substrate. In some embodiments, a screen or display pattern is fabricated using lithography (e.g., photolithography and e-beam lithography). In some embodiments, a screen or display pattern is fabricated using a wet chemical etch. In further embodiments, a screen or display pattern is fabricated using plasma etching.

[Methods of Manufacturing Devices Using the Disclosed Compounds]

An OLED display is generally manufactured by forming a large mother panel and then cutting the mother panel in units of cell panels. In general, each of the cell panels on the mother panel is formed by forming a thin film transistor (TFT) including an active layer and a source/drain electrode on a base substrate, applying a planarization film to the TFT, and sequentially forming a pixel electrode, a light-emitting layer, a counter electrode, and an encapsulation layer, and then is cut from the mother panel.

An OLED display is generally manufactured by forming a large mother panel and then cutting the mother panel in units of cell panels. In general, each of the cell panels on the mother panel is formed by forming a thin film transistor (TFT) including an active layer and a source/drain electrode on a base substrate, applying a planarization film to the TFT, and sequentially forming a pixel electrode, a light-emitting layer, a counter electrode, and an encapsulation layer, and then is cut from the mother panel.

In another aspect, provided herein is a method of manufacturing an organic light-emitting diode (OLED) display, the method including: forming a barrier layer on a base substrate of a mother panel; forming a plurality of display units in units of cell panels on the barrier layer; forming an encapsulation layer on each of the display units of the cell panels; and applying an organic film to an interface portion between the cell panels.

In some embodiments, the barrier layer is an inorganic film formed of, for example, SiNx, and an edge portion of the barrier layer is covered with an organic film formed of polyimide or acryl. In some embodiments, the organic film helps the mother panel to be softly cut in units of the cell panel.

In some embodiments, the thin film transistor (TFT) layer includes a light-emitting layer, a gate electrode, and a source/drain electrode. Each of the plurality of display units may include a thin film transistor (TFT) layer, a planarization film formed on the TFT layer, and a light-emitting unit formed on the planarization film, wherein the organic film applied to the interface portion is formed of a same material as a material of the planarization film and is formed at a same time as the planarization film is formed. In some embodiments, a light-emitting unit is connected to the TFT layer with a passivation layer and a planarization film therebetween and an encapsulation layer that covers and protects the light-emitting unit. In some embodiments of the method of manufacturing, the organic film contacts neither the display units nor the encapsulation layer.

Each of the organic film and the planarization film may include any one of polyimide and acryl. In some embodiments, the barrier layer may be an inorganic film. In some embodiments, the base substrate may be formed of polyimide. The method may further include, before the forming of the barrier layer on one surface of the base substrate formed of polyimide, attaching a carrier substrate formed of a glass material to another surface of the base substrate, and before the cutting along the interface portion, separating the carrier substrate from the base substrate. In some embodiments, the OLED display is a flexible display.

In some embodiments, the passivation layer is an organic film disposed on the TFT layer to cover the TFT layer. In some embodiments, the planarization film is an organic film formed on the passivation layer. In some embodiments, the planarization film is formed of polyimide or acryl, like the organic film formed on the edge portion of the barrier layer. In some embodiments, the planarization film and the organic film are simultaneously formed when the OLED display is manufactured. In some embodiments, the organic film may be formed on the edge portion of the barrier layer such that a portion of the organic film directly contacts the base substrate and a remaining portion of the organic film contacts the barrier layer while surrounding the edge portion of the barrier layer.

In some embodiments, the light-emitting layer includes a pixel electrode, a counter electrode, and an organic light-emitting layer disposed between the pixel electrode and the counter electrode. In some embodiments, the pixel electrode is connected to the source/drain electrode of the TFT layer.

In some embodiments, when a voltage is applied to the pixel electrode through the TFT layer, an appropriate voltage is formed between the pixel electrode and the counter electrode, and thus the organic light-emitting layer emits light, thereby forming an image. Hereinafter, an image forming unit including the TFT layer and the light-emitting unit is referred to as a display unit.

In some embodiments, the encapsulation layer that covers the display unit and prevents penetration of external moisture may be formed to have a thin film encapsulation structure in which an organic film and an inorganic film are alternately stacked. In some embodiments, the encapsulation layer has a thin film encapsulation structure in which a plurality of thin films are stacked. In some embodiments, the organic film applied to the interface portion is spaced apart from each of the plurality of display units. In some embodiments, the organic film is formed such that a portion of the organic film directly contacts the base substrate and a remaining portion of the organic film contacts the barrier layer while surrounding an edge portion of the barrier layer.

In one embodiment, the OLED display is flexible and uses the soft base substrate formed of polyimide. In some embodiments, the base substrate is formed on a carrier substrate formed of a glass material, and then the carrier substrate is separated.

In some embodiments, the barrier layer is formed on a surface of the base substrate opposite to the carrier substrate. In one embodiment, the barrier layer is patterned according to a size of each of the cell panels. For example, while the base substrate is formed over the entire surface of a mother panel, the barrier layer is formed according to a size of each of the cell panels, and thus a groove is formed at an interface portion between the barrier layers of the cell panels. Each of the cell panels can be cut along the groove.

In some embodiments, the method of manufacture further comprises cutting along the interface portion, wherein a groove is formed in the barrier layer, wherein at least a portion of the organic film is formed in the groove, and wherein the groove does not penetrate into the base substrate. In some embodiments, the TFT layer of each of the cell panels is formed, and the passivation layer which is an inorganic film and the planarization film which is an organic film are disposed on the TFT layer to cover the TFT layer. At the same time as the planarization film formed of, for example, polyimide or acryl is formed, the groove at the interface portion is covered with the organic film formed of, for example, polyimide or acryl. This is to prevent cracks from occurring by allowing the organic film to absorb an impact generated when each of the cell panels is cut along the groove at the interface portion. That is, if the entire barrier layer is entirely exposed without the organic film, an impact generated when each of the cell panels is cut along the groove at the interface portion is transferred to the barrier layer, thereby increasing the risk of cracks. However, in one embodiment, since the groove at the interface portion between the barrier layers is covered with the organic film and the organic film absorbs an impact that would otherwise be transferred to the barrier layer, each of the cell panels may be softly cut and cracks may be prevented from occurring in the barrier layer. In one embodiment, the organic film covering the groove at the interface portion and the planarization film are spaced apart from each other. For example, if the organic film and the planarization film are connected to each other as one layer, since external moisture may penetrate into the display unit through the planarization film and a portion where the organic film remains, the organic film and the planarization film are spaced apart from each other such that the organic film is spaced apart from the display unit.

In some embodiments, the display unit is formed by forming the light-emitting unit, and the encapsulation layer is disposed on the display unit to cover the display unit. As such, once the mother panel is completely manufactured, the carrier substrate that supports the base substrate is separated from the base substrate. In some embodiments, when a laser beam is emitted toward the carrier substrate, the carrier substrate is separated from the base substrate due to a difference in a thermal expansion coefficient between the carrier substrate and the base substrate.

In some embodiments, the mother panel is cut in units of the cell panels. In some embodiments, the mother panel is cut along an interface portion between the cell panels by using a cutter. In some embodiments, since the groove at the interface portion along which the mother panel is cut is covered with the organic film, the organic film absorbs an impact during the cutting. In some embodiments, cracks may be prevented from occurring in the barrier layer during the cutting.

In some embodiments, the methods reduce a defect rate of a product and stabilize its quality.

Another aspect is an OLED display including: a barrier layer that is formed on a base substrate; a display unit that is formed on the barrier layer; an encapsulation layer that is formed on the display unit; and an organic film that is applied to an edge portion of the barrier layer.

EXAMPLES

The features of the present invention will be described more specifically with reference to Synthesis Examples and Examples given below. The materials, processes, procedures and the like shown below may be appropriately modified unless they deviate from the substance of the invention. Accordingly, the scope of the invention is not construed as being limited to the specific examples shown below. Sample characteristics were evaluated, using NMR (Bruker's nuclear magnetic resonance 500 MHz), LC/MS (Waters' liquid chromatography mass spectrometer), AC3 (by Riken Keiki), a high-performance UV/Vis/NIR spectrophotometer (Perkin Elmer's Lambda 950), a fluorescence spectrophotometer (Horiba's FluoroMax-4), a photonic multichannel analyzer (Hamamatsu Photonics' PMA-12 C10027-01), an absolute PL quantum yield measuring system (Hamamatsu Photonics' C11347), and an automatic current voltage luminance measuring system (System Engineering's ETS-170).

Synthesis Example 1

A compound 1 was synthesized according to the following scheme.

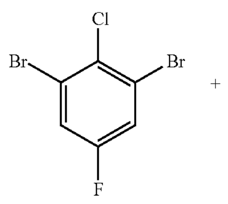

a

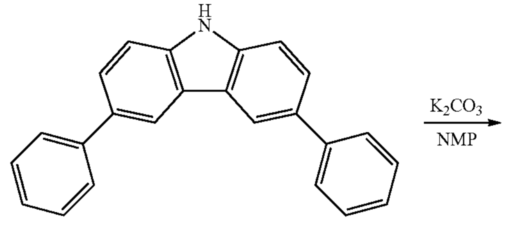

b

-continued

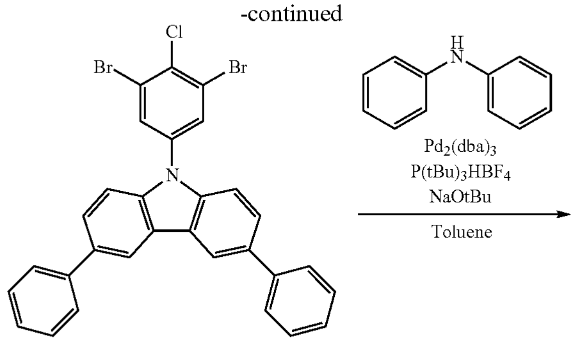

c

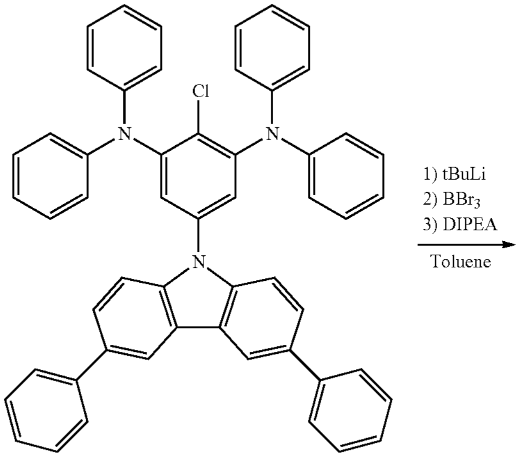

d

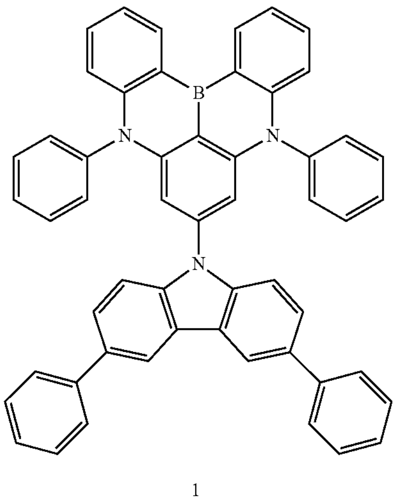

1

In a nitrogen stream, a compound a (5.0 g, 17.3 mmol) was added to an N-methyl-2-pyrrolidone (NMP) solution (52 mL) of a compound b (6.7 g, 20.8 mmol) and potassium carbonate (4.8 g, 34.7 mmol), and stirred at 10° C. for 15 hours. The mixture was restored to room temperature, water was added, and the precipitated solid was taken out through filtration. This was purified through silica gel column chromatography (dichloromethane/hexane=1/2) to give a white solid of a compound c (6.75 g, 11.5 mmol, yield 83%).

$^1H$ NMR (500 MHz, $CDCl_3$, δ): 8.38 (s, 2H), 7.91 (s, 2H), 7.74-7.71 (m, 6H), 7.51-7.48 (m, 6H), 7.37 (t, J=7.5 Hz, 2H)

ASAP Mass Spectrometry: theoretical 587.7, found 587.9.

Tri-t-butyl phosphine tetrafluoroborate (10 mg, 0.03 mmol), tris(dibenzylideneacetone)dipalladium(0) (16 mg, 0.02 mmol) and sodium t-butoxide (0.13 g, 1.4 mmol) were added to a toluene (1.4 mL) solution of the compound c (0.20 g. 0.34 mmol) and diphenylamine (0.10 g, 0.82 mmol) in a nitrogen stream, and stirred at 80° C. for 15 hours. The mixture was restored to room temperature, and filtered through Celite. The solvent was evaporated away from the filtrate, and methanol was added to the residue. The suspension was filtered, and the residue on the filter was washed with methanol. This was purified through silica gel column chromatography (dichloromethane/hexane=1/1) to give a white solid of a compound d (0.20 g, 0.26 mmol, yield 76%).

$^1$H NMR (500 MHz, $CDCl_3$, δ): 8.34 (s, 2H), 7.68 (d, J=7.5 Hz, 4H), 7.58 (d, J=8.5 Hz, 2H), 7.47 (t, J=7.5 Hz, 4H), 7.36 (t, J=8.5 Hz, 4H), 7.33 (s, 2H), 7.29 (t, J=8.0 Hz, 8H), 7.10 (t, J=8.0 Hz, 8H), 7.02 (t, J=7.5 Hz, 4H)

ASAP Mass Spectrometry: theoretical 763.3, found 764.4.

In a nitrogen stream, at 0° C., t-BuLi (1.9 mol/L, pentane solution, 2.1 mL, 3.9 mmol) was added to a toluene (39 mL) solution of a compound d (2.0 g, 2.6 mmol), and stirred at 90° C. for 1 hour. The reaction mixture was cooled to 0° C., tribromoboron (0.98 g, 3.9 mmol) was added, and stirred at room temperature for 30 minutes. N-ethyldiisopropylamine (0.68 g, 5.2 mmol) was added to the reaction solution, and stirred at 100° C. for 15 hours. The resultant reaction mixture was filtered through Celite, and the solvent was evaporated away from the filtrate. This was purified through silica gel column chromatography (ethyl acetate/hexane=1/9) to give a yellow solid of a compound 1 (0.73 g, 0.99 mmol, yield 38%).

$^1$H NMR (500 MHz, $CDCl_3$, δ): 9.02 (d, J=7.5 Hz, 2H), 8.27 (s, 2H), 7.69-7.64 (m, 8H), 7.54 (d, J=8.5 Hz, 2H), 7.51-7.45 (m, 12H), 7.38 (d, J=8.5 Hz, 2H), 7.34 (t, J=7.5 Hz, 4H), 6.83 (d, J=8.5 Hz, 2H), 6.38 (s, 2H)

ASAP Mass Spectrometry: theoretical 737.3, found 737.5.

Synthesis Example 2

A compound 2 was synthesized according to the following scheme.

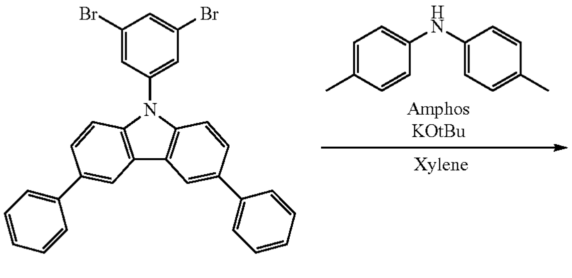

e

-continued

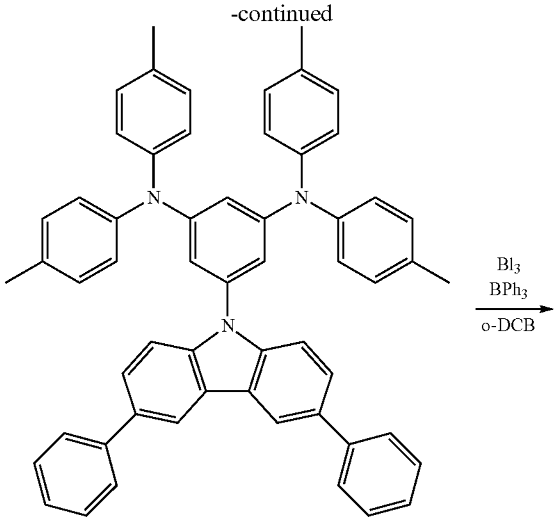

f

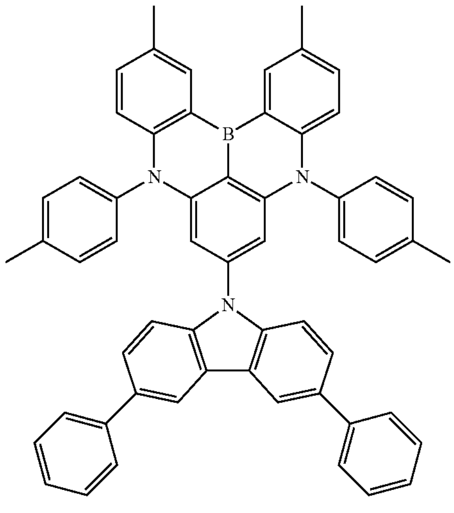

2

In a nitrogen stream, $PdCl_2(Am\text{-}phos)_2$ (Amphos: 16 mg, 0.020 mmol) and potassium t-butoxide (250 mg. 2.3 mmol) were added to a xylene (8 mL) solution of a compound e (415 mg, 0.75 mmol) and p,p'-ditolylamine (370 mg, 1.9 mmol), and stirred at 80° C. for 15 hours. The mixture was restored to room temperature, and the solvent was evaporated away. The residue was dissolved in dichloromethane, and methanol was added. The suspension was filtered, and the residue on the filtrate was washed with methanol. This was purified through silica gel column chromatography (toluene/hexane=1/1) to give a white solid of a compound f (410 mg. 0.53 mmol, yield 72%).

$^1$H NMR (500 MHz, $CDCl_3$, δ): 8.30 (s, 2H), 7.70 (d, J=8.0 Hz, 4H), 7.62 (d, J=8.5 Hz, 2H), 7.47 (t, J=8.5 Hz, 6H), 7.34 (t, J=7.5 Hz, 2H), 7.05 (m, 16H), 6.80 (s, 1H), 6.70 (s, 2H), 2.27 (s, 12H)

ASAP Mass Spectrometry: theoretical 786.4, found 786.5.

In a nitrogen stream, triiodoboron (390 mg, 1.0 mmol) and triphenylboron (920 mg, 0.80 mmol) were added to an o-dichlorobenzene (1.0 mL) solution of the compound f (310 mg, 0.40 mmol), and stirred at 150° C. for 15 hours. Water was added to the reaction solution, and extracted with toluene, and the resultant extract was washed with saturated saline water, dried with anhydrous magnesium sulfate, and the solvent was evaporated away. This was purified through silica gel column chromatography (ethyl acetate/hexane=1/20) to give a yellow solid of a compound 2 (46 mg. 0.060 mmol, yield 15%).

Compound 2: $^{1}$H NMR (500 MHz, $CDCl_3$, δ): 9.32 (s, 2H), 8.98 (s, 2H), 8.74 (s, 2H), 7.98 (d, J=7.0 Hz, 2H), 7.64 (t, J=7.5 Hz, 4H), 7.50-7.47 (m, 6H), 7.18-7.05 (m, 12H), 6.80 (d, J=8.5 Hz, 2H), 2.57 (s, 6H), 2.53 (s, 6H)

ASAP Mass Spectrometry: theoretical 794.4, found 794.5.

Synthesis Example 3

A compound 3 was synthesized according to the following scheme.

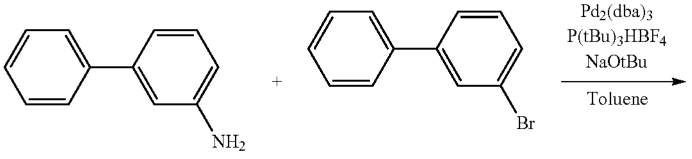

g h

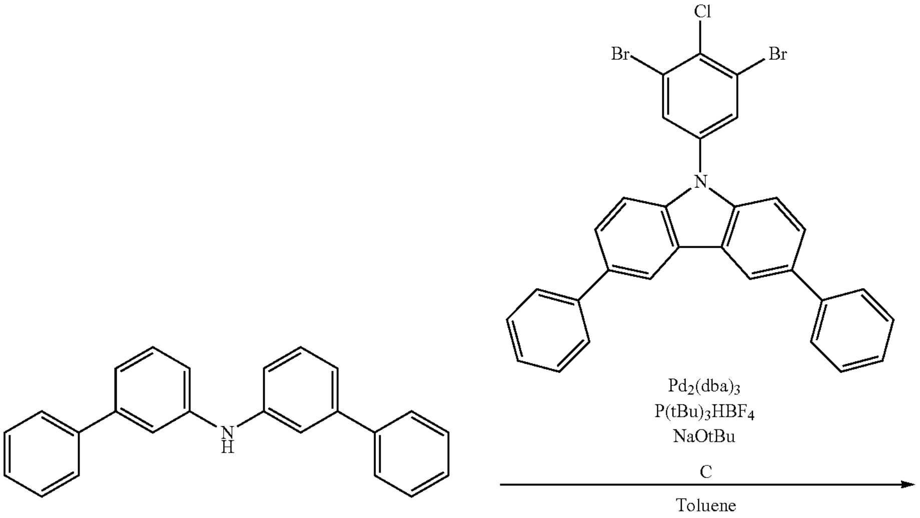

i

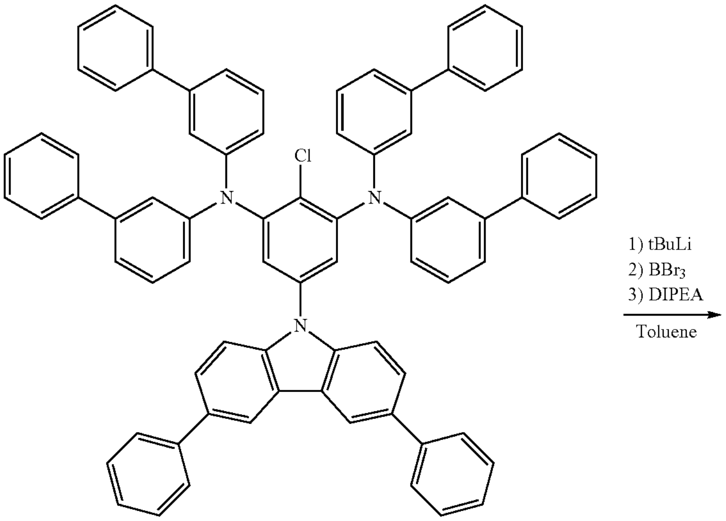

j

-continued

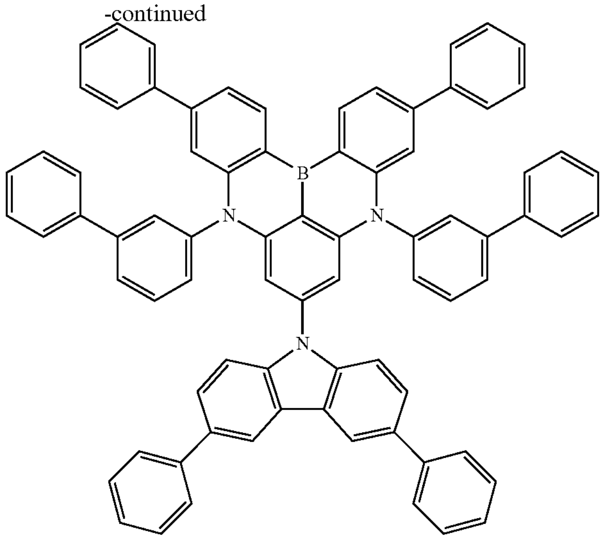

3

In a nitrogen stream, tri-t-butyl phosphine tetrafluoroborate (514 mg, 1.77 mmol), tris(dibenzylideneacetone)dipalladium(0) (810 mg, 0.89 mmol) and sodium t-butoxide (3.4 g, 36 mmol) were added to a toluene (36 mL) solution of 3-biphenylamine (compound g, 3.0 g, 18 mmol) and 3-bromobiphenyl (compound h, 3.7 g, 16.0 mmol), and stirred at 90° C. for 15 hours. The mixture was restored to room temperature, and filtered through Celite. The solvent was evaporated away from the filtrate, and the residue was purified through silica gel column chromatography (dichloromethane/hexane=1/3) to give a colorless liquid of a compound i (3.6 g, 11 mmol, yield 70%).

$^1$H NMR (500 MHz, $CDCl_3$, δ): 7.69 (d, J=7.5 Hz, 4H), 7.46 (t, J=7.5 Hz, 4H), 7.39-7.36 (m, 6H), 7.20 (d, J=7.5 Hz, 2H), 7.15 (d, J=7.5 Hz, 2H), 5.89 (brs, 1H)

ASAP Mass Spectrometry: theoretical 321.2, found 321.1.

In a nitrogen stream, tri-t-butyl phosphine tetrafluoroborate (120 mg, 0.43 mmol), tris(dibenzylideneacetone)dipalladium(0) (190 mg, 0.21 mmol) and sodium t-butoxide (1.6 g, 17.0 mmol) were added to a toluene (17 mL) solution of the compound c (2.5 g, 4.3 mmol) and the compound i (3.0 g, 9.4 mmol), and stirred at 90° C. for 15 hours. The mixture was restored to room temperature, and filtered through Celite. The solvent was evaporated away from the filtrate, and methanol was added to the residue. The suspension was filtered, and the residue on the filter was washed with methanol. This was purified through silica gel column chromatography (dichloromethane/hexane=1/2) to give a white solid of a compound j (3.7 g, 3.5 mmol, yield 82%).

$^1$H NMR (500 MHz, $CDCl_3$, δ): 8.30 (s, 1H), 7.66 (d, J=7.5 Hz, 2H), 7.56 (d, J=7.5 Hz, 4H), 7.48-7.41 (m, 10H), 7.63 (d, J=7.5 Hz, 2H), 7.31-7.30 (m, 4H), 7.13 (d, J=7.5 Hz, 2H)

ASAP Mass Spectrometry: theoretical 1068.4, found 1068.6.

In a nitrogen stream, at 0° C., t-BuLi (1.9 mol/L pentane solution, 2.0 mL, 3.8 mmol) was added to a toluene (37 mL) solution of the compound j (2.7 g, 2.5 mmol), and stirred at 90° C. for 1 hour. The reaction mixture was cooled to 0° C., tribromoboron (0.95 g, 3.8 mmol) was added, and stirred at room temperature for 40 minutes. N-ethyldiisopropylamine (0.98 g, 7.6 mmol) was added to the reaction liquid, and stirred at 100° C. for 15 hours. The resultant reaction mixture was filtered through Celite, and the solvent was evaporated away from the filtrate. This was purified through silica gel column chromatography (toluene/hexane=1/2 to 2/3, ethyl acetate/hexane=1/9) to give a yellow solid of a compound 3 (0.85 g, 0.82 mmol, yield 32%).

$^1$H NMR (500 MHz, $CDCl_3$, δ): 9.18 (d, J=8.0 Hz, 2H), 8.26 (s, 2H), 7.88-7.34 (m, 42H), 7.24 (brs, 3H), 6.52 (s, 2H)

ASAP Mass Spectrometry: theoretical 1041.4, found 1041.5.

Synthesis Example 4

A compound 271 was synthesized according to the following scheme.

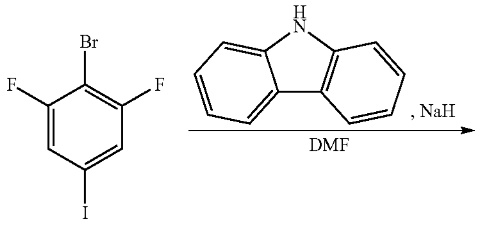

k

-continued

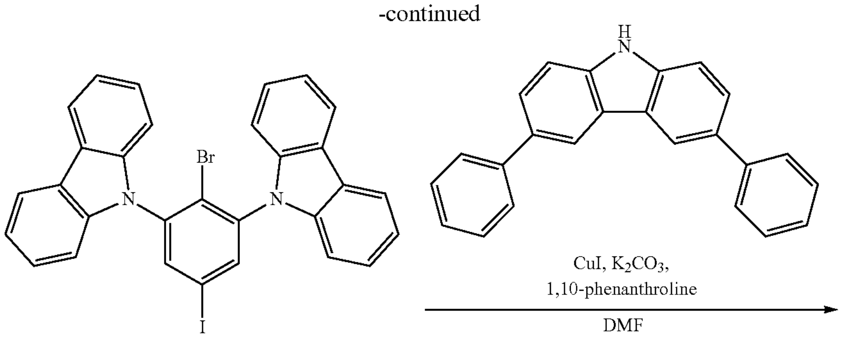

m

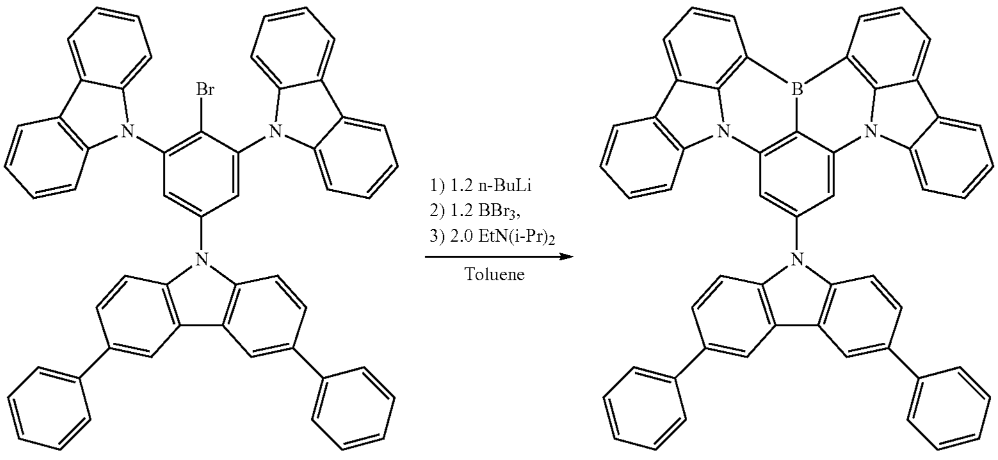

n

271

In a nitrogen stream, a compound k (0.32 g, 1.0 mmol) was added to a dimethylformamide solution (10 mL) of carbazole (0.35 g, 2.1 mmol) and potassium carbonate (0.42 g, 3.0 mmol), and stirred at 130° C. for 15 hours. The mixture was restored to room temperature, water was added, and the precipitated solid was taken out through filtration. This was purified through silica, gel column chromatography (dichloromethane/hexane=1/2) to give a white solid of a compound m (0.42 g, 0.68 mmol, yield 68%).

$^1$H NMR (400 MHz, $CDCl_3$, δ): 8.15 (d, J=7.7 Hz, 4H), 8.00 (d, J=0.8 Hz, 2H), 7.48 (t, J=7.7 Hz, 4H), 7.33 (t, J=7.7 Hz, 4H), 7.20 (d, J=8.1 Hz, 4H).

ASAP Mass Spectrometry: theoretical 611.97, found 612.90.

In a nitrogen stream, 1,10-phenanthroline (2.16 g, 12.0 mmol), copper iodide (2.29 g, 12.0 mmol) and potassium carbonate (3.31 g, 24.0 mmol) were added to a dimethylformamide (120 mL) solution of the compound m (7.36 g, 12.0 mmol) and 3,6-diphenylcarbazole (5.74 g, 18.0 mmol), and stirred at 135° C. for 6 hours. The mixture was restored to room temperature, water was added, the precipitated solid was filtered through a Celite, the residue on the filter was dissolved in dichloromethane. The solvent was evaporated away from the filtrate, and purified through silica gel column chromatography (toluene/hexane=4/6 to 1/0) to give a white solid of a compound n (6.29 g, 7.81 mmol, yield 65%).

$^1$H NMR (400 MHz, $CDCl_3$, δ): 8.35 (s, 2H), 8.19 (d, J=7.7 Hz, 4H), 8.05 (s, 2H), 7.71-7.66 (m, 8H), 7.54 (t, J=7.7 Hz, 4H), 7.46 (t, J=7.7 Hz, 4H), 7.39 (d, J=7.7 Hz, 6H), 7.35 (d, J=7.7 Hz, 4H).

ASAP Mass Spectrometry: theoretical 803.19, found 804.25.

In a nitrogen stream, at −30° C. n-BuLi (1.6 mol/L hexane solution, 0.04 mL, 0.06 mmol) was added to a toluene (0.6 mL) solution of the compound n (48 mg, 0.06 mmol), and stirred at 0° C. for 30 minutes. The reaction mixture was cooled at −30° C., tribromoboron (16.5 mg, 0.07 mmol) was added, and stirred at room temperature for 30 minutes. N,N-diisopropylethylamine (15.5 mg, 0.12 mmol) was added to the reaction liquid, and stirred at 120° C. for 3 hours. The resultant reaction mixture was filtered through Celite, and the solvent was evaporated away from the filtrate. This was purified through silica gel column chromatography (ODCB) to give a yellow solid of a compound 4 (31 mg, 0.03 mmol, yield 58%).

$^1$H-NMR (400 MHz, $CDCl_3$, δ): 9.08 (d, J=7.4 Hz, 2H), 8.67 (s, 2H), 8.52 (s, 2H), 8.46 (d, J=7.4 Hz, 2H), 8.38 (d, J=8.5 Hz, 2H), 8.28 (d, J=7.4 Hz, 2H), 7.95 (d, J=8.5 Hz, 2H), 7.82-7.77 (m, 8H), 7.58-7.45 (m, 8H), 7.38 (t, J=7.4 Hz, 2H).

ASAP Mass Spectrometry: theoretical 733.80, found 733.27.

Example

The compound 1 and PYD2Cz were evaporated from different evaporation sources onto a quartz substrate according to a vacuum evaporation method at a vacuum degree of less than $3\times10^{-3}$ Pa to form a thin film having a thickness of 100 nm in which the concentration of the compound 1 was 1% by weight, and this is referred to as a doped thin film of Example 1.

Comparative Example

In the same manner except that the following comparative compound 1 was used in place of the compound 1, a thin film was formed and this is referred to as a doped thin film of Comparative Example 1. Ph in the structure of the comparative compound 1 is an unsubstituted phenyl group.

[Measurement and Evaluation]

Using 300-nm excitation light, emission spectra of these thin film were observed, and the emission maximum wavelength and the full width at half maximum thereof were measured, and the photoluminescence quantum yield (PLQY) thereof was also measured. The results are shown in Table 2. The results in Table 2 indicate that the emission maximum wavelength of the film doped with the compound 1 is shortened though the conjugated system of the compound 1 is broadened more than that of the comparative compound 1. In addition, it is shown that as compared with the comparative compound 1, the compound 1 has a narrowed full width at half maximum and an increased photoluminescence quantum yield, that is, the compound 1 has excellent emission characteristics.

TABLE 2

| | Emission Maximum Wavelength (nm) | Full Width at Half Maximum (nm) | PLQY (%) |
|---|---|---|---|
| Example 1 (compound 1) | 448 | 26 | 93 |
| Comparative Example 1 (comparative compound 1) | 464 | 33 | 89 |

The relationship between the compound 1 and the comparative compound 1 of the invention is the same as the relationship between the compound 2 of the invention and the comparative compound 2, the relationship between the compound 3 of the invention and the comparative compound 3 and the relationship between the compound 271 of the invention and the comparative compound 271.

For example, a thin film formed using the compound 3 in place of the compound 1 has a shorter emission maximum wavelength, has a narrower full width at half maximum and has a higher PLQY than a thin film formed using the comparative compound 3 in place of the compound 1. Specifically, it is confirmed that the thin film formed using the compound 3 has an emission maxim un wavelength of 468 nm, has a narrowed full width at half maximum of 27 nm, and has a high PLQY of 90%.

In addition, it is confirmed that the thin film formed using, for example, the comparative compound 271 in place of the compound 1 has an emission maximum wavelength of 486 nm and a full with at half maximum of 42 nm, while, on the other hand, the thin film formed using the compound 271 of the invention has a shorter emission maximum wavelength of 473 nm, and has a significantly narrowed full width at half maximum of 28 nm. Also it is confirmed that the thin film formed using the compound 271 of the invention keeps a high emission efficiency.

The relationship between the compound of the invention and the comparative compound is supported also by a mathematical chemical method using a program Q-Chem 5.1 by Q-Chem Corporation. In this, a B3LYP/6-31G(d) method is used for molecular structure optimization and electron state computation in a ground-singlet state S0, and a time-dependent density functional theory (TD-DFT) method is used for computation of the lowest excited singlet energy level ($E_{S1}$). As a result, the resultant values confirmed that the compound 1 can shorten the emission maximum wavelength more than the comparative compound 1, which well accorded with the tendency of the found data of the emission maximum wavelength. The same computation was applied to the compound 2 and the comparative compound 2, in which the resultant values also confirmed that the compound 2 can shorten the emission maximum wavelength more than the comparative compound 2.

Compound 1

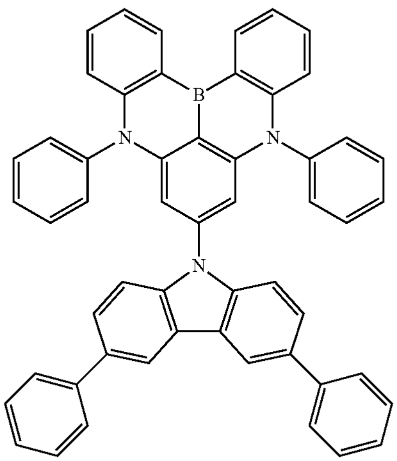

Comparative Compound 1

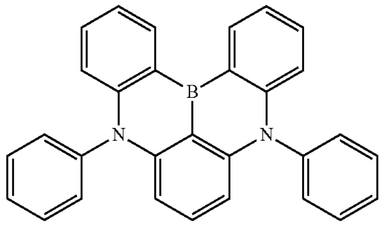

Compound 2

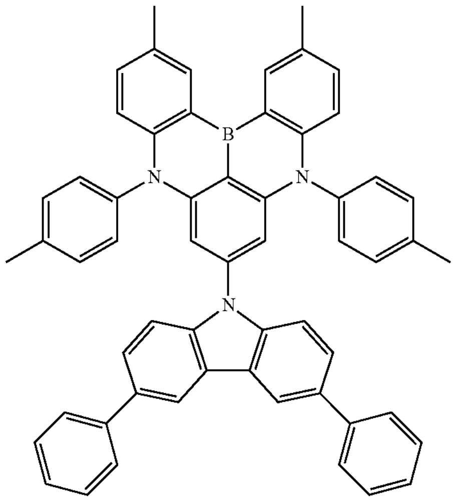

-continued

Comparative Compound 2

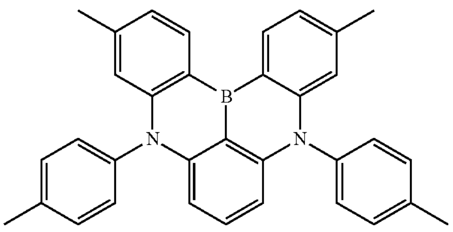

Compound 3

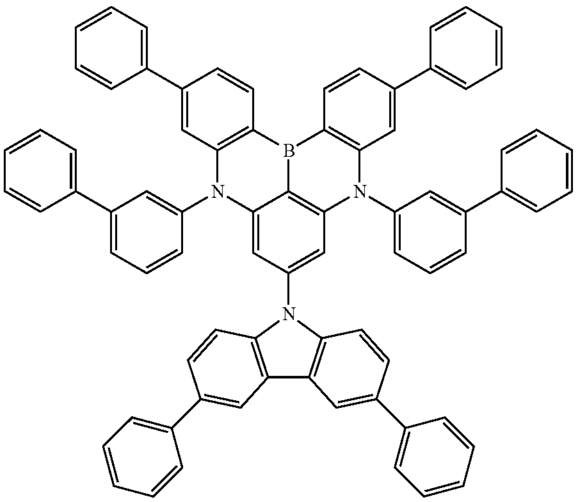

Comparative Compound 3

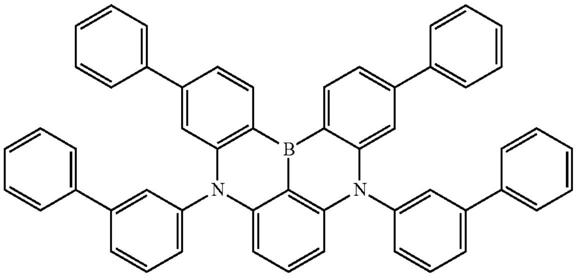

Compound 271

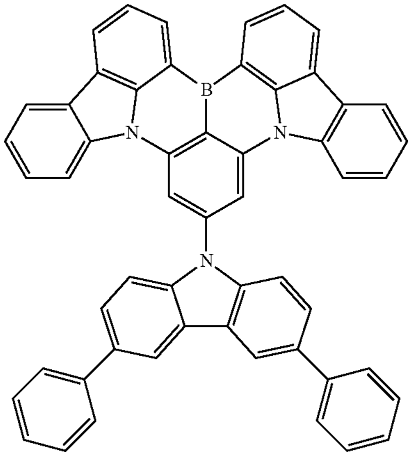

-continued

Comparative Compound 271

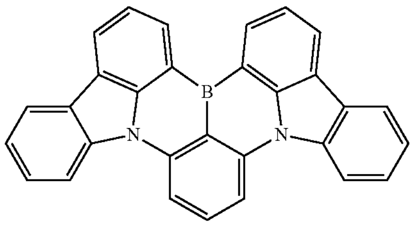

PYD2Cz

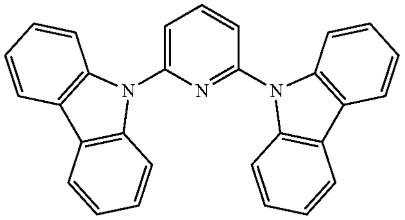

Figure 2:
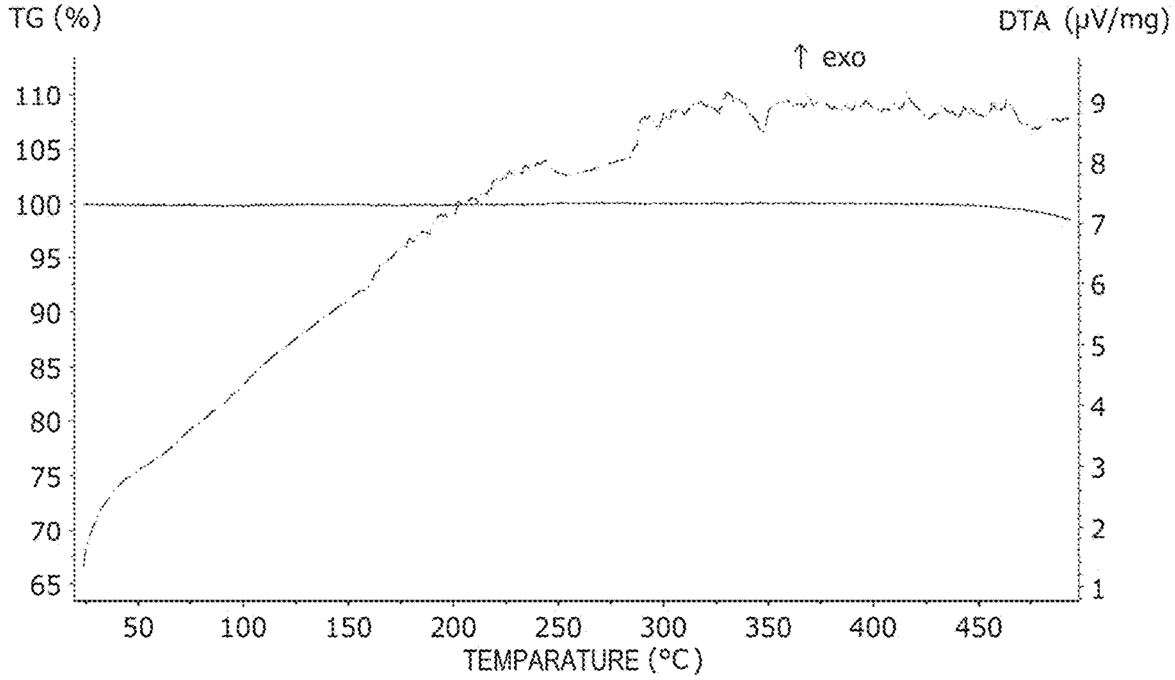
FIG. 2 This is a graph showing results of thermal gravimetric differential thermal analysis of compound 1.

Using a thermal gravimetric differential thermal analyzer (STA 2500 Regulus, by NETSCH Corporation), the compound 1 was subjected to thermal gravimetric differential thermal analysis. For the measurement, the sample was heated from 20° C. up to 500° C. at a speed of 10° C./min under an atmospheric pressure. A graph of the results of thermal gravimetry (TG) and a graph of the results of differential thermal analysis (DTA) are shown in FIG. 2. As in FIG. 2, the temperature (Td5) at which the mass of the compound 1 reduced by 5% from the initial value is higher than 500° C., which confirms that the compound 1 has excellent heat resistance.

Also the compound 2, the compound 3 and the compound 271 can be evaluated to have good heat resistance in the same manner as above.

INDUSTRIAL APPLICABILITY

According to the present invention, there can be provided a compound having excellent light emission characteristics and a compound capable of emitting at a short wavelength. Accordingly, the light emitting material of the present invention can be effectively used in organic light-emitting devices such as organic electroluminescent devices. Accordingly, the industrial applicability of the present invention is great.

REFERENCE SIGNS LIST

1 Substrate
2 Anode
3 Hole Injection Layer
4 Hole Transporting Layer
5 Light-Emitting Layer
6 Electron Transporting Layer
7 Cathode

The invention claimed is:

1. A compound represented by the following general formula (1):

General Formula (1)

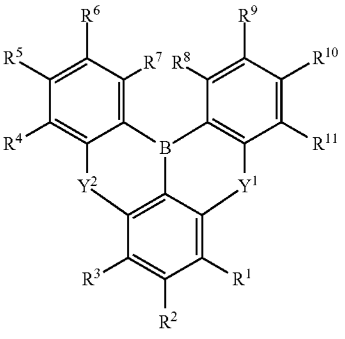

wherein:

$Y^1$ represents N—$R^A$, $Y^2$ represents N—$R^A$, $R^A$ each independently represents a substituted or unsubstituted aryl group, $R^1$ to $R^{11}$ each independently represent a hydrogen atom, a substituted or unsubstituted alkyl group, or a substituted or unsubstituted aryl group, none of $R^1$ and $R^2$, $R^2$ and $R^3$, $R^4$ and $R^5$, $R^5$ and $R^6$, $R^6$ and $R^7$, $R^7$ and $R^8$, $R^8$ and $R^9$, $R^9$ and $R^{10}$, $R^{10}$ and $R^{11}$, $R^A$ and $R^4$, and $R^A$ and $R^{11}$ bond to each other to form a cyclic structure, provided that at least one of $R^1$, $R^2$ and $R^3$ is a group represented by the following general formula (2), General Formula (2)

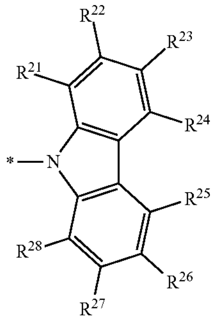

wherein $R^{21}$ to $R^{28}$ each independently represent a hydrogen atom, a substituted or unsubstituted aryl group, $R^{21}$ and $R^{22}$, $R^{22}$ and $R^{23}$, $R^{23}$ and $R^{24}$, $R^{25}$ and $R^{26}$, $R^{26}$ and $R^{27}$, and $R^{27}$ and $R^{28}$ each can bond to each other to form a cyclic structure, provided that $R^{23}$ and $R^{26}$ are independently a substituted or unsubstituted phenyl group, and * indicates a bonding position.

2. The compound according to claim 1, wherein $R^7$ and $R^8$ are both hydrogen atoms.

3. The compound according to claim 1, wherein $R^5$ and $R^{10}$ each are independently a substituted or unsubstituted aryl group, or a substituted or unsubstituted alkyl group.

4. The compound according to claim 1, wherein $R^6$ and $R^9$ each are independently a substituted or unsubstituted aryl group, or a substituted or unsubstituted alkyl group.

5. The compound according to claim 1, wherein $R^2$ is a group represented by the general formula (2).

6. The compound according to claim 1, having any of the following structures:

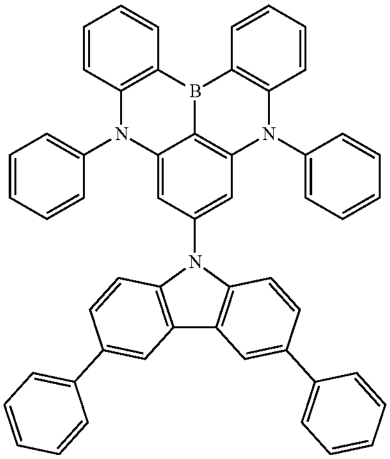

,

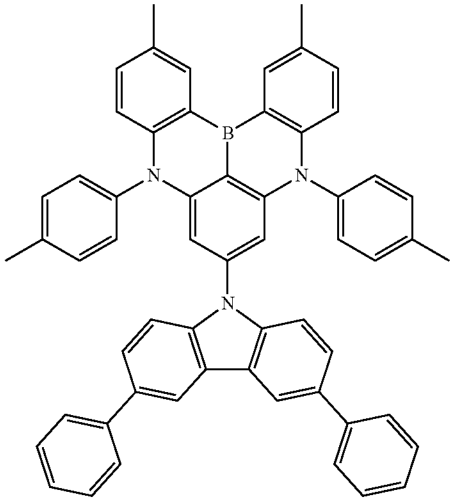

and

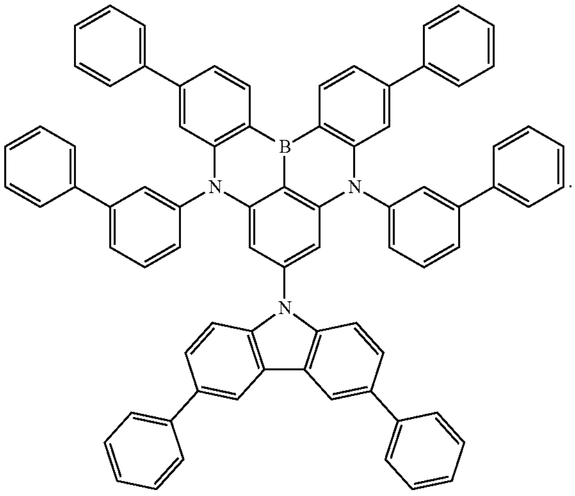

.

7. An organic light-emitting device comprising the compound of claim 1.

8. The organic light-emitting device according to claim 7, wherein the device has a layer that contains the compound, and the layer also contains a host material.

9. The organic light-emitting device according to claim 7, wherein the device has a layer that contains the compound, and the layer also contains a light-emitting material having a structure that differs from that of the compound.

10. The organic light-emitting device according to claim 9, wherein the amount of light emission from the light-emitting material is larger than the amount of light emission from the compound.

11. The organic light-emitting device according to claim 7, wherein among the materials contained in the device, the amount of light emission from the compound is the maximum.

12. The organic light-emitting device according to claim 7, which is an organic light-emitting diode (OLED).

13. The organic light-emitting device according to claim 7, which emits delayed fluorescence.

14. A compound represented by the following general formula (A):

General Formula (A)

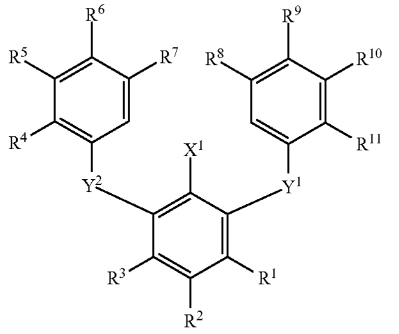

wherein:

$X^1$ represents a halogen atom, $Y^1$ represents N—$R^A$, $Y^2$ represents N—$R^A$, $R^A$ each independently represents a substituted or unsubstituted aryl group, or a substituted or unsubstituted heteroaryl group, $R^1$ to $R^{11}$ each independently represent a hydrogen atom, a substituted or unsubstituted alkyl group, or a substituted or unsubstituted aryl group, none of $R^1$ and $R^2$, $R^2$ and $R^3$, $R^4$ and $R^5$, $R^5$ and $R^6$, $R^6$ and $R^7$, $R^7$ and $R^8$, $R^8$ and $R^9$, $R^9$ and $R^{10}$, $R^{10}$ and $R^{11}$, $R^A$ and $R^4$, and $R^A$ and $R^{11}$ bond to each other to form a cyclic structure, provided that at least one of $R^1$, $R^2$ and $R^3$ is a group represented by the following general formula (2), General Formula (2)

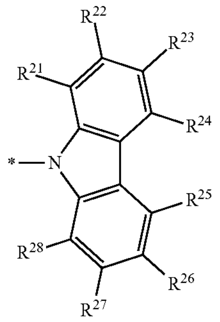

wherein $R^{21}$ to $R^{28}$ each independently represent a hydrogen atom, a substituted or unsubstituted aryl group, $R^{21}$ and $R^{22}$, $R^{22}$ and $R^{23}$, $R^{23}$ and $R^{24}$, $R^{25}$ and $R^{26}$, $R^{26}$ and $R^{27}$, and $R^{27}$ and $R^{28}$ each can bond to each other to form a cyclic structure, provided that $R^{23}$ and $R^{26}$ are independently is a substituted or unsubstituted phenyl group, and * indicates a bonding position.

* * * * *